(12) United States Patent
Terliuc

(10) Patent No.: US 8,828,090 B2
(45) Date of Patent: Sep. 9, 2014

(54) LINER FOR TUBULAR BODY PORTION AND APPARATUS AND METHODS FOR APPLICATION THEREOF

(75) Inventor: Gad Terliuc, Ra'anana (IL)

(73) Assignee: Binerix Medical Ltd., Ra'anana (IL)

( * ) Notice: Subject to any disclaimer, the term of this patent is extended or adjusted under 35 U.S.C. 154(b) by 395 days.

(21) Appl. No.: 13/058,536

(22) PCT Filed: Aug. 11, 2009

(86) PCT No.: PCT/IL2009/000779
§ 371 (c)(1),
(2), (4) Date: Feb. 11, 2011

(87) PCT Pub. No.: WO2010/018571
PCT Pub. Date: Feb. 18, 2010

(65) Prior Publication Data
US 2011/0137428 A1 Jun. 9, 2011

Related U.S. Application Data

(60) Provisional application No. 61/136,112, filed on Aug. 13, 2008, provisional application No. 61/136,552, filed on Sep. 15, 2008.

(51) Int. Cl.
| | | |
|---|---|---|
| A61F 2/04 | (2013.01) |
| A61F 2/95 | (2013.01) |
| A61F 2/06 | (2013.01) |
| A61F 5/00 | (2006.01) |
| A61B 17/11 | (2006.01) |
| A61M 25/04 | (2006.01) |
| A61B 17/064 | (2006.01) |
| A61B 17/00 | (2006.01) |
| A61M 25/10 | (2013.01) |
| A61B 17/115 | (2006.01) |
| A61B 17/068 | (2006.01) |

(52) U.S. Cl.
CPC ............ A61B 17/1114 (2013.01); A61M 25/04 (2013.01); A61F 2/95 (2013.01); A61F 2002/9511 (2013.01); A61F 2/06 (2013.01); A61B 2017/0647 (2013.01); A61F 5/0036 (2013.01); A61B 2017/00818 (2013.01); A61M 25/10 (2013.01); A61F 2002/045 (2013.01); A61B 2017/1157 (2013.01); A61B 17/068 (2013.01)
USPC .................... 623/23.64; 623/23.65; 623/1.13; 606/198

(58) Field of Classification Search
CPC ...................................... A61F 2/04; A61F 2/06
USPC ............................ 623/23.64–23.67, 1.1, 1.13
See application file for complete search history.

(56) References Cited

U.S. PATENT DOCUMENTS 4,134,405 A 1/1979 Smit
4,315,509 A 2/1982 Smit
(Continued)

FOREIGN PATENT DOCUMENTS

WO WO2008030403 3/2008

*Primary Examiner* — Jason-Dennis Stewart
(74) *Attorney, Agent, or Firm* — Daniel J. Swirsky; AlphaPatent Associates Ltd.

(57) ABSTRACT

A tubular body portion lining assembly adapted for insertion into a tubular body portion of a patient including a flexible tubular liner, liner placing functionality adapted to place at least a portion of the tubular liner between first and second locations within the tubular body portion, and at least one anchor adapted for anchoring the tubular liner to the tubular body portion at least a first selectable anchoring location.

15 Claims, 32 Drawing Sheets

(56) References Cited

U.S. PATENT DOCUMENTS

| | | | |
|---|---|---|---|
| 5,282,824 A | 2/1994 | Gianturco | |
| 5,387,235 A | 2/1995 | Chuter | |
| 6,245,011 B1* | 6/2001 | Dudda et al. | 600/104 |
| 6,478,782 B1 | 11/2002 | Wada | |
| 6,740,121 B2 | 5/2004 | Geitz | |
| 6,939,374 B2 | 9/2005 | Banik et al. | |
| 6,946,002 B2 | 9/2005 | Geitz | |
| 7,025,791 B2 | 4/2006 | Levine et al. | |
| 7,122,058 B2 | 10/2006 | Levine et al. | |
| 7,160,312 B2 | 1/2007 | Saadat | |
| 7,175,669 B2 | 2/2007 | Geitz | |
| 7,204,842 B2 | 4/2007 | Geitz | |
| 7,220,284 B2 | 5/2007 | Kagan et al. | |
| 7,267,694 B2 | 9/2007 | Levine et al. | |
| 7,288,101 B2 | 10/2007 | Deem et al. | |
| 7,329,285 B2 | 2/2008 | Levine et al. | |
| 7,335,210 B2 | 2/2008 | Smit | |
| 7,347,875 B2 | 3/2008 | Levine et al. | |
| 2004/0220682 A1* | 11/2004 | Levine et al. | 623/23.65 |
| 2004/0249362 A1 | 12/2004 | Levine et al. | |
| 2005/0075622 A1 | 4/2005 | Levine et al. | |
| 2005/0080395 A1 | 4/2005 | Levine et al. | |
| 2005/0080431 A1 | 4/2005 | Levine et al. | |
| 2005/0080491 A1 | 4/2005 | Levine et al. | |
| 2005/0085923 A1 | 4/2005 | Levine et al. | |
| 2005/0125020 A1 | 6/2005 | Meade et al. | |
| 2005/0125075 A1 | 6/2005 | Meade et al. | |
| 2006/0009858 A1 | 1/2006 | Levine | |
| 2006/0161139 A1* | 7/2006 | Levine et al. | 606/1 |
| 2006/0161187 A1 | 7/2006 | Levine | |
| 2006/0235448 A1 | 10/2006 | Roslin | |
| 2007/0005147 A1 | 1/2007 | Levine | |
| 2007/0083271 A1* | 4/2007 | Levine et al. | 623/23.64 |
| 2008/0039878 A1* | 2/2008 | Williams et al. | 606/153 |
| 2008/0058887 A1 | 3/2008 | Griffin | |

* cited by examiner

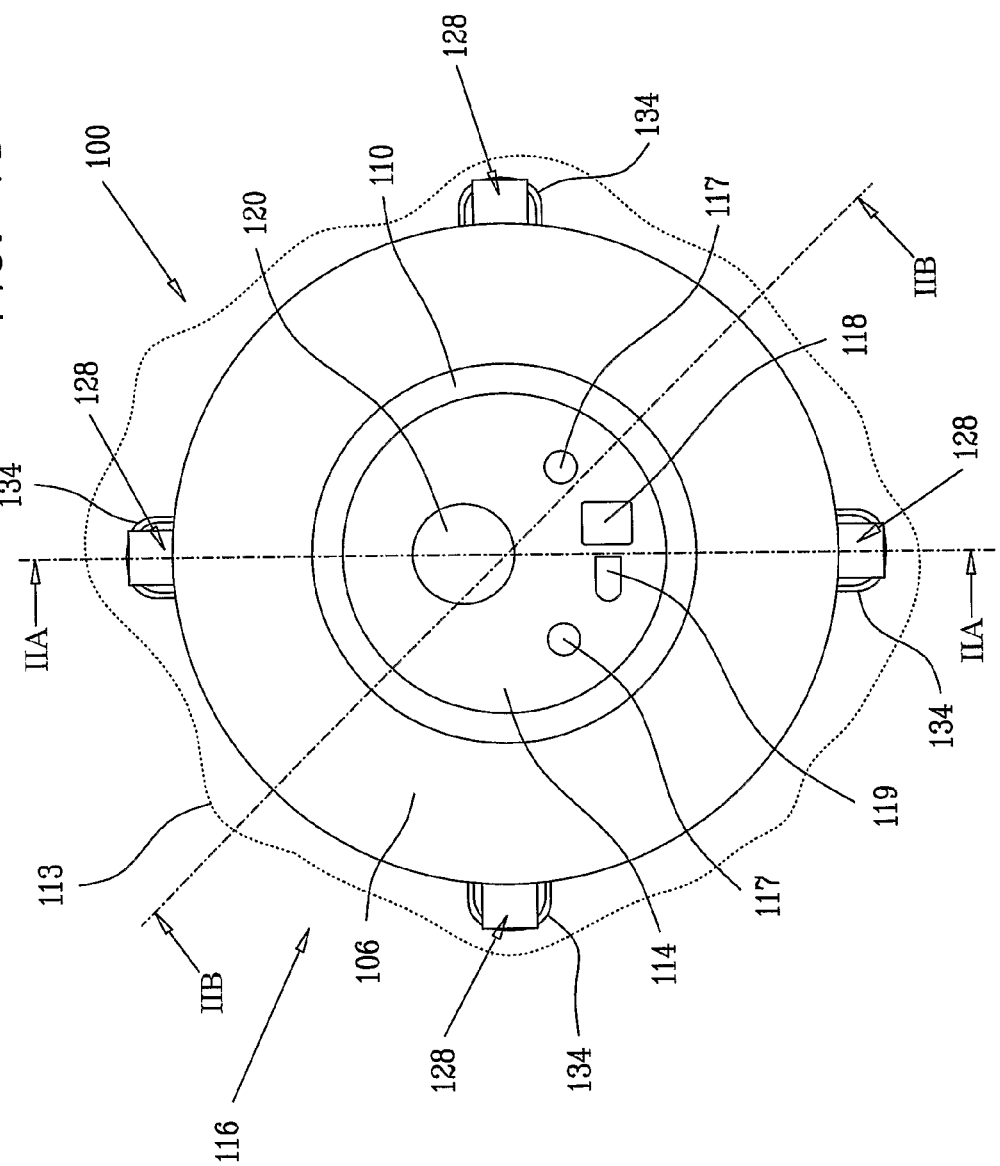

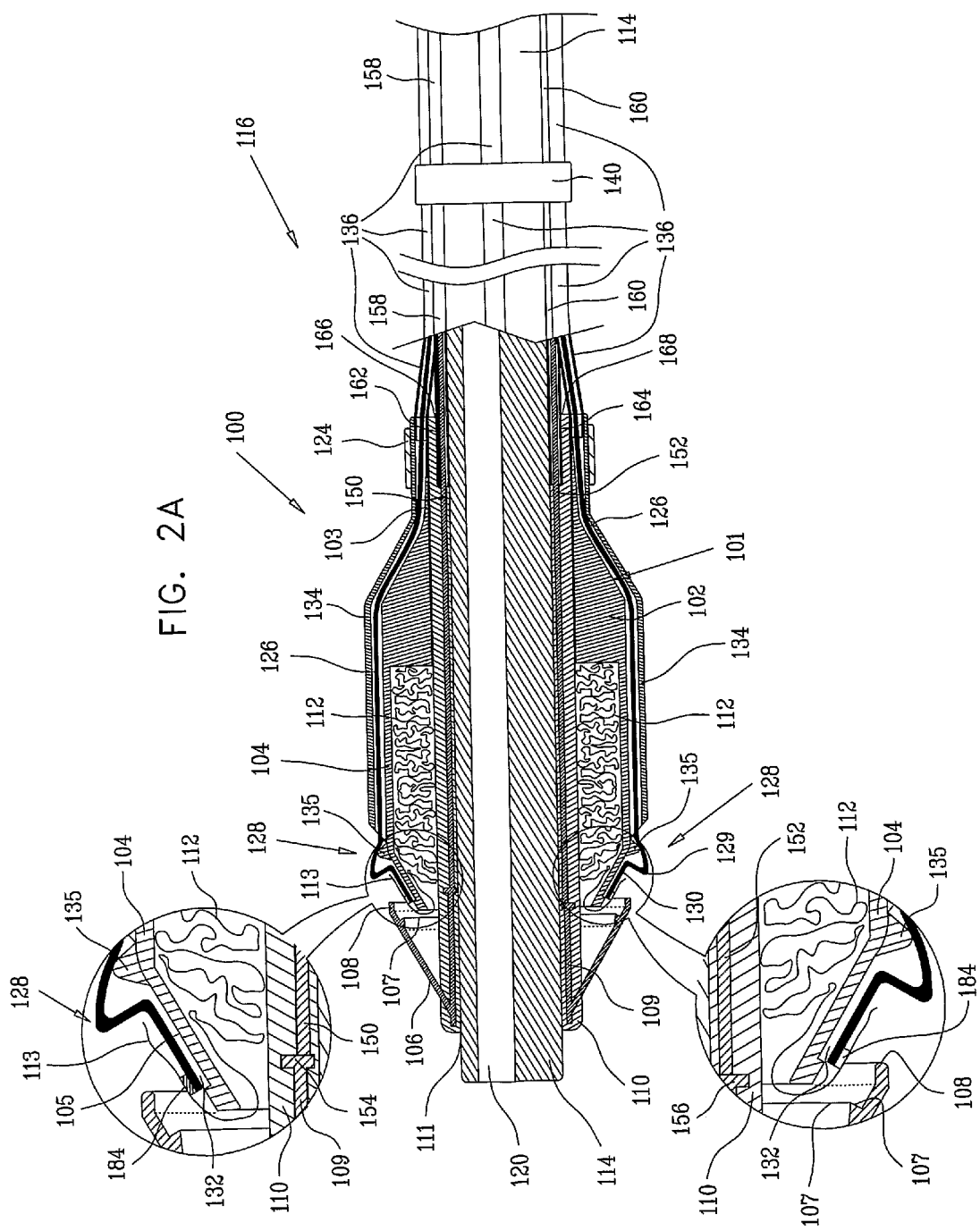

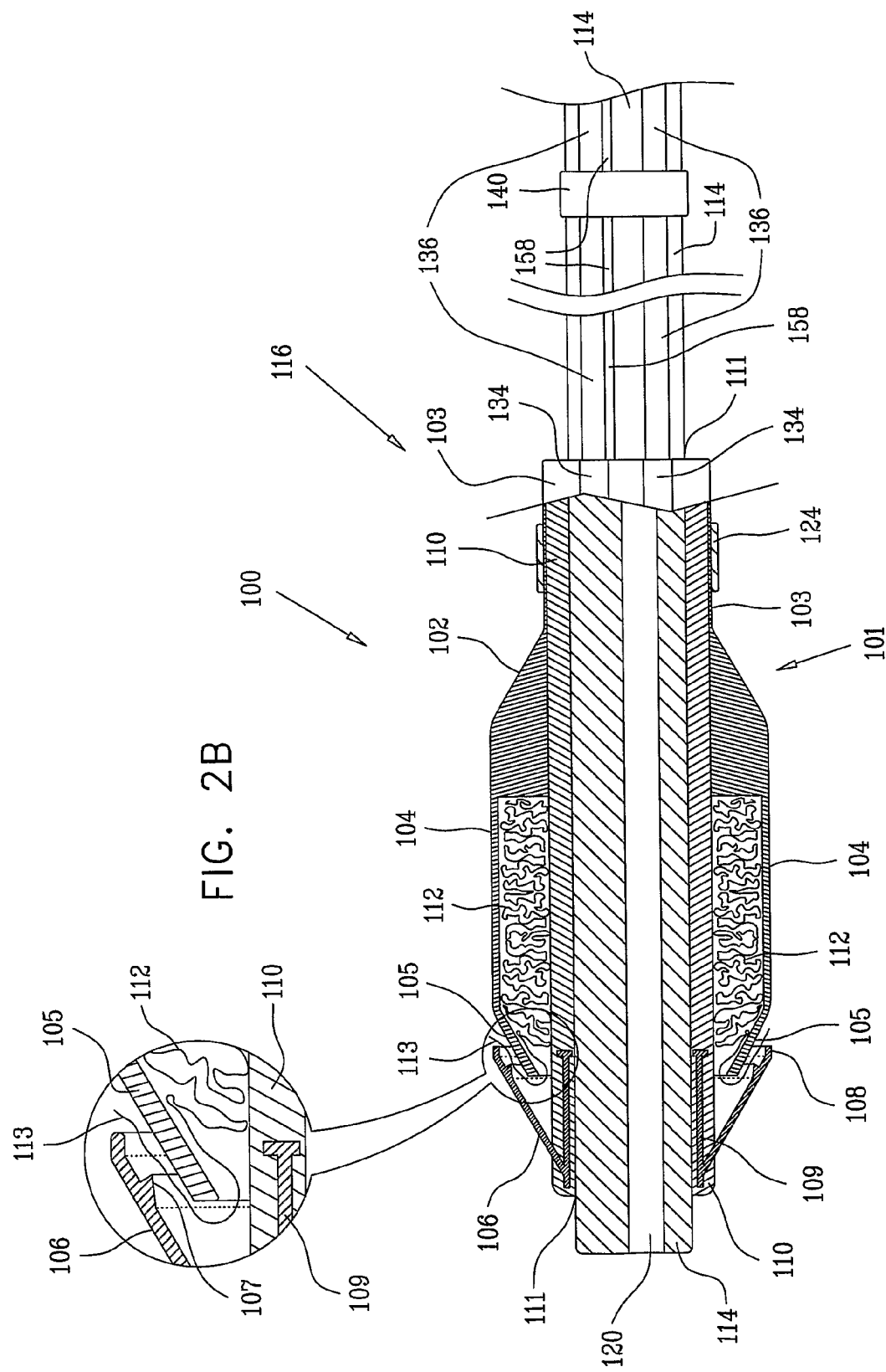

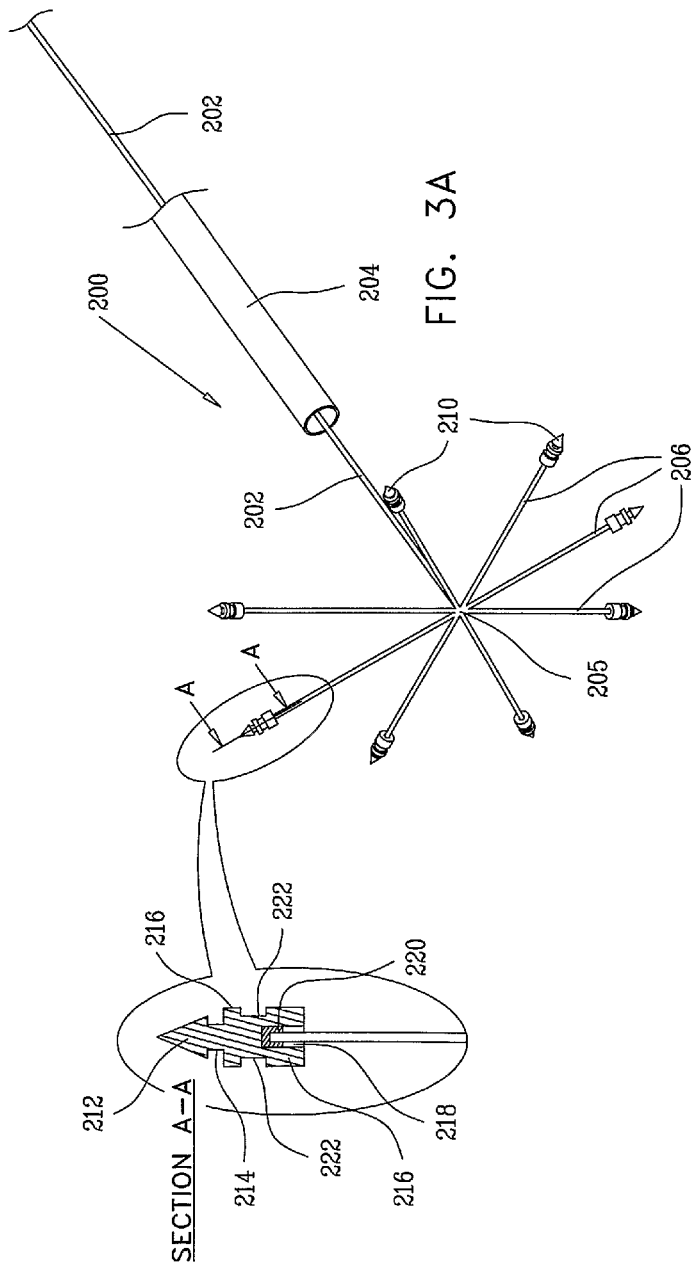
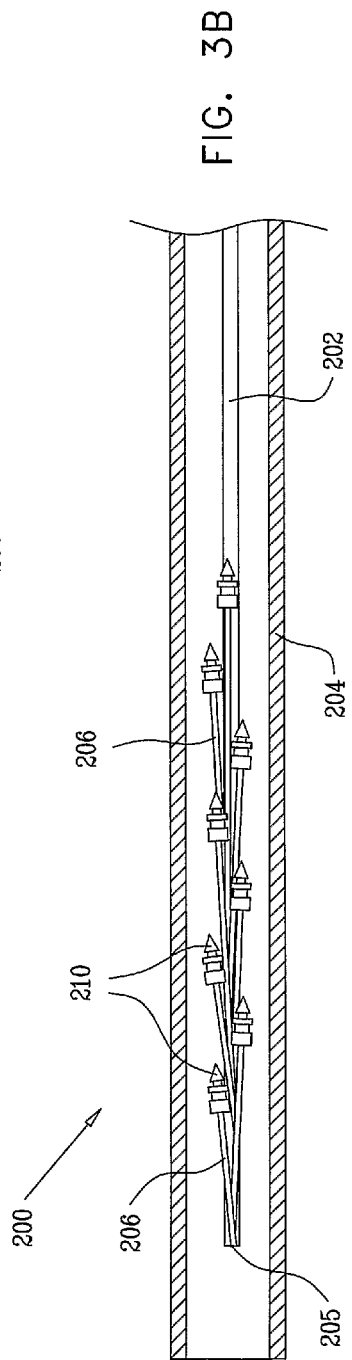

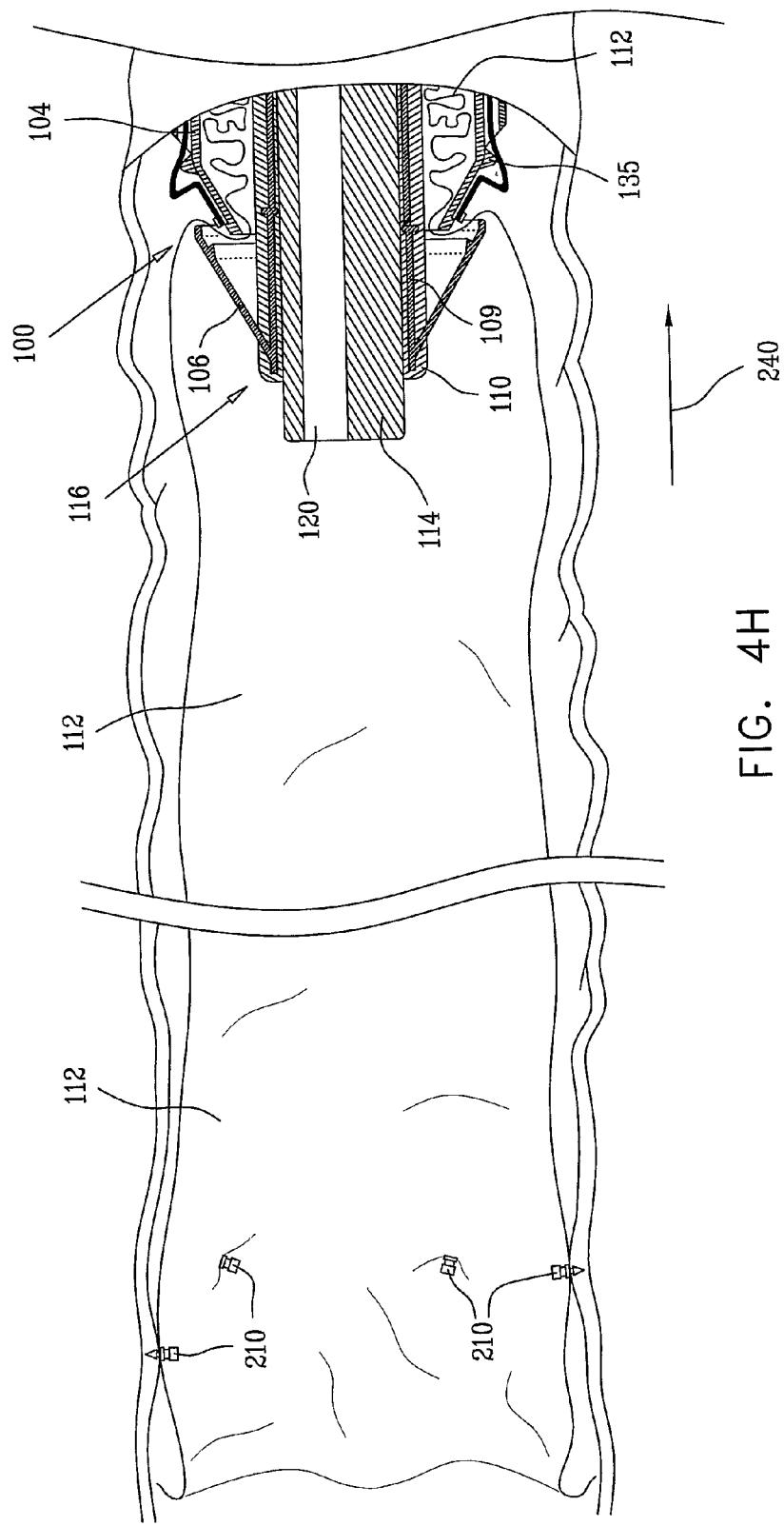

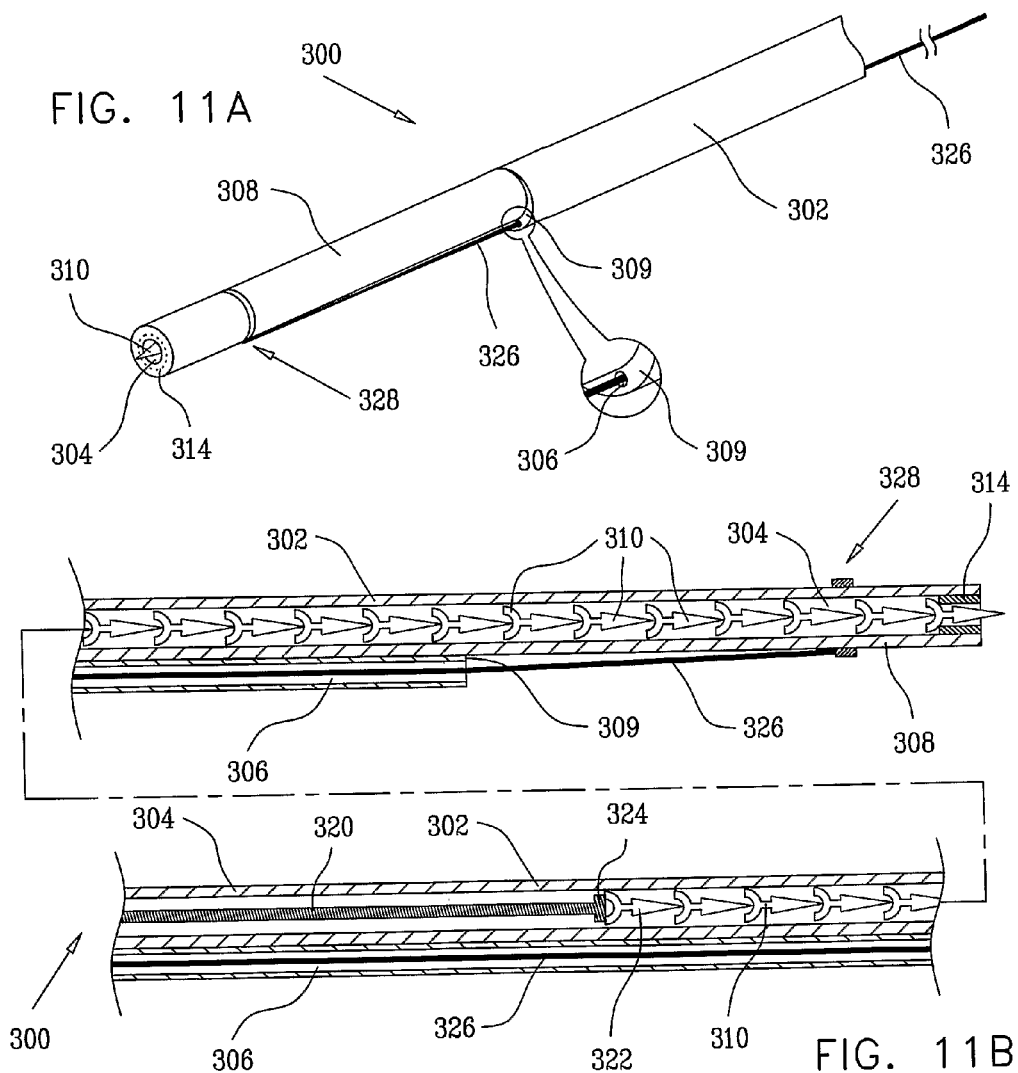
FIG. 11A
FIG. 11B
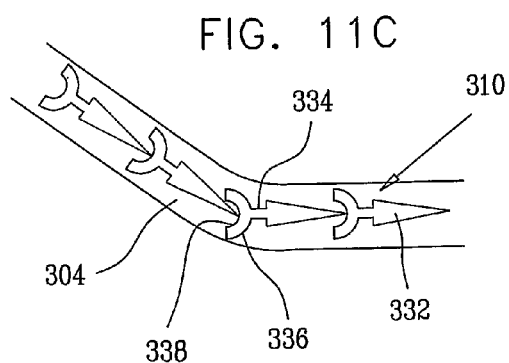
FIG. 11C
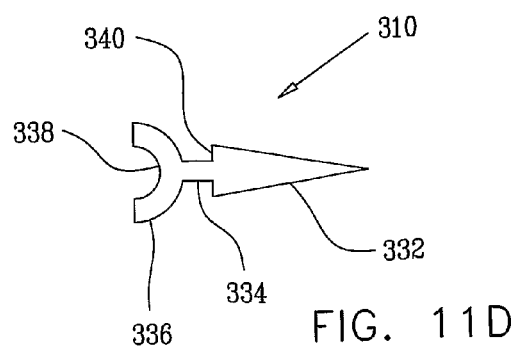
FIG. 11D

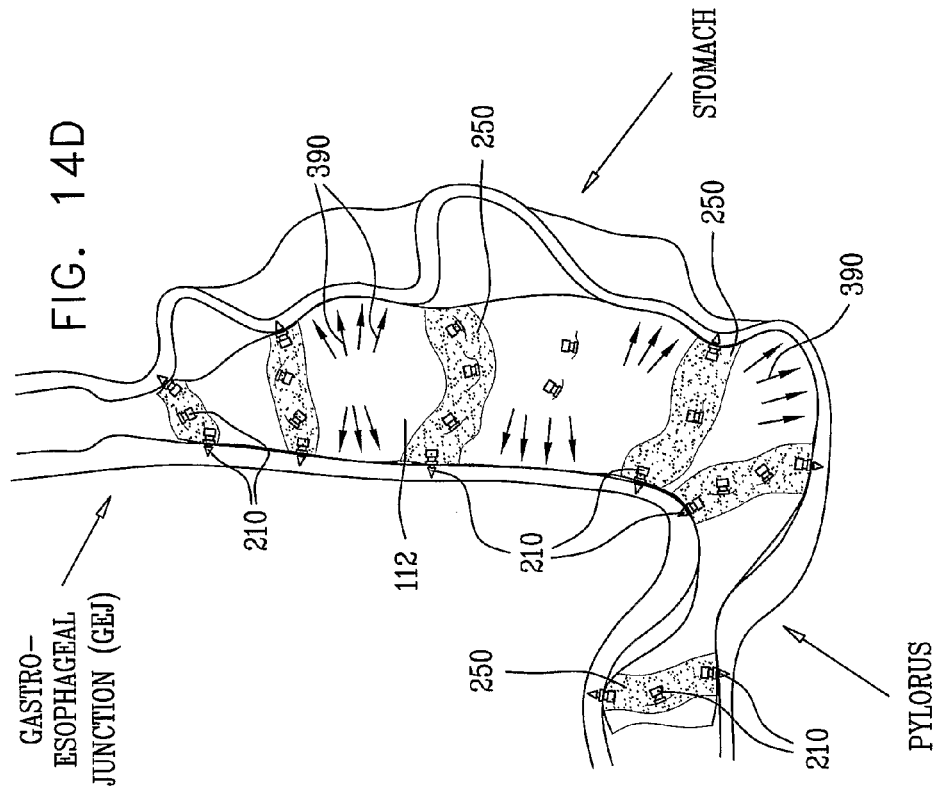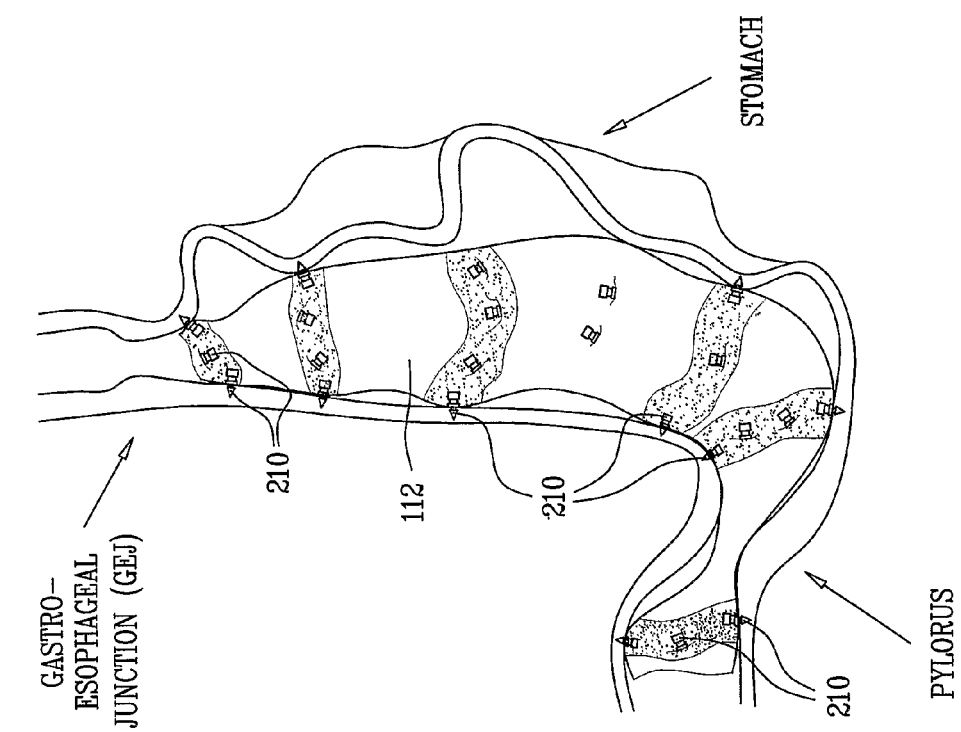

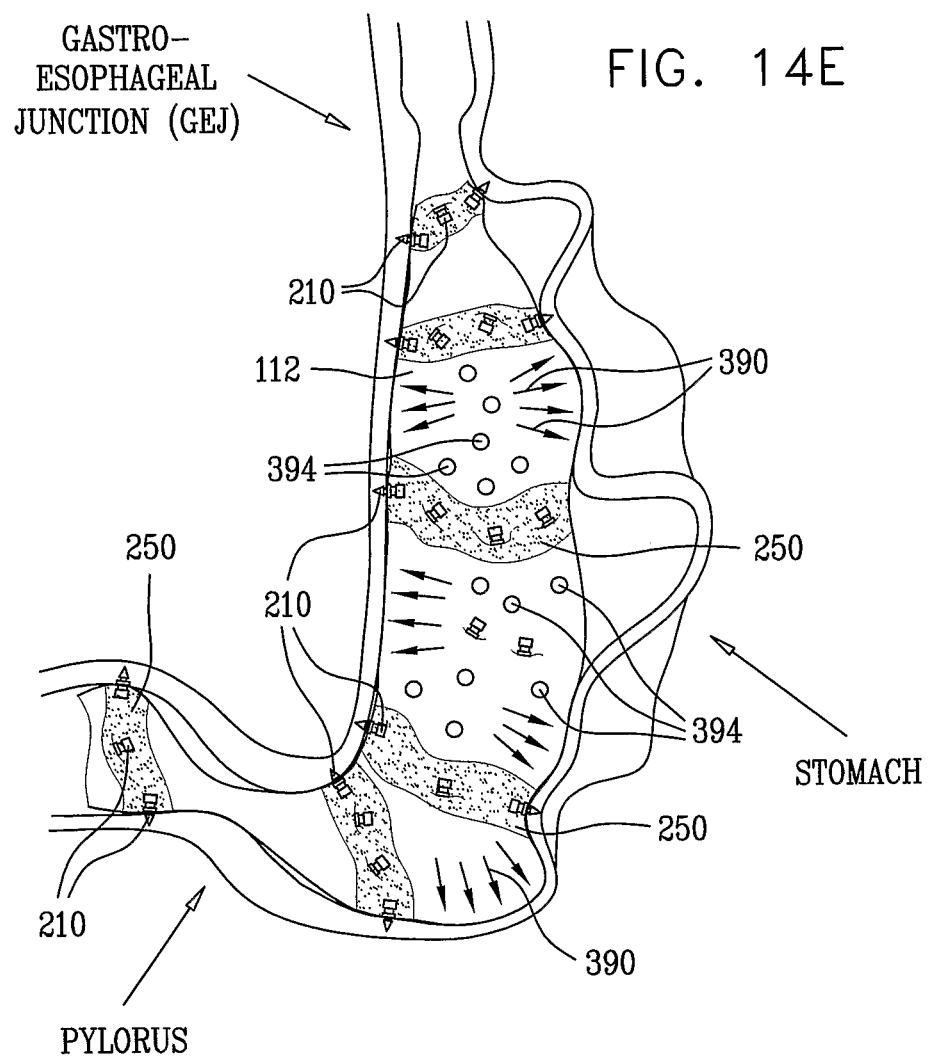

LINER FOR TUBULAR BODY PORTION AND APPARATUS AND METHODS FOR APPLICATION THEREOF

CROSS REFERENCE TO RELATED APPLICATIONS

Reference is made to the following related applications, the disclosures of which are hereby incorporated by reference and priority of which is hereby claimed pursuant to 35 U.S.C. 37 CFR 1.78(a) (4) and (5)(i):

This application is a U.S. National Phase Application under 35 U.S.C. 371 of PCT International Application No. PCT/IL2009/000779, which has an international filing date of Aug. 11, 2009, and which claims priority from U.S. Provisional Patent Application Ser. No. 61/136,112, filed Aug. 13, 2008, entitled ENDOSCOPIC LINER AND METHODS OF APPLICATION; and U.S. Provisional Patent Application Ser. No. 61/136,552, filed Sep. 15, 2008, entitled ENDOSCOPIC LINER AND METHODS OF APPLICATION THEREOF.

Reference is also made to inventor's copending PCT Application No. PCT/IL2005/000849, filed Aug. 8, 2005; and PCT Application No. PCT/IL2007/000600, filed May 17, 2007, the disclosures of which are hereby incorporated by reference.

FIELD OF THE INVENTION

The present invention relates generally to systems and methodologies for treating tubular body portions of a patient.

BACKGROUND OF THE INVENTION

The following patent publications are believed to represent the current state of the art:

U.S. Pat. Nos. 4,134,405; 5,282,824; 5,387,235; 6,740,121; 6,939,374; 6,946,002; 7,025,791; 7,122,058; 7,160,312; 7,175,669; 7,204,842; 7,267,694; 7,288,101; 7,329,285; 7,335,210; 7,347,875;

U.S. Patent Application publication Nos. 2004/0220682; 2004/0249362; 2005/0075622; 2005/0080395; 2005/0080431; 2005/0080491; 2005/0085923; 2005/0125020; 2005/0125075; 2006/0009858; 2006/0161187; 2006/0235448; 2007/0005147; and International Patent Application publication WO 2008/030403.

SUMMARY OF THE INVENTION

The present invention seeks to provide improved assemblies for liner deployment within tubular body portions of a patient.

There is thus provided in accordance with a preferred embodiment of the present invention a tubular body portion lining assembly adapted for insertion into a tubular body portion of a patient including a flexible tubular liner, liner placing functionality adapted to place at least a portion of the tubular liner between first and second locations within the tubular body portion, and at least one anchor adapted for anchoring the tubular liner to the tubular body portion at least a first selectable anchoring location.

In accordance with a preferred embodiment of the present invention the tubular body portion lining assembly also includes an elongate, flexible inserter for selectably positioning the tubular liner within the tubular body portion, thereby providing a lining system. Preferably, the inserter includes an endoscope. Additionally or alternatively, the tubular body portion lining assembly also includes tubular liner detaching functionality for selectably detaching a selectable portion of the tubular liner from a remainder of the tubular liner. Yet preferably, the detaching functionality includes cutting functionality operative to cut the tubular liner within the tubular body portion.

Preferably, the tubular body portion lining assembly also includes anchoring functionality operative to cause plural ones of the at least one anchor to secure the tubular liner to the tubular body portion at multiple anchoring locations. Additionally or alternatively, at least the liner placing functionality is adapted to place multiple portions of the tubular liner at selectable locations within the tubular body portion. Preferably, the multiple portions of the tubular linear have at least two different lengths. Additionally or alternatively, the tubular body portion lining assembly also includes at least one tube traversing the tubular body portion lining assembly. Preferably, the tubular body portion lining assembly also includes a selectably inflatable balloon mounted onto the tubular body portion lining assembly.

In accordance with a preferred embodiment of the present invention, the tubular body portion lining assembly includes a plurality of generally circumferentially disposed reinforced portions. Preferably, the tubular liner is generally stretchable intermediate the plurality of generally circumferentially disposed reinforced portions. Preferably, the tubular body portion lining assembly also includes a generally tubular housing having an outer diameter greater than 2 cm in which the tubular liner is located. Yet preferably, the tubular body portion lining assembly includes a generally tubular housing having an outer diameter greater than 3 cm in which the tubular liner is located. Additionally or alternatively, the tubular liner is selectably narrowable and also includes selectably narrowing twisting functionality for twisting the selectably narrowable tubular liner, thereby to effect selectable narrowing thereof.

There is also provided in accordance with another preferred embodiment of the present invention an anchoring assembly for use within a tubular body portion including a multiplicity of individual anchors, and anchoring functionality adapted for simultaneous anchoring of the multiplicity of individual anchors within the tubular body portion.

There is also provided in accordance with yet another preferred embodiment of the present invention a tubular body portion lining assembly adapted for insertion into a tubular body portion of a patient, including a flexible tubular liner including at least one generally circumferentially disposed attachment portion on its outer surface adapted to face the internal walls of the tubular body portion and to attach the liner thereto, and liner placing functionality adapted to place at least a portion of the tubular liner between first and second locations within the tubular body portion.

There is further provided in accordance with yet another preferred embodiment of the present invention a method for treating a patient including providing a tubular liner adapted for insertion into an intestine of a patient, deploying and anchoring the tubular liner within a portion of the intestine exhibiting at least one of a fistula, a perforation, an anastomosa, gastrointestinal bleeding, diverticular disease, diverticulitis, diverticulosis and ulceration.

There is further provided in accordance with still another preferred embodiment of the present invention a method for treating a patient including providing a tubular liner adapted for insertion into an intestine of a patient, detecting at least one location of at least one portion of the intestine exhibiting at least one of a Crohn's disease, colitic, and ulcerative colitis, and deploying and anchoring the tubular liner at the at least one portion of the intestine.

There is yet further provided in accordance with still another preferred embodiment of the present invention a method for treating constipation of a patient including placing a tubular generally liquid impermeable liner at a desired location in a colon of a patient.

There is also provided in accordance with yet another preferred embodiment of the present invention a method for treating diarrhea of a patient including placing a narrowing tubular pathway implant at a desired location in an intestine of a patient.

There is even further provided in accordance with yet another preferred embodiment of the present invention a method for treating obesity of a patient including providing a generally stretchable tubular liner having generally non-stretchable circumferential reinforced portions, placing the tubular liner in a stomach of a patient, and circumferentially anchoring the generally stretchable tubular liner to the stomach along the circumferential reinforced portions.

BRIEF DESCRIPTION OF THE DRAWINGS

The present invention will be understood and appreciated more fully from the following detailed description, taken in conjunction with the drawings in which:

FIGS. 1A, 1B, 1C and 1D are respective pictorial, exploded, side and front view simplified illustrations of a lining system constructed and operative in accordance with a preferred embodiment of the present invention;

FIGS. 2A and 2B are simplified, partially sectional illustrations of the lining system of FIGS. 1A-1D, with respective sections taken along lines IIA and IIB in FIG. 1B;

FIGS. 3A and 3B are respective simplified pictorial and sectional illustrations of an anchoring assembly for use with the lining system of FIGS. 1A-2B, in respective extended and retracted orientations;

FIGS. 4A, 4B, 4C, 4D, 4E, 4F, 4G, 4H, 4I, 4J, 4K, 4L and 4M are simplified, partially sectional illustrations of the operation of the apparatus of FIGS. 1A-3B;

FIGS. 11A, 11B, 11C and 11D are respective simplified pictorial and sectional illustrations of an anchors applicator for use with the lining system of FIGS. 1A-2B and portions thereof;

FIGS. 14A, 14B, 14C, 14D and 14E are simplified sectional illustrations of a tubular liner forming part of the lining system of FIGS. 1A-2B, located within a stomach of a patient.

DETAILED DESCRIPTION OF PREFERRED EMBODIMENTS

The terms "endoscope" and "endoscopy" are used throughout in a manner somewhat broader than their customary meaning and refer to apparatus and methods which operate within body cavities, passageways and the like, such as, for example, the small intestine, the large intestine, arteries and veins. Although these terms normally refer to visual inspection, as used herein they are not limited to applications which employ visual inspection and refer as well to apparatus, systems and methods which need not necessarily involve visual inspection.

The term "forward" refers to the remote end of an endoscope, accessory or tool furthest from the operator or to a direction facing such remote end.

The term "rearward" refers to the end portion of an endoscope, accessory or tool closest to the operator, typically outside an organ or body portion of interest or to a direction facing such end portion.

Figure 1A:
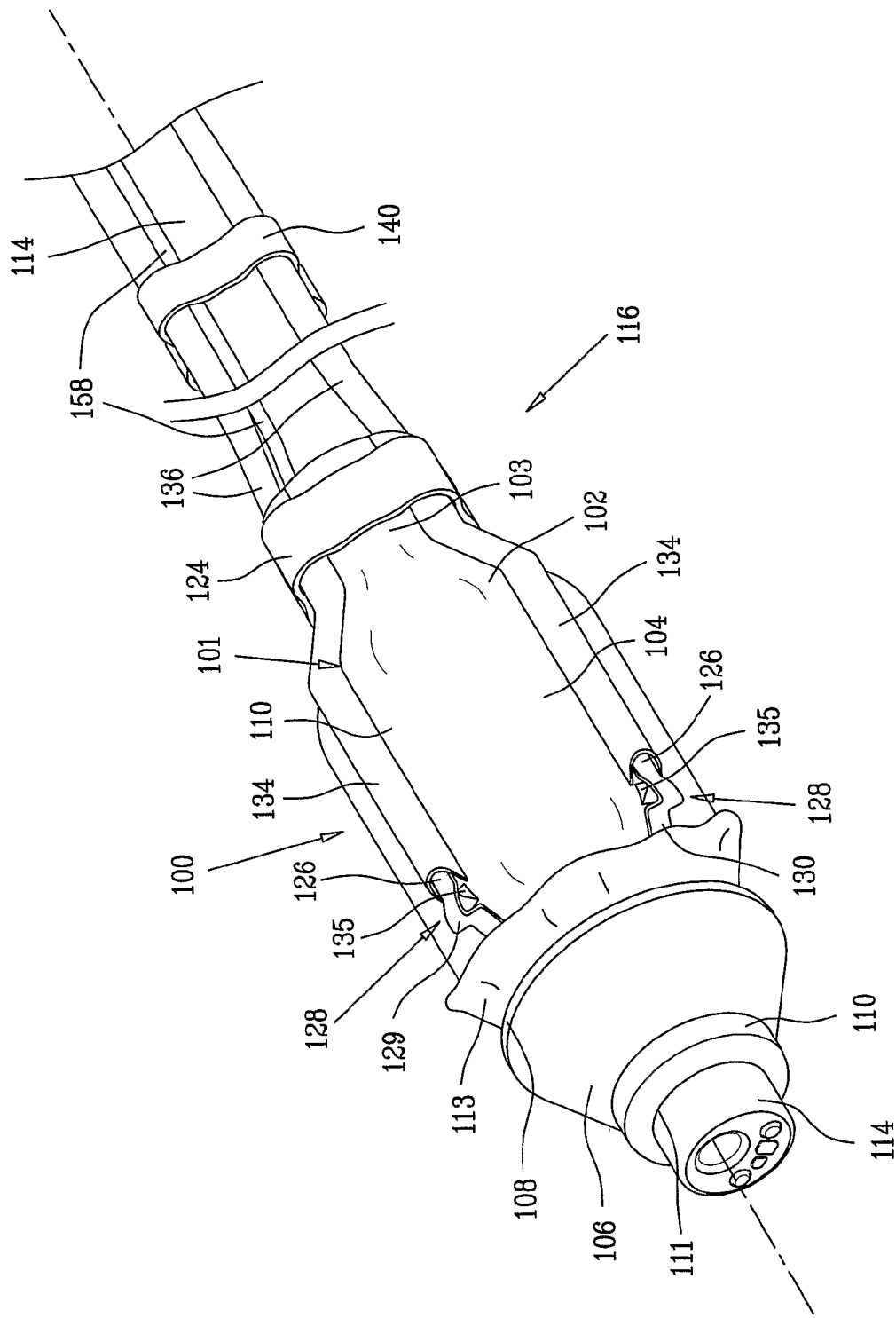

Reference is now made to FIGS. 1A, 1B, 1C, 1D, 2A and 2B, which illustrate a lining assembly 100 constructed and operative in accordance with a preferred embodiment of the present invention. Preferably, lining assembly 100 comprises a generally cylindrical bunched liner container 101, which includes a bunched liner container body 102 having a cylindrical forward portion and a generally tapered rearward portion (FIGS. 1A, 2A and 2B). Bunched liner container 101 further includes a cylindrical bunched liner container mounting portion 103 which protrudes rearwardly from the rearward circumference of bunched liner container body 102, and a generally cylindrical bunched liner container housing portion 104 which protrudes forwardly from the forward circumference of bunched liner container body 102. Bunched liner container housing portion 104 includes a generally tapered circumferential cutting surface 105 at its forward portion. Preferably, bunched liner container mounting portion 103 and bunched liner container housing portion 104 are formed integrally with bunched liner container body 102.

Lining assembly 100 further comprises at its forward portion a cylindrical and generally tapered cutter cap 106 having a circumferential cutter 107 protruding rearwardly therefrom and a circumferential protective edge 108 facing rearwardly at its outer perimeter. Preferably, the slope of the tapered cutter cap 106 is similar to the slope of the tapered circumferential cutting surface 105 of bunched liner container 101. Cutter cap 106 further includes a cylindrical cutter cap mounting portion 109 (FIGS. 2A and 2B).

In accordance with a preferred embodiment of the present invention, lining assembly 100 comprises a tubular sleeve 110 which supports both bunched liner container 101 and cutter cap 106. Preferably, tubular sleeve 110 has a central lumen 111 extending along its length.

Preferably, cutter cap 106 at least partially overlays tubular sleeve 110 at a location adjacent a forward end of tubular sleeve 110, and is fixed thereon by an adhesive, mechanical attachment, or in any other suitable manner. In accordance with a specific embodiment of the present invention, tubular sleeve 110 is insert-molded with cutter cap 106 as well known in the art, such that cutter cap mounting portion 109 is located within a forward portion of tubular sleeve 110 (FIGS. 2A and 2B).

Preferably, bunched liner container 101 at least partially overlays a rearward portion of tubular sleeve 110, and is fixed thereon by an adhesive, mechanical attachment, or in any other suitable manner (FIGS. 2A and 2B). In accordance with a specific embodiment of the present invention, tubular sleeve 110 is insert-molded with bunched liner container 101 as well known in the art, such that bunched liner container mounting portion 103 is located within a rearward portion of tubular sleeve 110 (not shown).

It is appreciated that alternatively to tubular sleeve 110, another longitudinal element may be utilized to support bunched liner container 101 and cutter cap 106.

A tubular liner 112 is preferably bunched within the housing portion 104 of bunched liner container 101, with a leading end of liner 113 being disposed intermediate bunched liner container 101 and cutter cap 106.

In accordance with a preferred embodiment of the present invention, lining assembly 100 is mounted on a long and flexible inserter such as an endoscope 114, thereby forming a lining system 116. Preferably, lining assembly 100 is placed over part of the forward portion of endoscope 114 by inserting the forward portion of endoscope 114 through the central lumen 111 of tubular sleeve 110.

Preferably, endoscope 114 is a conventional flexible endoscope such as a VSB-3430K video enteroscope or a EC-3470LK video colonoscope which are commercially available from Pentax Europe GmbH, 104 Julius-Vosseler St., 22527 Hamburg, Germany. Endoscope 114 preferably includes at least one illumination source 117, a CCD camera 118 or an alternative detector, a rinsing and insufflation channel 119, and an instrument channel 120 for passage therethrough of variety of diagnostic and therapeutic accessories, such as an ultrasonic probe, a polyp cauterizer, snares, or biopsy forceps. Endoscope 114 operates in conjugation with an endoscopy console (not shown), as well known in the art, such as a console including a EPK-1000 video processor and a SONY LMD-2140MD medical grade flat panel LCD monitor, all commercially available from Pentax Europe GmbH, 104 Julius-Vosseler St., 22527 Hamburg, Germany.

It is appreciated that bunched liner container 101 and/or cutter cap 106 may be formed of a rigid material, for example a metal or a hard polymeric material such as polycarbonate or DELRIN®. Alternatively, bunched liner container 101 and/or cutter cap 106 may be formed of a relatively flexible material, such as thin TEFLON®, silicone, polypropylene or polyurethane, thereby providing flexibility of lining system 116, and compliance of lining assembly 100 with bending of the forward portion of endoscope 114.

It is appreciated that tubular sleeve 110 may be constructed of a flexible and stretchable material, such as flexible and stretchable silicon, latex or rubber, thereby enabling it to conform to bending of endoscope 114. It is further appreciated that tubular sleeve 110 preferably has an untensioned inner circumference slightly larger than the cross-sectional circumference of endoscope 114, thereby allowing it to be pulled or pushed and slid over the endoscope 114. Tubular sleeve 110 preferably is elastic, such that it can deform under application of force, and resume its original shape when the deforming force is ceased.

Preferably, a rearward end of lining assembly 100 is attached firmly to endoscope 114 by a mounting band 124 which encircles the bunched liner container mounting portion 103 and the tubular sleeve 110, or in any other suitable manner. Mounting band 124 may be stretchable, or may be a rigid fixating element that relies on the stretchability of tubular sleeve 110 for providing firm attachment of lining assembly 100 to endoscope 114 while not damaging endoscope 114.

As seen in FIGS. 1A-2B, lining assembly 100 comprises four long and relatively flexible leading-end-of-liner positioners 126 which are disposed outwardly of bunched liner container 101 along its length. Leading-end-of-liner positioners 126 traverse the bunched liner container 101, and extend rearwardly therefrom along at least part of endoscope 114. Preferably, each leading-end-of-liner positioner 126 has a positioner leading portion 128 at its forward portion. Positioner leading portions 128 typically comprise a curved contour 129 facing forwardly and an inclined linear end portion 130 protruding therefrom, which is pointing forwardly and radially inwardly towards the forward end of endoscope 114 (FIG. 2A). Preferably, the slope of the linear end portions 130 of positioner leading portions 128 is approximately similar to the slope of the tapered circumferential cutting surface 105 and the tapered cutter cap 106. In the orientation of FIGS. 1A-2B, the positioner leading portions 128 are located intermediate the circumferential cutting surface 105 and the cutter cap 106 (FIG. 2A).

Preferably, four positioner leading portion recesses 132 are formed within the outer surface of circumferential cutting surface 105, behind each linear end portion 130 of positioner leading portions 128. The positioner leading portion recesses 132 are arranged to house the linear end portions 130 of positioner leading portions 128. When the positioner leading portions 128 are pressed against the circumferential cutting surface 105, each linear end portion 130 shelters within the corresponding positioner leading portion recess 132. Preferably, the sum of the thickness of the circumferential cutting surface 105 in the location of a positioner leading portion recess 132 and the thickness of a linear end portion 130 (FIG. 2A) is similar to the thickness of the circumferential cutting surface 105 in a location where there is no recess 132 (FIG. 2B). It is thus appreciated that when positioner leading portions 128 are pressed against circumferential cutting surface 105 and the linear end portions 130 are therefore sheltered within their corresponding positioner leading portion recesses 132, a circumferential cutting surface of uniform thickness is formed.

Preferably, leading-end-of-liner positioners 126 are located within corresponding positioner tubular guiding elements 134, which are connected to bunched liner container 101 by an adhesive or in another suitable manner, or are alternatively formed integrally therewithin. Four positioner guides 135 are located on the outer rearward circumference of circumferential cutting surface 105, in front of the forward opening of each of the positioner tubular guiding elements 134 and beneath the corresponding leading-end-of-liner positioners 126.

The four leading-end-of-liner positioners 126 are further located within four corresponding positioner tubes 136, which are fixedly attached at their forward ends to the corresponding rearward ends of positioner tubular guiding elements 134 in any suitable manner, such as an adhesive. Positioner tubes 136 are preferably positioned along the endoscope 114, and may be attached to the endoscope 114 at multiple locations along its length in any suitable manner such as by medical adhesive tape or flexible bands 140. Rearward ends of positioner tubes 136 are typically open to enable rearward ends of leading-end-of-liner positioners 126 to extend therefrom outside of a patient's body, thereby enabling advancement or retraction of leading-end-of-liner positioners 126 along and relative to positioner tubes 136 and positioner tubular guiding elements 134 by an operator (not shown).

It is appreciated that the rearward ends of positioner tubular guiding elements 134 are fixed in position relative to endoscope 114, bunched liner container 101 and tubular sleeve 110 at the attachment location of mounting band 124.

It is appreciated that a different number of leading-end-of-liner positioners 126 may be employed, implying a corresponding number of positioner leading portions 128, positioner leading portion recesses 132, positioner tubular guiding elements 134, positioner guides 135 and positioner tubes 136. In accordance with a specific embodiment of the present invention, two leading-end-of-liner positioners 126 are employed. In accordance with another specific embodiment of the present invention, three leading-end-of-liner positioners 126 are employed.

Figure 1B:
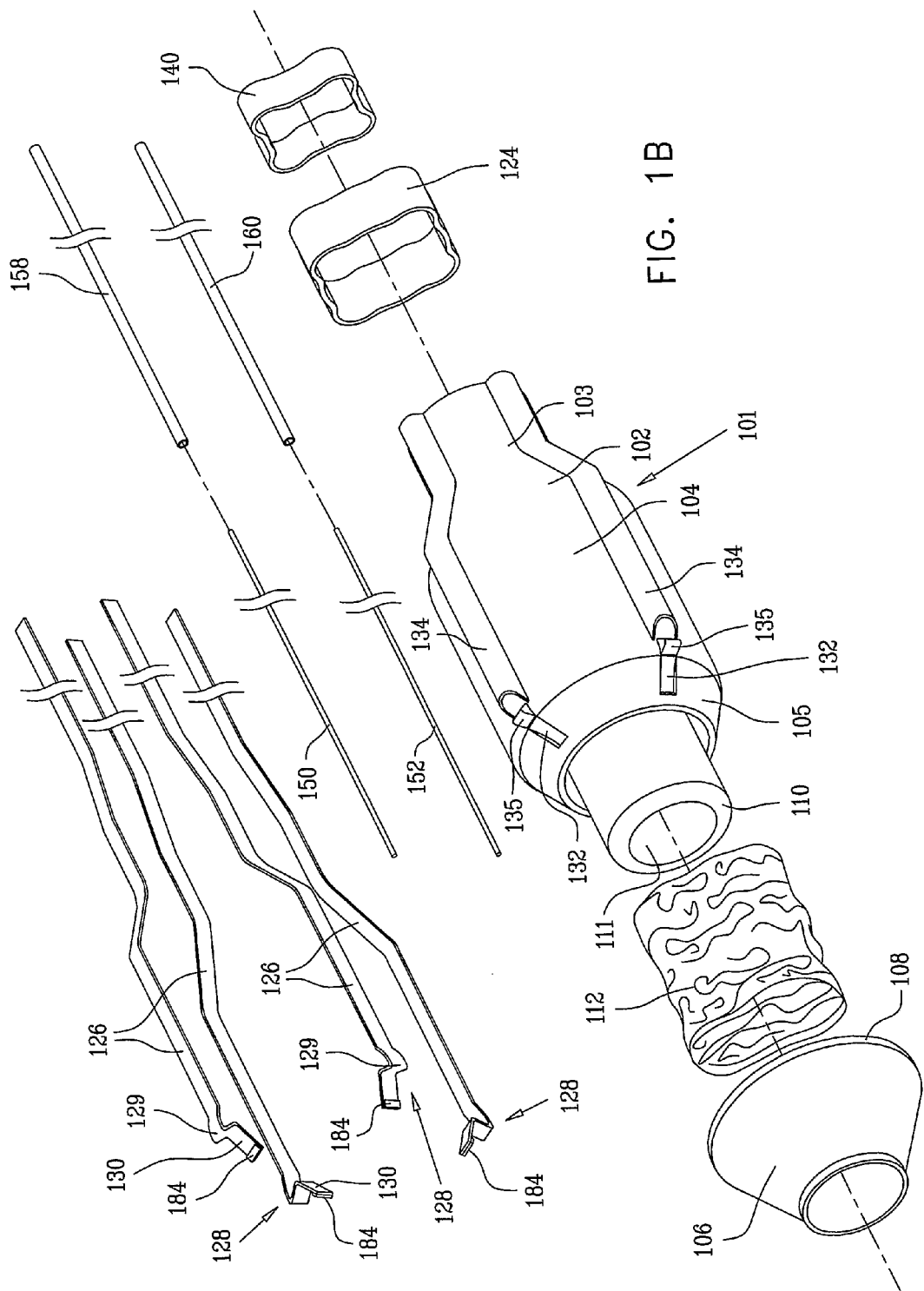
Figure 1C:
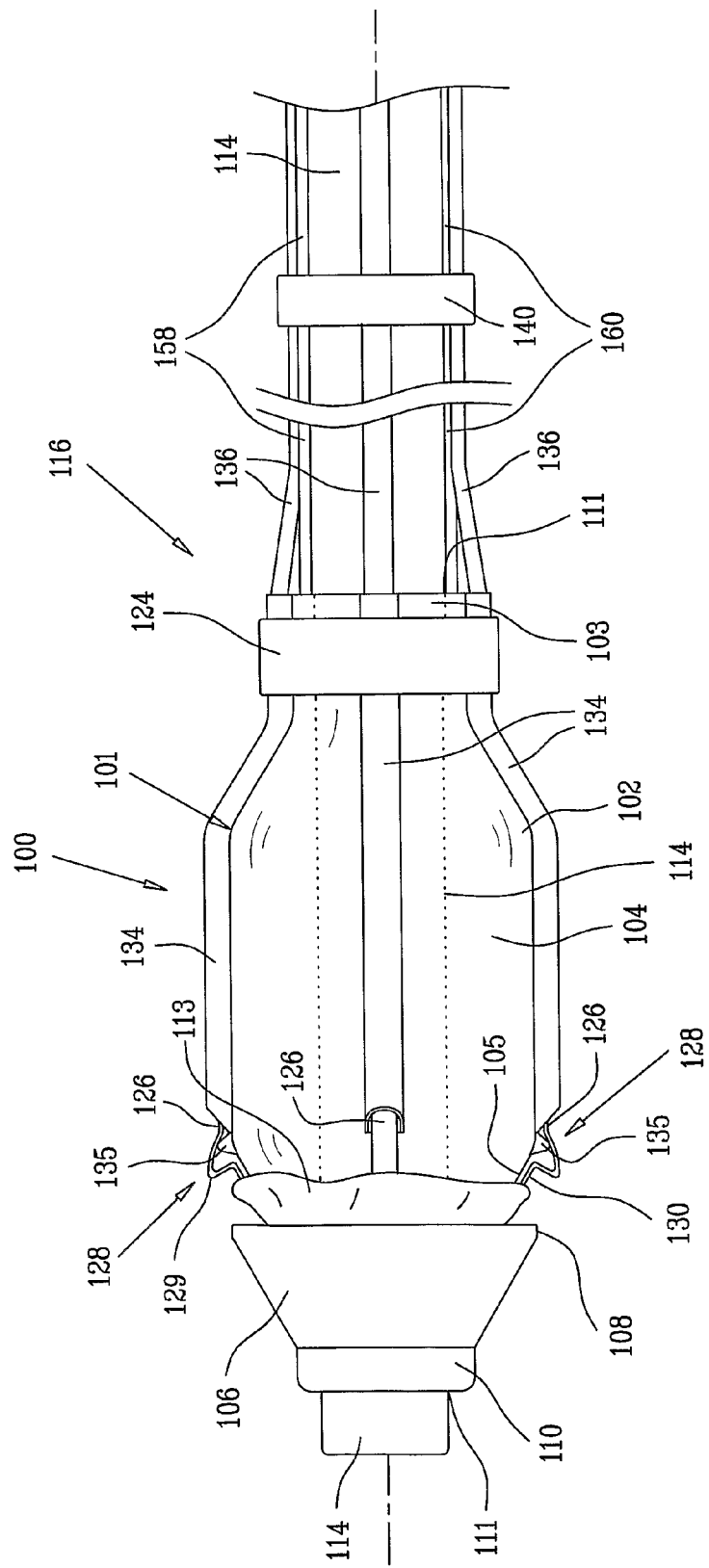

Preferably, leading-end-of-liner positioners 126 are rigid enough to be advanced forwardly of the forward end of endoscope 114 without collapsing, and yet are flexible enough to be directed radially outwardly by the corresponding positioner guides 135 during such advancement, and to bend when engaging cutter cap 106 during such advancement for releasing the positioner leading portions 128 from their location intermediate the circumferential cutting surface 105 and the cutter cap 106. Leading-end-of-liner positioners 126 may be formed of a flexible plastic or a flexible metal such as nitinol or medical grade stainless steel. Leading-end-of-liner positioners 126 may assume a rectangular cross section as illustrated in FIGS. 1A and 1B, thereby affording higher resistance of leading-end-of-liner positioners 126 to tangential bending while maintaining sufficient flexibility in a radial direction. Alternatively, leading-end-of-liner positioners 126 may assume a different cross sectional shape, such as a circular cross section which may provide compliance of leading-end-of-liner positioners 126 with bending of the endoscope 114 and the mounted lining assembly 100.

Preferably, lining assembly 100 includes two cutter cap tensioning elements 150 and 152 such as flexible metal wires, which are firmly fixed to the rearward end of cutter cap mounting portion 109 at respective tensioning element attachment locations 154 and 156, and are traversing tubular sleeve 110 rearwardly (FIG. 2A). In accordance with a preferred embodiment of the present invention, Cutter cap tensioning elements 150 and 152 are insert-molded with tubular sleeve 110 such that tensioning elements 150 and 152 are located within tubular sleeve 110, as well known in the art. Cutter cap tensioning elements 150 and 152 are further positioned within two corresponding cutter cap tensioning element tubes 158 and 160, having respective tensioning-element-tube forward ends 162 and 164 (FIG. 2A). Tensioning-element-tube forward ends 162 and 164 are preferably fixedly attached to the rearward portion of tubular sleeve 110, within respective tubular recesses 166 and 168 formed therein. It is appreciated that the tensioning-element-tube forward ends 162 and 164 are fixed in position relative to endoscope 114 and bunched liner container 101 at the attachment location of mounting band 124.

Cutter cap tensioning element tubes 158 and 160 are positioned along the endoscope 114, and may be attached to the endoscope 114 at multiple locations along its length in any suitable manner such as medical adhesive tape, and preferably by the flexible bands 140. Rearward ends of tubes 158 and 160 are typically open to enable rearward ends of tensioning elements 150 and 152 to extend therefrom outside of a patient's body, thereby enabling pulling of tensioning elements 150 and 152 along and relative to respective tubes 158 and 160 by an operator (not shown).

Preferably, the tubular liner 112 is bunched within the housing portion 104 of bunched liner container 101, with the leading-end-of-liner 113 located intermediate the circumferential cutting surface 105 of bunched liner container 101 and the cutter cap 106 (FIGS. 2A and 2B). The leading-end-of-liner 113 is attached to all of the positioner leading portions 128 at their linear end portions 130, via corresponding leading-end-of-liner engagers 184, which provide detachable engagement of the leading-end-of-liner 113 with the positioner leading portions 128 at the engagement locations.

Leading-end-of-liner engagers 184 may be formed of a sticky material that is capable of attaching well to liner 112, and yet can be separated from liner 112 under application of moderate pulling or shear forces. Preferably, leading-end-of-liner engagers 184 are capable of engaging and disengaging liner 112 few or even many times without substantially loosing their stickiness. It is appreciated that the leading-end-of-liner engagers 184 remain sticky in an aqueous environment, and are suitable for engaging liner 112 within a living organ such as an intestine, such as during in vivo inspection or treatment. An example of a leading-end-of-liner engager 184 having appropriate stickiness in an aqueous environment is a pad immersed or impregnated with sodium alginate, such as PROTEFIX® sticky pads used for dental applications and commercially available from Dentorient Fuss Ltd., 28 Hagdud Haivri street, Tel Aviv, Israel. Leading-end-of-liner engagers 184 may employ any other suitable mechanism to provide detachable engagement between leading-end-of-liner 113 and positioner leading portions 128, such as mechanical pinching or anchoring of liner 112 to the leading-end-of-liner engagers 184, clamping of liner 112 by leading-end-of-liner engagers 184, or partial vacuum formation between liner 112 and engagers 184.

It is appreciated that during advancement of leading-end-of-liners 126 and thus release of the positioner leading portions 128 with the attached leading-end-of-liner 113 from their position intermediate the circumferential cutting surface 105 and the cutter cap 106, the linear end portions 130 engage and slide against the circumferential protective edge 108 of cutter cap 106, thereby preventing the leading-end-of-liner 113 from pressing against the circumferential cutter 107 and being cut or damaged.

As will be further explained hereinbelow with reference to FIGS. 4A-4M, lining assembly 100 and lining system 116 are operative for insertion into a tubular body portion of a patient, such as an intestine, and for deploying a selectable portion of liner 112 within the tubular body portion of the patient. It is appreciated that lining system 116 including endoscope 114 is operative also for inspection of the tubular body portion of the patient, and for detecting a location for deploying a selectable portion of liner 112 within the tubular body portion of the patient. It is appreciated that the circular cross section and tapered shape of cutter cap 106 allow relatively easy and low-resistance advancement of lining assembly 100 within a tubular organ, such as an intestine. Similarly, the circular cross section and tapered shape of bunched liner container body 102 allow relatively easy and low-resistance retraction of lining assembly 100 within a tubular organ, such as an intestine. It is further appreciated that the maximum cross sectional diameter of lining assembly 100, and typically of housing portion 104 of bunched liner container 101, is suitable for insertion into the tubular organ.

In accordance with an embodiment of the present invention useful for placement of tubular liner in a portion of the small intestine of a patient, the maximum cross sectional diameter of lining assembly 100 and specifically of housing portion 104 is less than 16 millimeters. In accordance with an embodiment of the present invention useful for placement of tubular liner in a portion of the colon of a patient, the maximum cross sectional diameter of lining assembly 100 and specifically of housing portion 104 is larger than 16 millimeters. In accordance with another embodiment of the present invention useful for placement of tubular liner in a portion of the colon of a patient, the maximum cross sectional diameter of lining assembly 100 and specifically of housing portion 104 is larger than 20 millimeters. In accordance with yet another embodiment of the present invention useful for placement of tubular liner in a portion of the colon of a patient, the maximum cross sectional diameter of lining assembly 100 and specifically of housing portion 104 is larger than 30 millimeters.

It is appreciated that a smaller diameter of lining assembly 100 provides easier insertion of lining assembly 100 into the treated tubular organ, whereas a larger diameter of lining assembly 100 and specifically of housing portion 104 provides bunching of a longer and/or wider tubular liner 112.

As will be described hereinbelow with reference to FIG. 4J, cutter cap 106 may retract and engage the circumferential cutting surface 105 of bunched liner container 101, by pulling on the cutter cap tensioning elements 150 and 152 by an operator (not shown). During such engagement, the circumferential cutter 107 presses the liner 112 against circumferential cutting surface 105 and cuts it around its entire circumference, while the leading-end-of-liner engagers 184 are pressed against the cutter cap 106 with the tubular liner 112 intermediate engagers 184 and cutter cap 106, thereby engaging liner 112 and attaching positioner leading portions 128 thereto.

Preferably, circumferential cutter 107 is located radially outwardly with respect to the leading-end-of-liner engagers 184, such that it cuts the tubular liner 112 outwardly of engagers 184, resulting in attachment of liner 112 to the positioner leading portions 128 via engagers 184 following the cutting of liner 112.

Reference is now made to FIGS. 3A and 3B, which are respective simplified pictorial and sectional illustrations of an anchoring assembly 200 for use with the lining system of FIGS. 1A-2B, constructed and operative in accordance with a preferred embodiment of the present invention. Anchoring assembly 200 preferably includes an anchor-arms-manipulator 202 such as a flexible metal wire, which is adapted to travel through an anchor-arms-manipulator-leading-element 204, which preferably comprises a long and flexible tube. Anchor-arms-manipulator 202 is connected at its forward end 205 to a plurality of prestressed anchor arms 206. When not otherwise restrained, anchor arms 206 extend perpendicularly to anchor-arms-manipulator 202 and are spaced from each other radially, either uniformly or non-uniformly. Anchor arms 206 are preferably flexible enough to be bent over anchor-arms-manipulator 202 for insertion into anchor-arms-manipulator-leading-element 204 (FIG. 3B) and passage therethrough, and are elastic enough to resume their perpendicular orientation when extracted from anchor-arms-manipulator-leading-element 204 (FIG. 3A).

Anchor arms 206 may be formed of any suitable material, such as flexible, medical grade, metal wires, or flexible plastic rods. Anchor arms 206 may be firmly connected to the forward end 205 of anchor-arms-manipulator 202 in any suitable manner, such as welding, preferably laser welding, if both anchor-arms-manipulator 202 and anchor arms 206 are made of appropriate metals, or gluing. Alternatively, anchor arms 206 may be formed integrally with anchor-arms-manipulator 202.

It is appreciated that anchoring assembly 200 and particularly anchor-arms-manipulator 202 and anchor-arms-manipulator-leading-element 204 are configured to pass through the instrument channel 120 of endoscope 114. Typically, anchoring assembly 200 has a maximum cross sectional diameter of 2-4 millimeters.

As illustrated in FIGS. 3A and 3B, an individual anchor 210 is detachably positioned at the outer end of each anchor arm 206. Individual anchor 210 preferably includes an individual-anchor head 212 adapted to anchor in a tissue of an organ such as the intestine or the stomach, an individual-anchor body 214, and an individual-anchor rear portion 216 having an anchor rear portion recess 218 to which the outer end of anchor arm 206 is detachably retained in any appropriate manner, such as by moderate mechanical pressure or by using a weak adhesive 220. Preferably, individual-anchor rear portion 216 further includes opposing anchor transversal recesses or a circumferential recess 222, adapted for grabbing individual anchor 210 by an appropriate standard or customized tool such as biopsy forceps, specialized forceps or snares, for pulling individual anchor 210 and removing it from an anchored tissue. Individual-anchor head 212 together with individual-anchor body 214 may have an arrow-like shape, with individual-anchor head 212 having a conical shape with a sharp end, suitable for pinching, penetrating and passing through tubular liner 112 and penetrating at least partially through a tissue of an organ such as the intestine or the stomach of a patient.

Preferably, each of anchor arms 206 has a different length, such that when being located together with individual anchors 210 within anchor-arms-manipulator-leading-element 204 (FIG. 3B) there is no overlap or contact between individual anchors 210.

It is appreciated that when anchoring assembly 200 is used within a tubular body portion such as the intestine, anchor arms 206 are long enough to allow engagement of individual anchors 210 with the internal walls of the tubular body portion when extracted from anchor-arms-manipulator-leading-element 204. It is further appreciated that the length and flexibility of arms 206 enable penetration of individual-anchor heads 212 at least partially through the tissue of the tubular body portion, when arms 206 are forced to perpendicular orientation by anchor-arms-manipulator 202, while not over-pressing the walls of the tubular body portion, so that the individual-anchor rear portions 216 do not penetrate the walls of the tubular body portion.

It is appreciated that any number of anchor arms 206 and corresponding individual anchors 210 may be employed. The number of anchor arms 206 and corresponding individual anchors 210 may be even or odd. A single individual anchor 210 may be employed, in which case two or more anchor arms 206 may be utilized, one of which being attached to the single individual anchor 210 and the other arms 206 not loaded with individual anchors, but rather have a spherical or rounded outer end (not shown) to allow application of counter-force against the walls of the tubular body portion during anchoring, without damaging the tubular body portion. It is further appreciated that the anchoring functionality of anchoring assembly 200 is adapted for simultaneous anchoring of a multiplicity of individual anchors within a tubular body portion of a patient, as will be describe in details hereinbelow with reference to FIGS. 4C-4G.

A rearward end of anchor-arms-manipulator-leading-element 204 is typically open to enable rearward end of anchorarms-manipulator 202 to extend therefrom outside of a patient's body, thereby enabling pulling and pushing of anchor-arms-manipulator 202 with anchor arms 206 along and relative to anchor-arms-manipulator-leading-element 204 by an operator (not shown), and thus enabling extraction of anchor arms 206 from anchor-arms-manipulator-leading-element 204 and reinsertion thereof. Extraction of anchor arms 206 from anchor-arms-manipulator-leading-element 204 and reinsertion thereof is useful for example during in vivo treatment of a tubular body portion such as the intestine in accordance with the present invention, as will be describe in details hereinbelow with reference to FIGS. 4C-4G.

Reference is now made to FIGS. 4A-4M, which are simplified, partially sectional illustrations of a mode of operation of the apparatus of FIGS. 1A-3B.

Figure 4A:
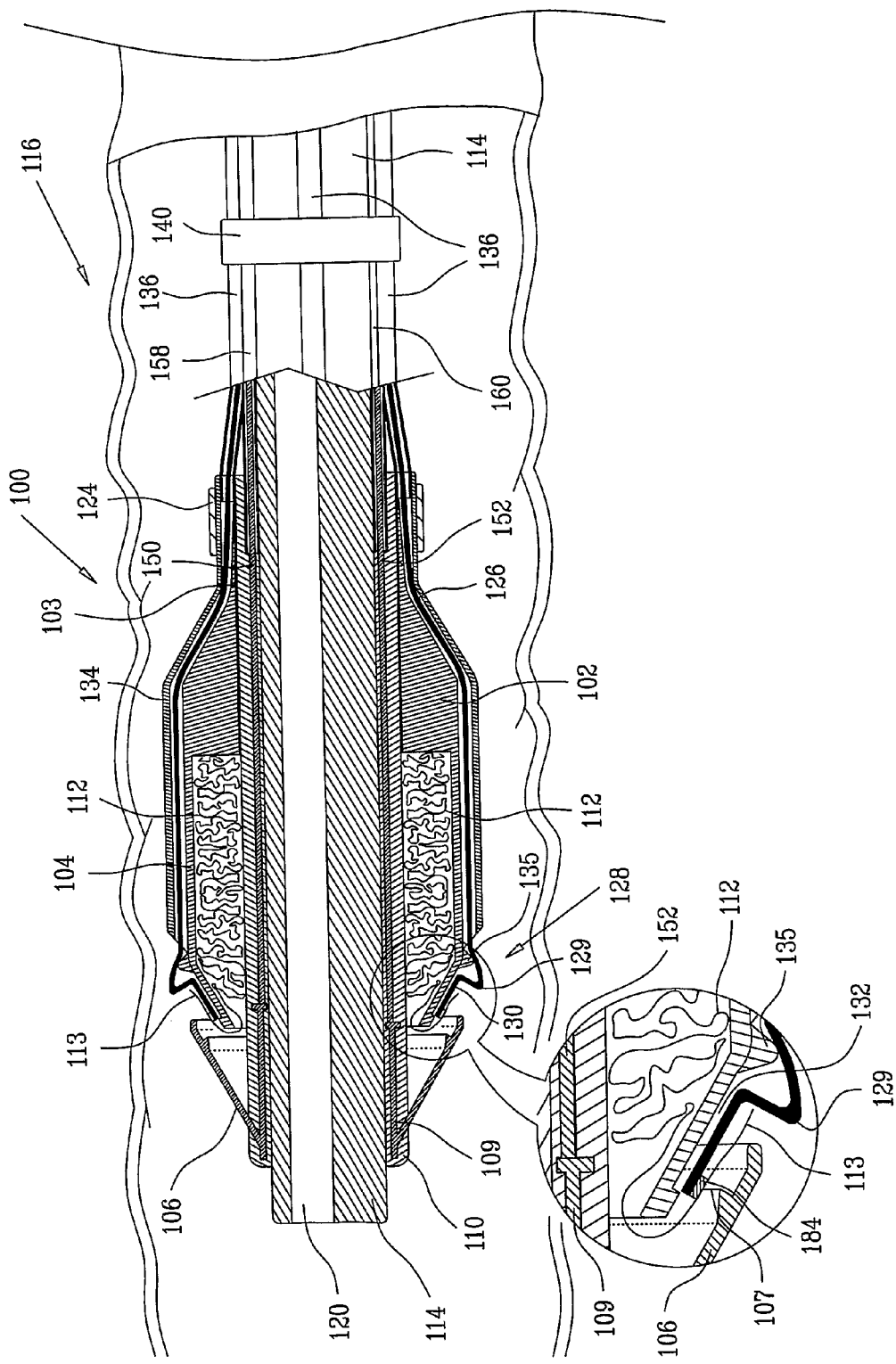

FIG. 4A illustrates the lining system 116 of FIGS. 1A-2B located within the intestine of a patient, at a liner deployment location/region. The liner deployment location/region may be a predetermined location/region, such as the duodenum, the rectum, the terminal ileum, the ileo-cecal valve, the pylorus, the descending colon or the transversal colon of a patient. Alternatively, the liner deployment location/region may be inspected, detected and determined in an endoscopy procedure, as may be performed by lining system 116 including endoscope 114. It is appreciated that the liner deployment location/region need not be the intestine of a patient, and can alternatively be the gastro-esophageal junction, the pylorus, the esophagus or the stomach of a patient, or a tubular body portion which is not part of the gastrointestinal tract, such as an artery, a vein, a trachea or a bronchus.

Figure 4B:
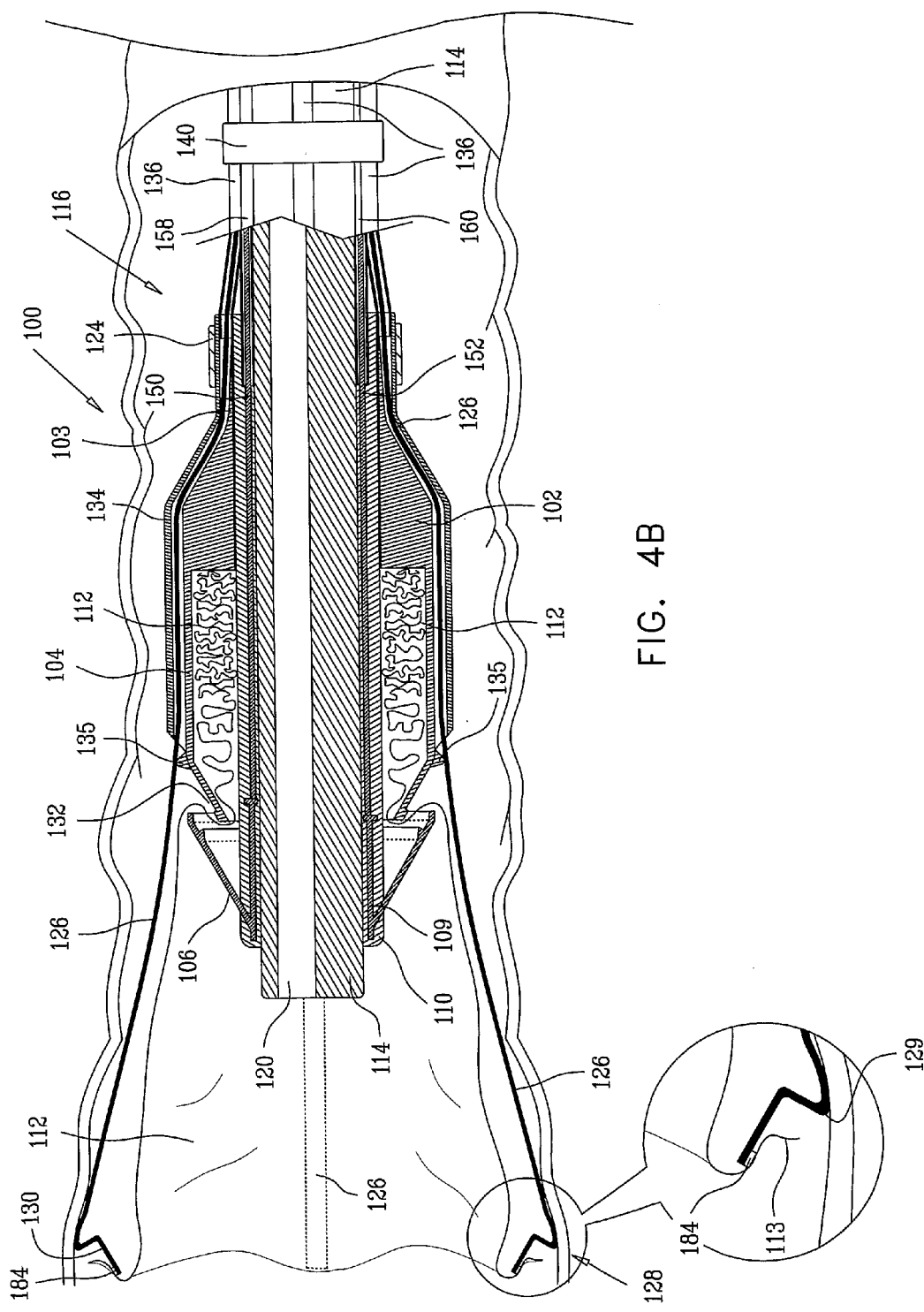

FIG. 4B illustrates leading-end-of-liner positioners 126 being advanced forwardly of the forward end of endoscope 114 with the leading-end-of-liner 113 being attached thereto by leading-end-of-liner-engagers 184, thereby positioning the leading-end-of-liner 113 and the positioner leading portions 128 of leading-end-of-liner positioners 126 forwardly of the forward end of endoscope 114. As seen in FIG. 4B, positioner guides 135 guide the leading-end-of-liner positioners 126 outwardly, preferably to engage the internal walls of the intestine.

Figure 4C:
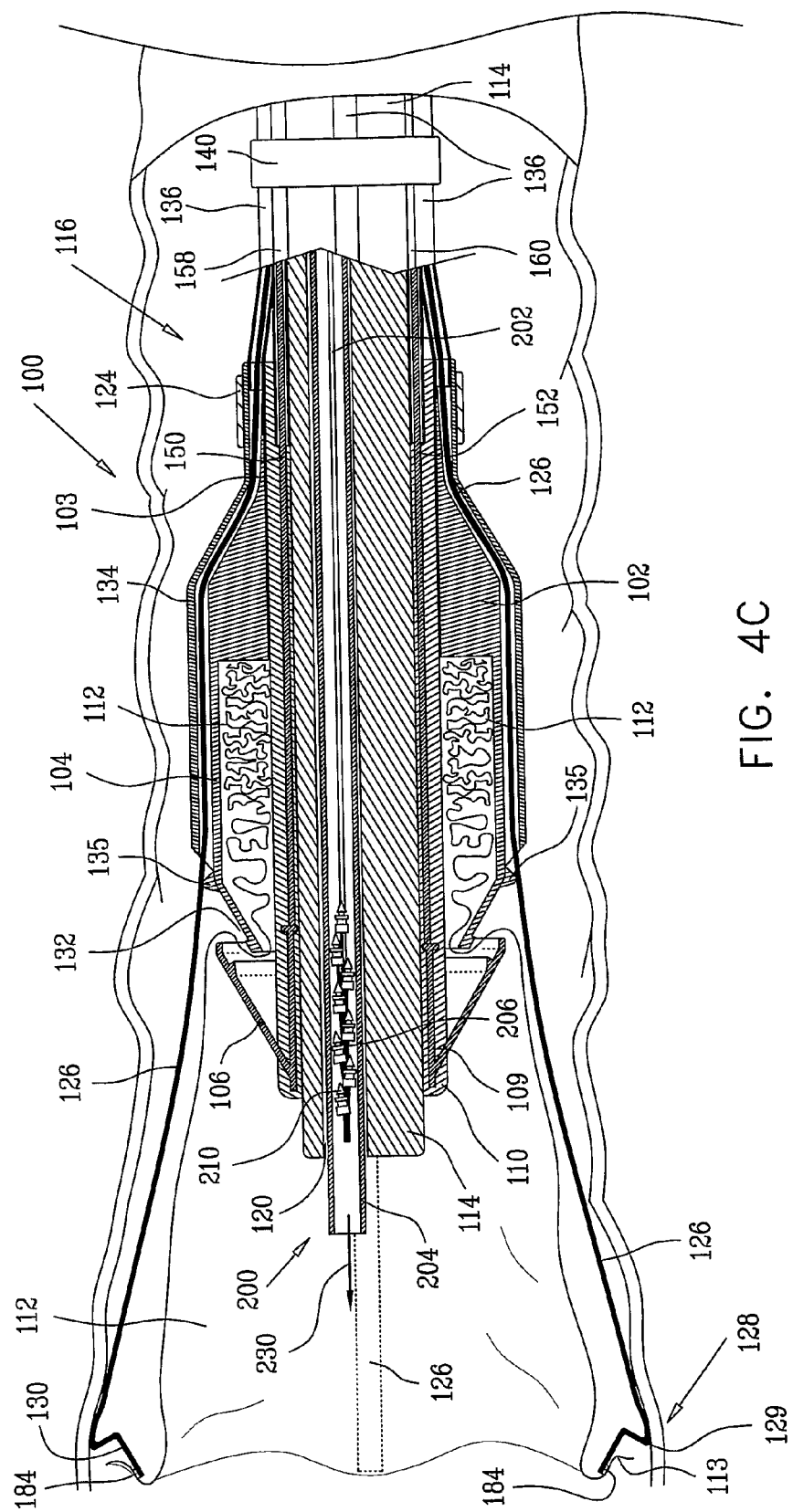

FIG. 4C illustrates advancement of the anchoring assembly 200 through the instrument channel 120 of endoscope 114, with the individual anchors 210 attached to anchor arms 206 and located within the anchor-arms-manipulator-leading-element 204, until the anchor-arms-manipulator-leading-element 204 is located forward of the forward end of endoscope 114, as can be visualized by CCD 118. As denoted in FIG. 4C by arrow 230, once anchor-arms-manipulator-leading-element 204 is located forward of the forward end of endoscope 114, anchor arms 206 are advanced forward along anchor-arms-manipulator-leading-element 204, by an operator pushing anchor-arms-manipulator 202 through anchor-arms-manipulator-leading-element 204 at its rearward end, outside of the patient's body (not shown).

Figure 4D:
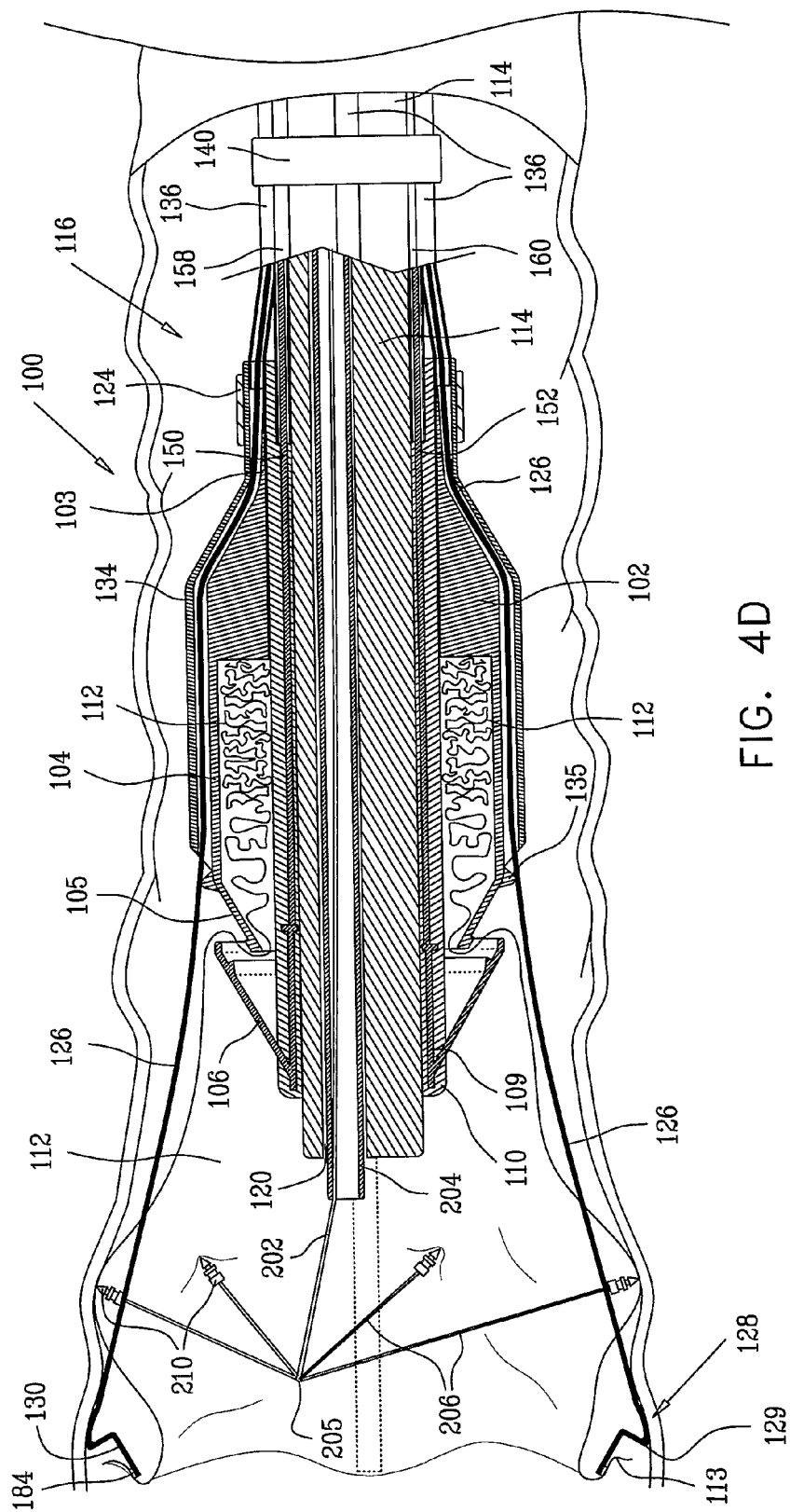

FIG. 4D illustrates anchor arms 206 being released from anchor-arms-manipulator-leading-element 204 and engaging the end portion of tubular liner 112 to press it against the internal walls of the intestine. As seen in FIG. 4D, the anchor-arms-manipulator 202 preferably is bent and forward end 205 thereof at which it is attached to arms 206 is off-center with respect to the longitudinal axis of instrument channel 120, due to the different length of each of anchor arms 206.

Figure 4E:
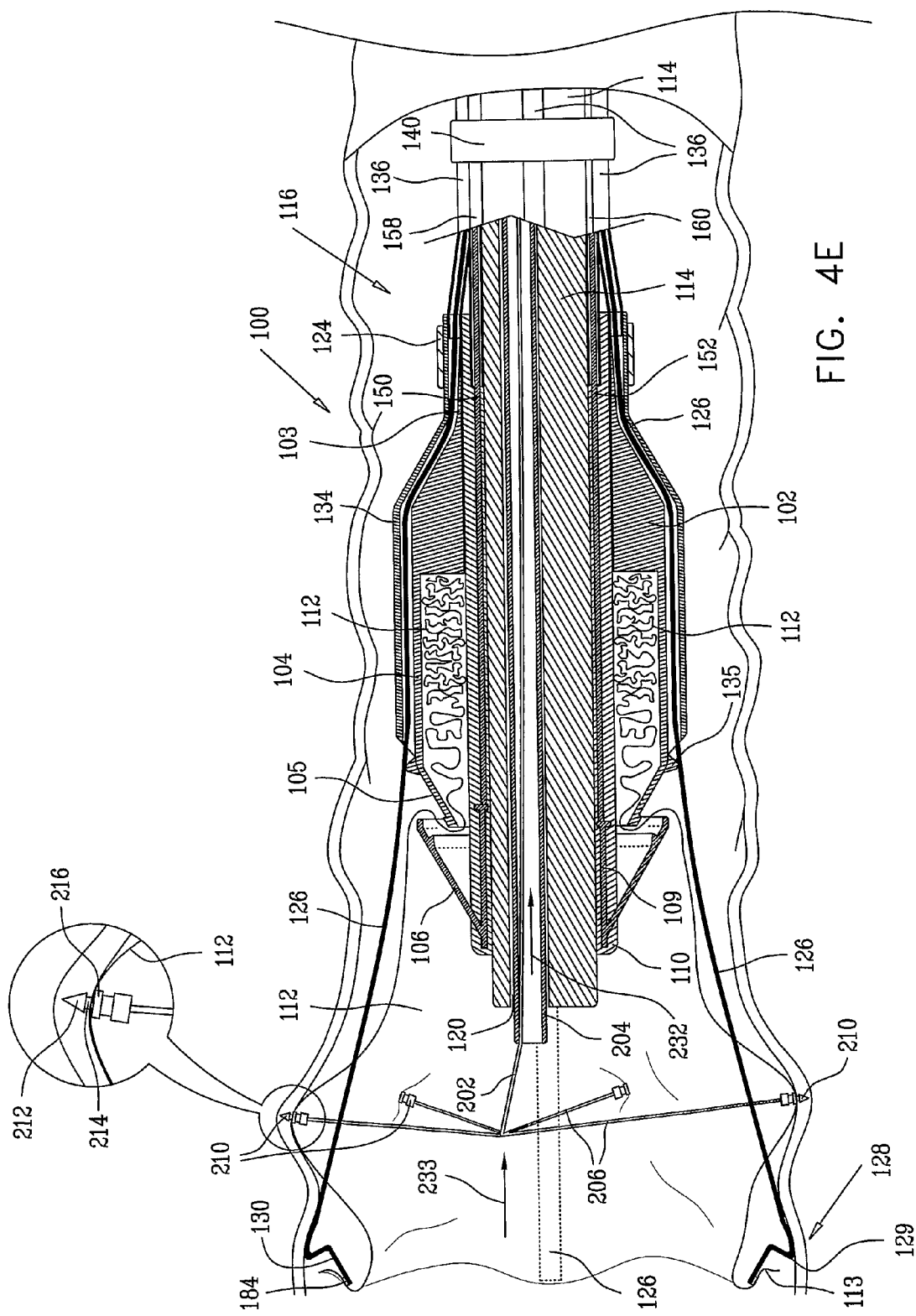

FIG. 4E illustrates anchoring of the end portion of tubular liner 112 to the intestine at a first anchoring location along its length, by the individual anchors 210. As seen in FIG. 4E, anchor-arms-manipulator 202 is pulled within anchor-arms-manipulator-leading-element 204 in the direction denoted by arrow 232, forcing arms 206 rearwardly as denoted by arrow 233, to a generally perpendicular orientation with respect to the intestine. The forces of anchor arms 206 pressing against the liner 112 and the intestinal walls cause anchor heads 212 of individual anchors 210 to penetrate through the tubular liner 112 and penetrate partially through the intestinal tissue. The individual-anchor rear portions 216 which have blunt front ends cannot penetrate the liner 112 and the intestinal walls, resulting in attachment of liner 112 to the intestinal walls by individual anchors 210. It is appreciated that due to the elasticity of the intestinal tissue and preferably of the liner 112, the penetration hole made by individual-anchor head 212 in the liner 112 and the intestinal tissue is partially closed and both liner 112 and the intestinal tissue are fixedly and tightly encircling the individual-anchor body 214, with individual-anchor head 212 being located within the intestinal tissue, and individual-anchor rear portion 216 pressing liner 112 against the internal wall of the intestine at the anchoring location. Preferably, as seen in FIG. 4E, individual anchors 210 secure liner 112 to the intestine at multiple anchoring locations.

Figure 4F:
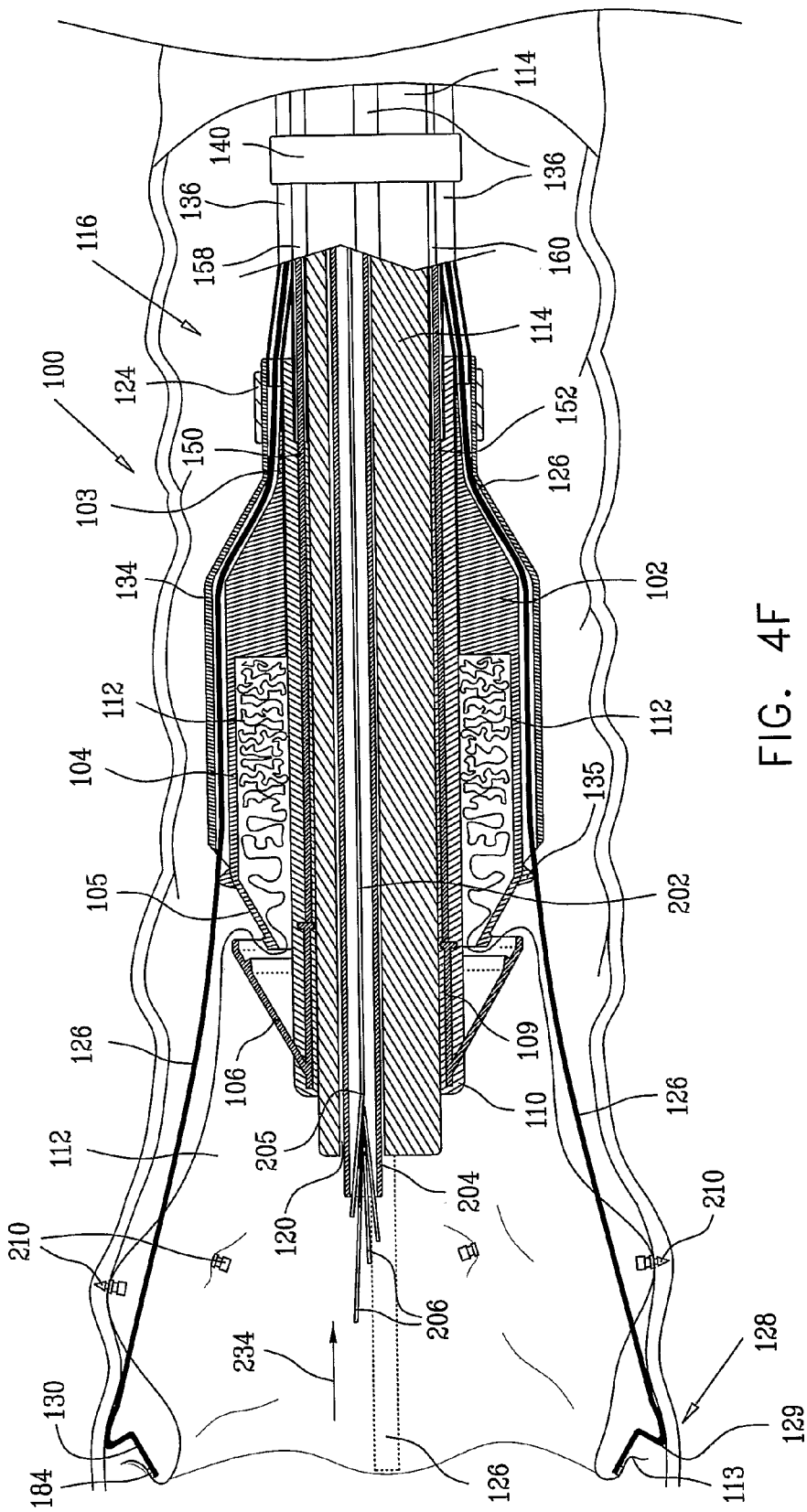
Figure 4G:
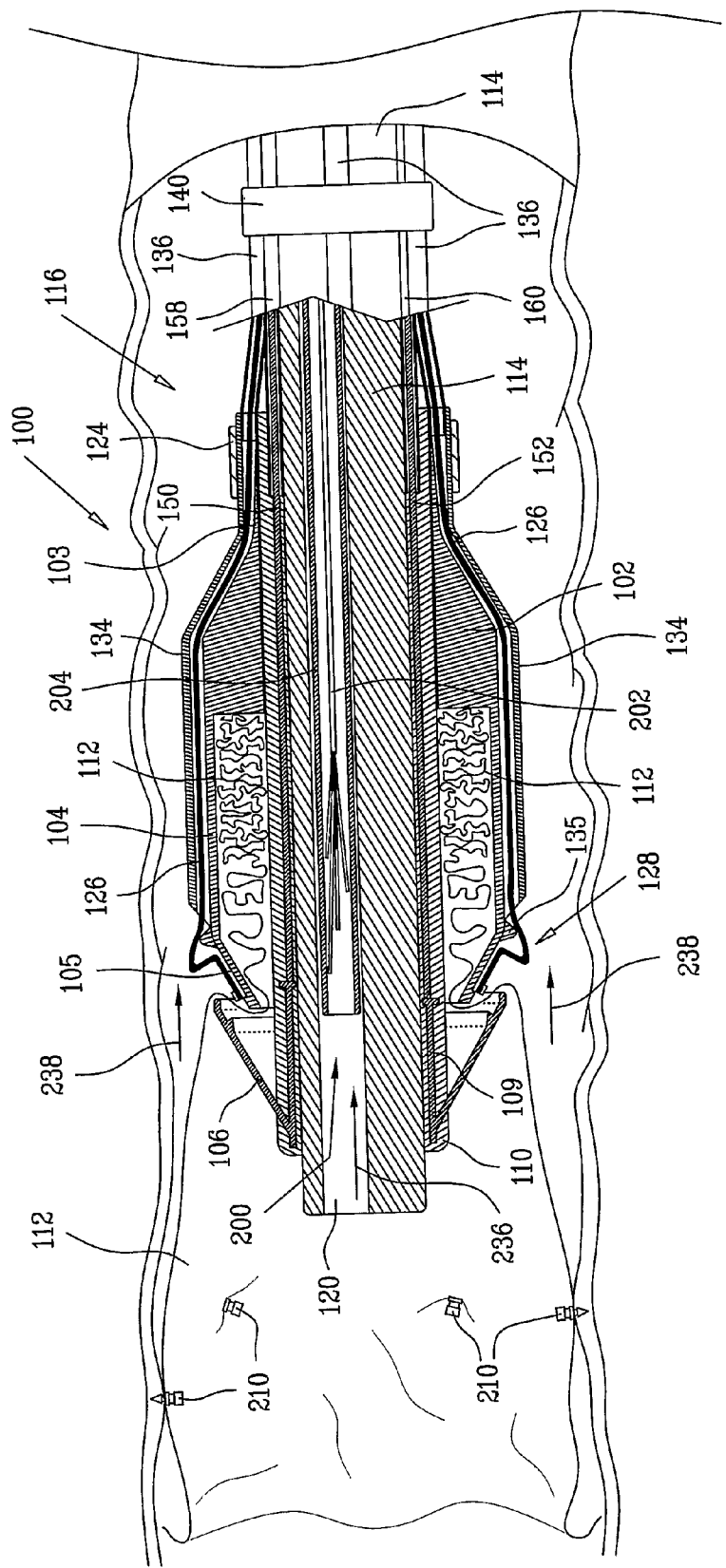
Figure 41:
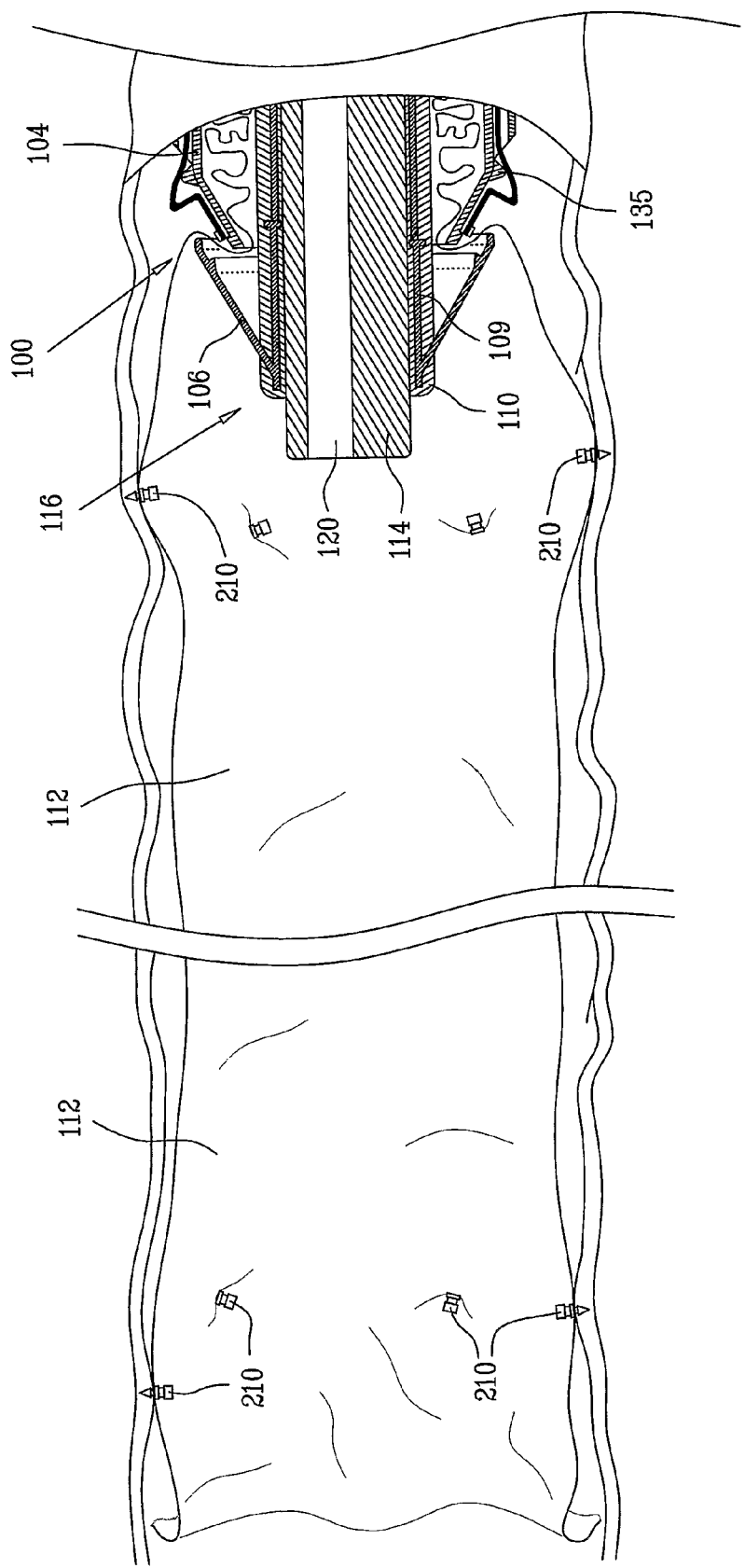

FIG. 4F illustrates disengagement of anchor arms 206 from the anchored individual anchors 210 by pulling on anchor-arms-manipulator 202 in a direction denoted by arrow 234. FIG. 4G illustrates further retraction of anchor arms 206 into anchor-arms-manipulator-leading-elements 204, and removal of anchoring assembly 200 from the instrument channel 120 of endoscope 114, as denoted by arrow 236. It is appreciated that following removal of anchoring assembly 200 from instrument channel 120, another anchoring assembly may be inserted into the instrument channel 120 and additional individual anchors may be deployed by repeating the operation of the anchoring assembly as described hereinabove with reference to FIGS. 4C-4G.

It is appreciated that anchoring assemblies having equal or different numbers of individual anchors may be applied sequentially as needed, in the same anchoring location or in various anchoring locations. It is further appreciated that the individual anchors 210 may be deployed in any appropriate distance from the leading-end-of-liner 113, for example very close to the leading-end-of-liner 113 or further away from it. In accordance with a specific embodiment of the present invention, the individual anchors 210 are located in a distance of 5 to 10 millimeters from the leading-end-of-liner 113. In accordance with another specific embodiment of the present invention, the individual anchors 210 are located in a distance of 10 to 25 millimeters from the leading-end-of-liner 113. In accordance with yet another specific embodiment of the present invention, the individual anchors 210 are located in a distance of 25 to 100 millimeters from the leading-end-of-liner 113.

As further illustrated in FIG. 4G, leading-end-of-liner positioners 126 are withdrawn rearwardly in a direction denoted by arrows 238, back to their position within positioner tubular guiding elements 134, with positioner leading portions 128 located intermediate the circumferential cutting surface 105 and the cutter cap 106. Liner 112 remains anchored to the intestinal wall at the first anchoring location.

FIG. 4H illustrates rearward movement of lining system 116, away from the first anchoring location within the intestine, as denoted by arrow 240. Consequentially, a portion of tubular liner 112 is pulled out of the housing portion 104 of bunched liner container 101, spread and deployed along the internal walls of the intestine to a selectable length. As illustrated in FIG. 4H, following the deployment of a selectable portion of liner 112, lining system 116 is positioned at a second anchoring location within the intestine. In accordance with a preferred embodiment of the present invention, liner 112 is generally transparent, allowing inspection of the intestine during the withdrawal of lining system 116.

Alternatively to such rearward movement, lining system 116 may be advanced forwardly away from the first anchoring location within the intestine. It is appreciated that during such advancement of lining system 116 and deployment of a portion of liner 112, the intestine may be inspected by endoscope 114, and treated or diagnosed utilizing any appropriate standard accessory through the instrument channel 120 of endoscope 114 forwardly of lining system 116 and of the first anchoring location, such as taking a biopsy, removing polyps, or dilating a stricture. It is appreciated that inspection of the intestine by endoscope 114 during deployment of a portion of liner 112 may be useful for determining the region and length of the portion of the tubular liner 112 to be deployed.

FIG. 4I illustrates the liner 112 being anchored at the second anchoring location, by utilizing another anchoring assembly 200 as described hereinabove with reference to FIGS. 4C-4G. It is appreciated that the number of anchors utilized at the second anchoring location may be different from the number of anchors utilized at the first anchoring location. For example, a liner that is deployed in a portion of the intestine for preventing contact of food with that portion, may be anchored with many anchors at the liner end portion which is upstream in terms of food flow, thereby providing tight and continuous contact between the liner and the intestine and preventing food penetration therebetween, while being anchored with less anchors at the liner end portion which is downstream in terms of food flow, thereby allowing mucosal fluids to drain and flow downstream through openings between the liner and the intestine.

Figure 4J:
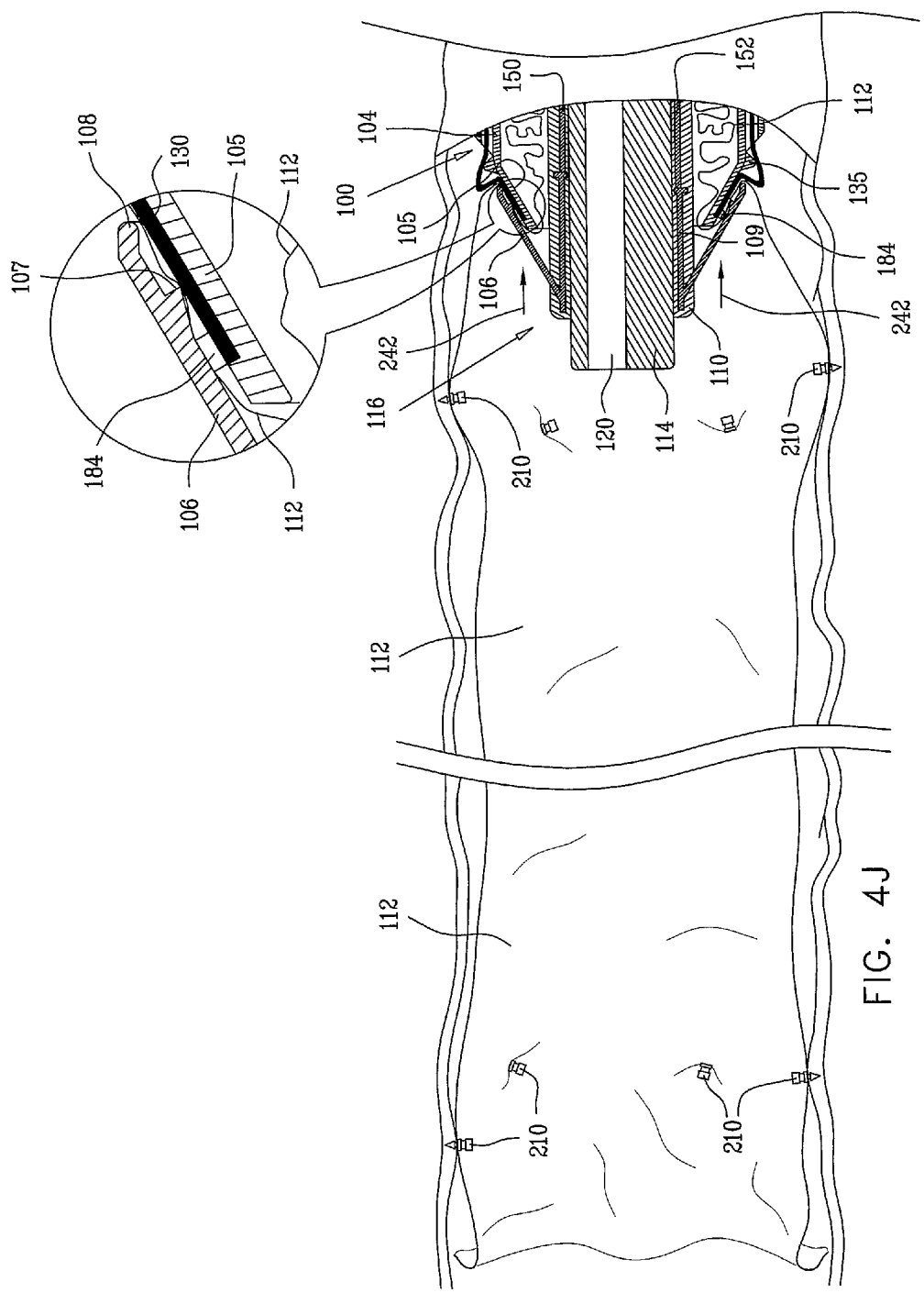

Following anchoring at the second anchoring location, tubular liner 112 is cut peripherally by pushing circumferential cutter 107 against circumferential cutting surface 105 as illustrated in FIG. 4J, by pulling on cutter cap tensioning elements 150 and 152 in a direction denoted by arrows 242, thereby forcing the circumferential cutter 107 of cutter cap 106 into circumferential engagement with cutting surface 105. As seen in FIG. 4J, as cutter cap 106 comes into mechanical contact with the circumferential cutting surface 105, the leading-end-of-liner engagers 184 are pressed against liner 112 and are detachably engaged therewith.

Figure 4K:
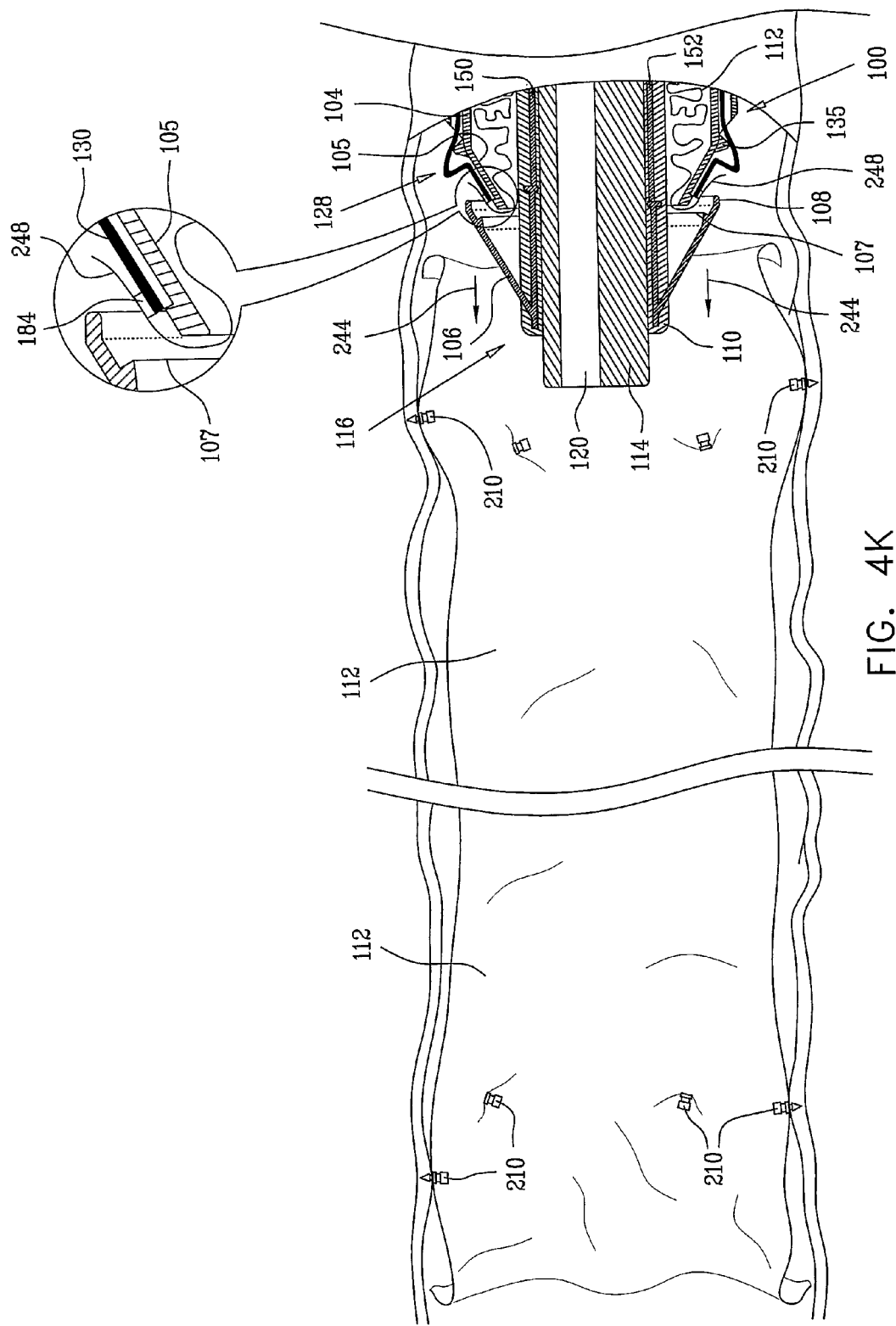

FIG. 4K illustrates cutter cap 106 returning to its original position of FIGS. 1A-2B with respect to the circumferential cutting surface 105, in a direction denoted by arrows 244, by releasing the pulling force on cutter cap tensioning elements 150 and 152. As seen in FIG. 4K, following the cutting of liner 112 (FIG. 4J) and the release of cutter cap 106, a selectable portion of tubular liner 112 is deployed and anchored at both of its end portions within the intestine, and is detached and separated from lining system 116. As further seen in FIG. 4K, a new liner end portion 248 of liner 112 is detachably attached to the positioner leading portions 128 via the leading-end-of-liner engagers 184, and lining system 116 is operative for deployment and anchoring of another portion of liner 112 within the intestine, preferably at another liner deployment location/region as needed.

Figure 4L:
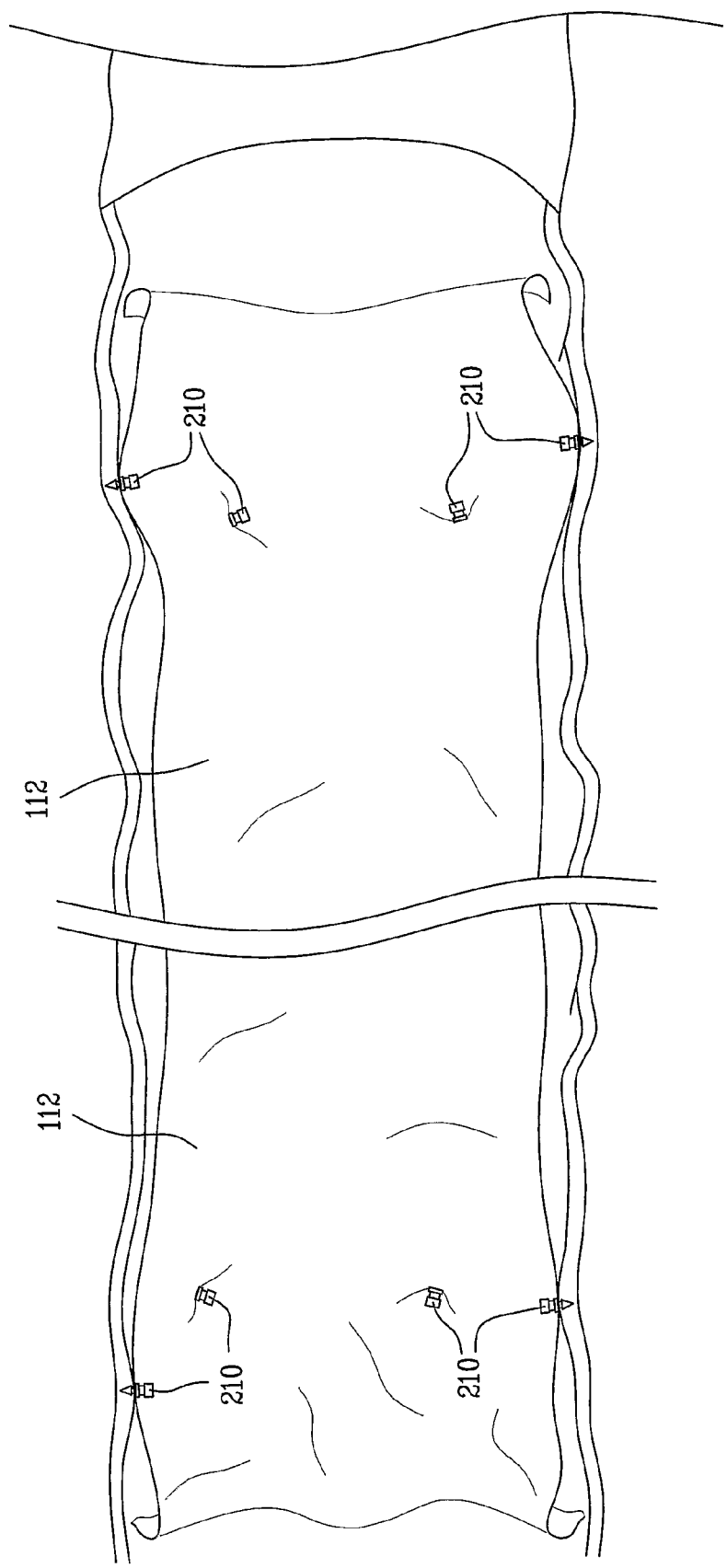
Figure 4M:
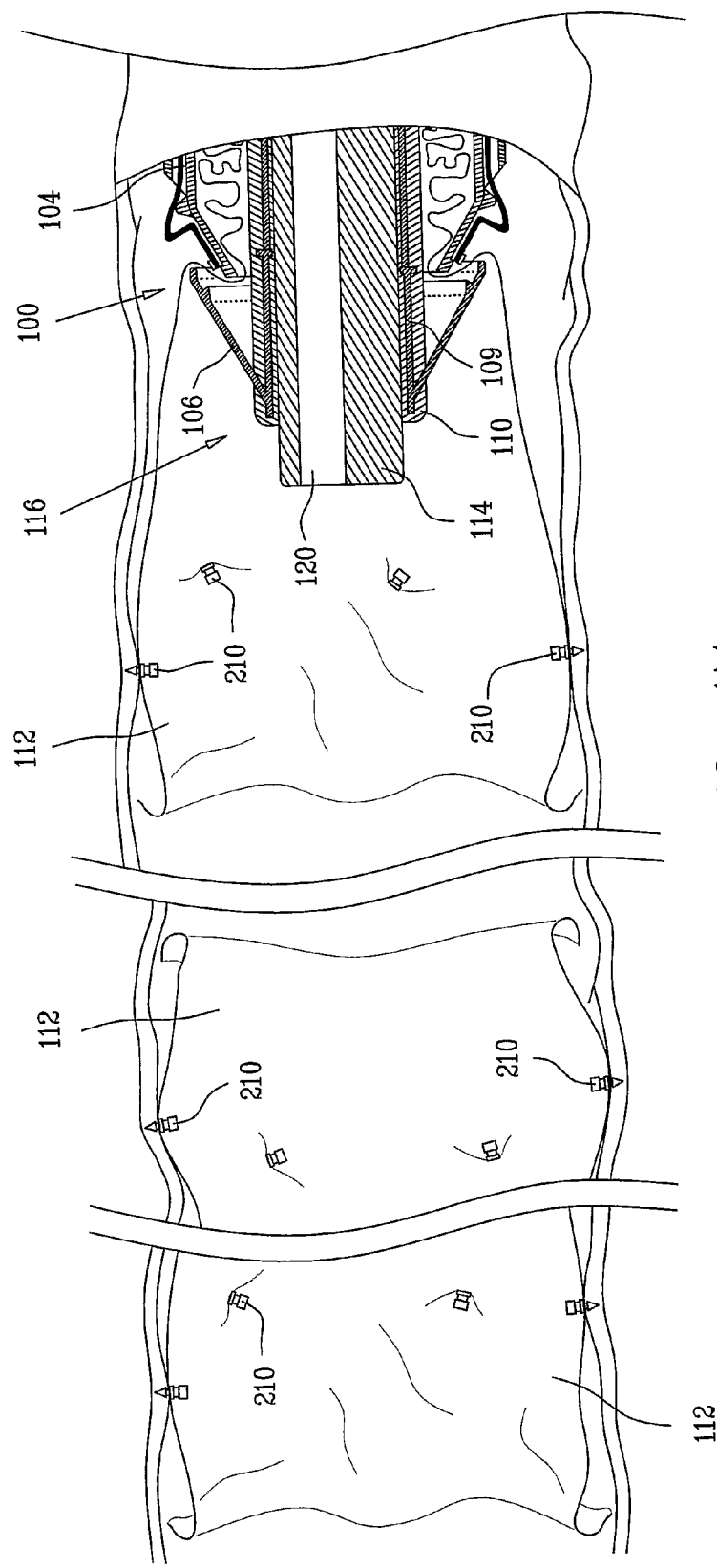

FIG. 4L illustrates the selectable portion of tubular liner 112 deployed and anchored within a portion of the intestine following completion of its deployment and anchoring, and following withdrawal of lining system 116, to a location either partially within the intestine or completely outside the patient's body. Alternatively to withdrawal of lining system 116 following completion of the deployment of the portion of tubular liner 112, lining system 116 may be pushed forward through the deployed portion of liner 112 and advanced further in the intestine (not shown). FIG. 4M illustrates lining system 116 located at a second liner deployment location and repeating the sequence of operation steps described hereinabove with reference to FIGS. 4A-4K for deploying and anchoring a second portion of liner 112 at a second liner deployment location/region, following deployment and anchoring of the first portion of liner 112 at the first deployment location/region as also illustrated in FIG. 4M.

A selectable time period following the placement of tubular liner 112 within the intestine as described hereinabove with reference to FIGS. 4A-4M, one or more of the deployed portions of liner 112 may be removed endoscopically, by approaching the liner placement location with endoscope 114 (or another conventional endoscope), removing each of individual anchors 210 through the instrument channel 120 by an accessory (such as biopsy forceps) which grabs and pulls out the individual anchors 210 through the opposing anchor transversal recesses 222, and thereafter grabbing liner 112 by forceps through instrument channel 120 and pulling it out together with endoscope 114.

It is appreciated that multiple portions of liner 112 may be deployed and anchored along the intestine according to the clinical need. It is appreciated that the length of each liner portion may be selectable, and different liner portions may have different lengths. It is further appreciated that the entire liner 112 may be deployed and anchored within the intestine, either as one continuous liner or as separate liner portions. It is appreciated that different liner portions may be separated along the intestine or alternatively may overlap at least partially with each other.

It is appreciated that the liner deployment length may be a predetermined length and/or be deployed at a predetermined location, such as the duodenum from the pylorus to the ligament of Treitz, the sigmoid colon, or the entire descending colon of a patient. Alternatively, the liner deployment length may be inspected, detected and determined during an endoscopy procedure which can be performed by lining system 116 including endoscope 114, such as the length of an inflamed portion of the intestine, the length of an ulcer detected in the intestine, or the length of a region in the intestine in which obscure gastrointestinal bleeding is detected.

It is appreciated that the properties of tubular liner 112 are suitable for its deployment, anchoring and its clinical function in the intestine or other generally tubular body portion where it is placed. Tubular liner 112 may have a uniform or varying cross sectional diameter. The diameter of tubular liner 112 may be generally smaller than the cross sectional diameter of the intestinal portion where it is placed. This may reduce frictional contact of passing food or stool with the internal walls of the intestinal portion. Alternatively, the diameter of tubular liner 112 may be generally similar to or larger than the cross sectional diameter of the intestinal portion where it is placed. This may provide efficient peristaltic contractions of the intestinal portion, and better contact of the liner 112 with the internal intestinal walls.

In accordance with an embodiment of the present invention useful for liner placement within a small intestine of a patient, the cross sectional diameter of tubular liner 112 is in the range of 20-25 millimeters. According to another embodiment useful for liner placement within a small intestine of a patient, the cross sectional diameter of tubular liner 112 is smaller than 20 millimeters. In accordance with an embodiment of the present invention useful for liner placement within a colon of a patient, the cross sectional diameter of tubular liner 112 is in the range of 25-30 millimeters. According to another embodiment useful for liner placement within a colon of a patient, the cross sectional diameter of tubular liner 112 is larger than 30 millimeters. According to yet another embodiment useful for liner placement within a colon of a patient, the cross sectional diameter of tubular liner 112 is larger than 50 millimeters.

The length of tubular liner 112 is preferably sufficient for placement of the liner 112 or portions thereof along one or more portions of the tubular body as required by the clinical application, while allowing compact packing of the bunched liner 112 within housing portion 104. In accordance with an embodiment of the present invention, the length of liner 112 is longer than 50 centimeters. In accordance with another embodiment of the present invention, the length of liner 112 is longer than 100 centimeters.

It is appreciated that the thickness of liner 112 is suitable for the clinical application and for compact and efficient packing within housing portion 104. Liner 112 may be relatively flexible and\or thin, such as in the range of 20-70 micrometers, thereby providing conformance of liner 112 with the internal surface of the intestine and increased contact therewith. Alternatively, liner 112 may be relatively non-flexible and\or thick, such as in the range of 70-200 micrometers, thereby providing mechanical isolation between the internal surface of the intestinal walls and the food or stool passing through liner 112. Liner 112 may be reinforced with a thin and highly flexible metallic mesh or wires to increase rigidity and provide better mechanical isolation of the intestine from the food or stool passing through liner 112. It is further appreciated that liner 112 may be radio-opaque to allow its x-ray visualization during or after the placement procedure, as provided by the abovementioned reinforcement or in another suitable manner as well known in the art.

It is appreciated that liner 112 may be transparent, thereby allowing visualization of the internal walls of the intestine or other generally tubular body portion by endoscope 114 through liner 112.

Tubular liner 112 may be formed of a thin and flexible bio-compatible material. For example, tubular liner 112 may be formed of a thin and flexible, medical grade polymeric material, such as polyurethane, PEBAX®, PVC, or ePTFE.

In accordance with a preferred embodiment of the present invention, liner 112 and/or individual anchors 210 are made of bio-degradable or bioabsorbable materials as well known in the art, and are dissolved and naturally disposed of or are absorbed and fully excreted from the body, following a generally predetermined time period following placement and anchoring of liner 112 in a tubular body portion of a patient.

An example of bio-degradable material suitable for construction of liner 112 is polyethylene glycol (PEG) having lactic acid incorporated into its base chain, as well known in the art, which dissolves in an aqueous environment. PEG-based bio-degradable materials and products are available commercially from Genzyme Biosurgery Inc. of 55 Cambridge Parkway, Cambridge, Mass. 02142, USA. Bio-degradable or absorbable individual anchors 210 may be formed of Polyglycolic Acid (PGA) material, as available from Kensey Nash Corporation of 735 Pennsylvania Drive, Exton, Pa. 19341, USA. Bioabsorbable individual anchors 210 may be produced similarly to the bioabsorbable ACL Screws for surgical purposes, available from Stryker Inc. of 2825 Airview Boulevard, Kalamazoo, Mich. 49002, USA.

In accordance with an embodiment of the present invention, dissolving or absorbance time of liner 112 is less than 2 weeks. In accordance with a preferred embodiment of the present invention, dissolving time of liner 112 is less than 2 weeks. In accordance with another embodiment of the present invention, dissolving or absorbance time of liner 112 is in the range of 1-6 months. In accordance with yet another embodiment of the present invention, dissolving or absorbance time of liner 112 is in the range of 6-12 months.

In accordance with a preferred embodiment of the present invention, both liner 112 and individual anchors 210 are bio-degradable/bioabsorbable, and the dissolving/absorbance time of individual anchors 210 is longer than the dissolving/absorbance time of liner 112, thereby preventing the release of liner 112 from its anchoring to the intestinal walls following dissolving/absorbance of individual anchors 210 and potential obstruction of the intestine by liner 112. In accordance with a specific embodiment of the present invention, the dissolving/absorbance time of liner 112 is in the range of 1-6 months, and the dissolving/absorbance time of individual anchors 210 is longer than 9 months. In accordance with another specific embodiment of the present invention, the dissolving/absorbance time of liner 112 is less than 30 days, and the dissolving/absorbance time of individual anchors 210 is longer than 60 days.

Alternatively to forming liner 112 and/or individual anchors 210 from a bio-degradable or bioabsorbable material, liner 112 and/or individual anchors 210 may be formed of materials which dissolve when coming into contact with specific swallowable liquids or solutions. The specific liquid or solution is swallowed by the patient a selectable time following the placement of liner 112 in the intestine and induces its dissolving. For example, the liner may be formed of very thin polyurethane, which is sensitive to alcohol and dissolves in its presence. When the liner 112 is needed to be disposed of, the patient drinks alcohol, and the liner dissolves and is disposed of naturally through the digestive tract of the patient.

It is appreciated that swallowing a dissolving solution may be more effective in the upper portion of the digestive tract, before the solution is absorbed by the intestine or diluted by mixing with the content of the intestine. It is appreciated that the dissolving solution or agent may be encapsulated in a cellulose capsule or the like, as well known in the art, which is swallowed by the patient and dissolves within a generally predetermined region in the digestive tract which is upstream and relatively close to the liner placement location and thereby releasing the solution or agent prior to or when reaching the liner placement region.

Alternatively to swallowing of the dissolving substance by the patient, the dissolving substance may be applied directly to the liner 112 endoscopically, by approaching the liner placement location with endoscope 114 (or another conventional endoscope) and spreading the dissolving substance on the inner surface of the liner 112 by an injector or another suitable endoscopy accessory which is inserted through the instrument channel 120 of endoscope 114.

In accordance with another preferred embodiment of the present invention, tubular liner 112 is placed partially within a tubular body portion of a patient and partially outside of the patient's body. For example, liner 112 may be placed and anchored at one end-portion within the rectum or sigmoid colon of a patient, be spread and pass through the anus of the patient, and continue further outside of the patient's body. This may be useful for protecting the anus of the patient from stool contact and mechanical friction in case of severe hemorrhoids or following a hemorrhoidectomy surgery. Similarly, it may also be useful following total colectomy or proctocolectomy surgery, in which the colon of a patient is removed and the terminal small bowel is sutured to the rectum or anus of the patient (anastomosis), for protecting the sutured region. Similar deployment of liner 112 may be useful to protect a stoma of a patient. Preferably, in this embodiment the individual anchors 210 are bio-degradable whereas liner 112 is not bio-degradable. Following a healing time of the patient, for example 2-4 weeks, the individual anchors 210 dissolve and the liner 112 is released and can be pulled out completely from the patient's body.

Figure 5A:
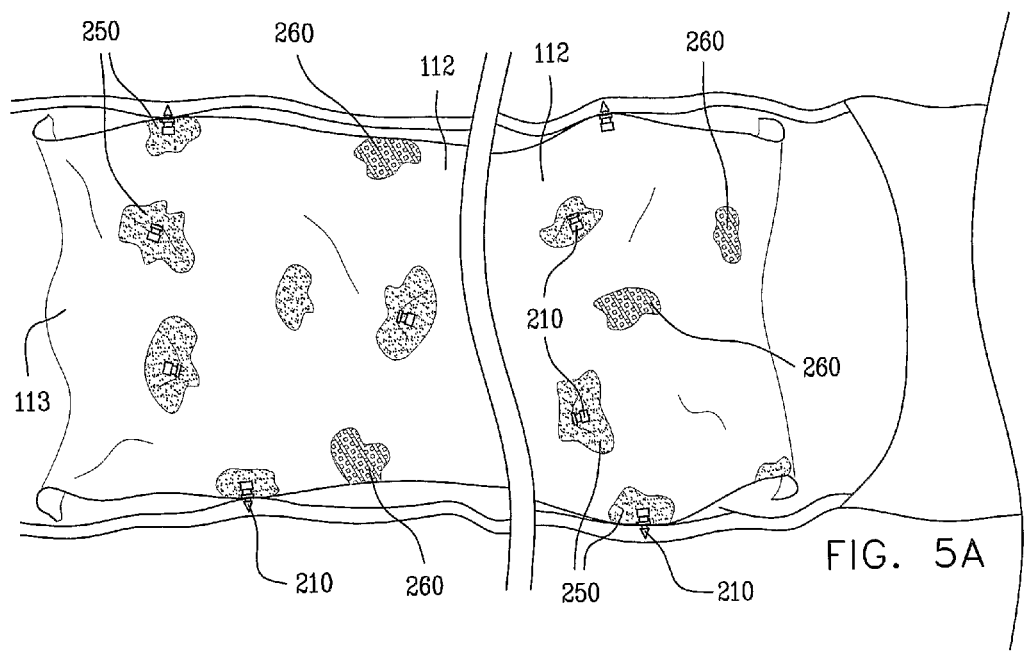
FIGS. 5A and 5B are simplified, partially sectional illustrations of alternative configurations of a tubular liner forming part of the lining system of FIGS. 1A-2B, located within an intestine of a patient.
Figure 5B:
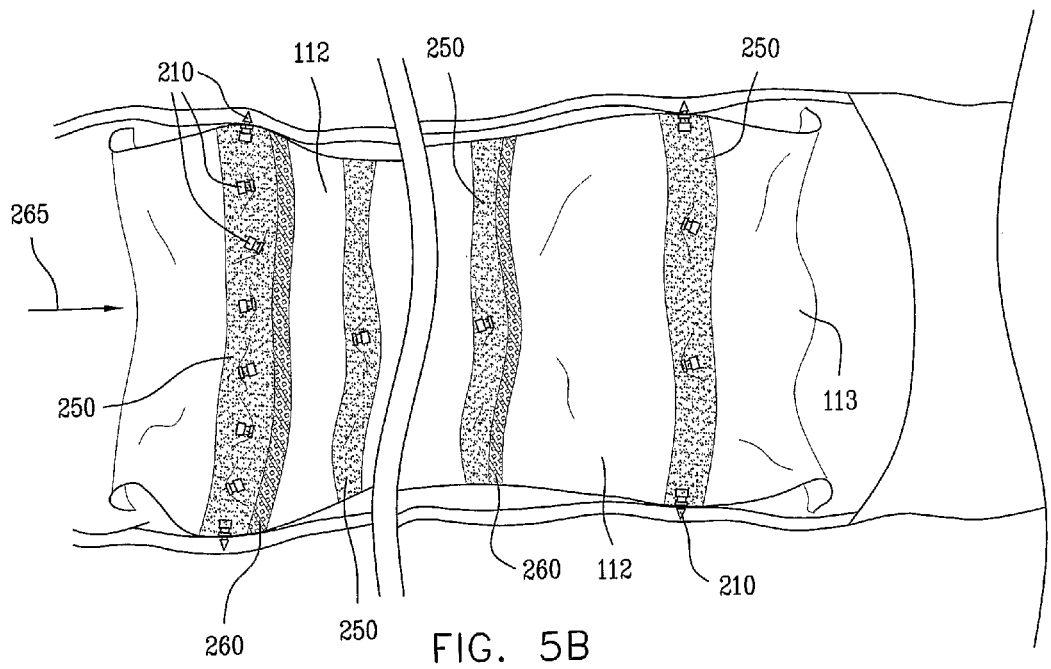

Reference is now made to FIGS. 5A and 5B which are simplified, partially sectional illustrations of alternative configurations of the tubular liner 112, located and anchored within an intestine of a patient, as described hereinabove with reference to FIGS. 4A-4M. As seen in FIGS. 5A and 5B, the individual anchors 210 are positioned within reinforced portions 250 of liner 112, disposed along the area of liner 112. The reinforced portions 250 of liner 112 may be thicker than the rest of the liner area, or be made of a different material which is preferably more rigid than the material of liner 112, or may include a metallic wire mesh embedded in or adhered to liner 112. It is appreciated that other suitable reinforcement mechanisms may be utilized. It is appreciated that anchoring of individual anchors 210 within reinforced regions of liner 112 provide higher mechanical resistance of liner 112 to detachment of liner 112 from individual anchors 210 due to local failure and undesired stretching of liner 112 at the anchoring locations, for example due to peristaltic constructions of the intestine or frictional forces applied on liner 112 by food or stool passing therethrough.

The reinforced portions 250 may assume any appropriate shape, such as isolated regions having rounded, elliptic or other shape (FIG. 5A), reinforcement strips having an appropriate slope, or circumferential rings (FIG. 5B). Preferably, a plurality of reinforced portions 250 is generally circumferentially disposed along liner 112. In accordance with an embodiment of the present invention, the tubular liner 112 is generally stretchable intermediate the plurality of generally circumferentially disposed reinforced portions.

As further illustrated in FIGS. 5A and 5B liner 112 may include, alternatively or additionally, attachment portions 260 on its outer surface, facing the internal walls of the intestine and attaching liner 112 thereto. Attachment portions 260 of liner 112 may comprise a layer of sticky material such as a layer including sodium alginate that is capable of attaching well to the internal intestinal walls, and preferably can be separated from the intestine under application of moderate pulling or shear forces, when removing liner 112 from the intestine. It is appreciated that attachment portions 260 increase the contact and aerial engagement between liner 112 and the intestine, and prevent or reduce collapsing of tubular liner 112 in the absence of food or stool. It is further appreciated that continuous peripheral attachment portions 260 that are located in proximity to an anchoring location of liner 112, such as the left anchoring location illustrated in FIG. 5B, provide circumferential sealing between tubular liner 112 and the intestinal walls at the anchoring location.

In the embodiment illustrated in FIG. 5B, the anchoring of liner 112 to the intestine at the left anchoring location is performed by a relatively large number of individual anchors 210 distributed circumferentially and having narrow spacing therebetween, thereby providing substantially continuous circumferential attachment of liner 112 to the intestine and generally sealing of openings therebetween. It is appreciated that the left attachment portion 260 further increases the circumferential sealing and attachment of liner 112 to the intestine, as described hereinabove. It is further seen in FIG. 5B that the anchoring of liner 112 to the intestine at the right anchoring location is performed by a relatively small number of individual anchors 210 distributed circumferentially and having wide spacing therebetween, thereby allowing circumferential openings between liner 112 and the intestine.

As denoted by arrow 265 in FIG. 5B, the food or stool flow direction in the embodiment of FIG. 5B is from left to right.

It is thus appreciated that the left anchoring location is upstream with respect to food or stool flow direction, and the right anchoring location is downstream with respect to food or stool flow direction. Thus, the tight and continuous circumferential anchoring of liner 112 to the intestine at the left anchoring location prevents or reduces penetration of food or stool into the space between liner 112 and the intestinal walls, while the openings between the liner 112 and the intestinal walls at the right anchoring location support draining and passage of intestinal fluids therethrough.

As further illustrated in FIGS. 5A and 5B, liner 112 is anchored to the intestine by individual anchors 210 in few locations along its length, beyond its anchoring to the intestine at its left and right end portions. Such anchoring may be performed by utilizing one or more appropriate anchoring assemblies as described hereinabove with reference to FIGS. 4C-4G, during the advancement or withdrawal of lining system 116, and following the anchoring of liner 112 at the first anchoring location.

It is appreciated that such anchoring along the length of the deployed liner 112 may assist in fixing liner 112 within the intestine, reduce the forces applied on the liner 112 at its anchored end portions, and prevent or reduce collapsing of liner 112 when no food or stool passes through it. It is further appreciated that such anchoring along the length of the deployed liner 112 is particularly beneficial in case that a long portion of liner 112 is deployed, for example a liner portion in the range of 50-120 centimeters.

Figure 6:
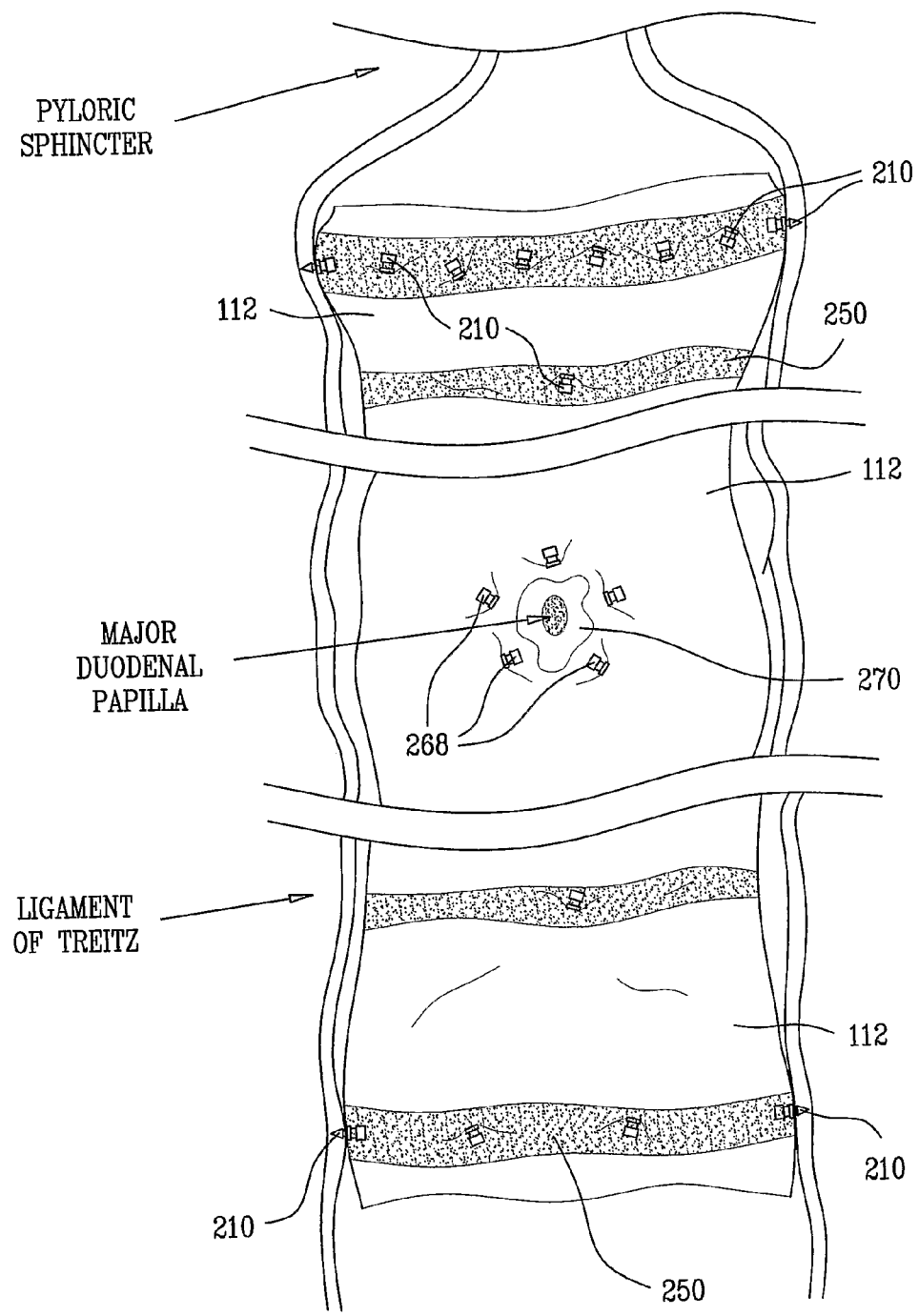
FIG. 6 is a simplified, partially sectional illustration of an alternative configuration of a tubular liner forming part of the lining system of FIGS. 1A-2B, located within a duodenum of a patient.

Reference is now made to FIG. 6, which is a simplified, partially sectional schematic illustration of another alternative configuration of a tubular liner forming part of the lining system 116 of FIGS. 1A-2B, located within a duodenum of a patient as described hereinabove with reference to FIGS. 4A-4M. As illustrated in FIG. 6, an upper end portion of tubular liner 112 is located adjacent the pylorus of the patient and anchored thereat. It is appreciated that the upper end portion of tubular liner 112 can be anchored to the rearward end of the duodenum adjacent the pylorus (FIG. 6), to the pyloric sphincter itself, or to the stomach of the patient adjacent to the pyloric sphincter (not shown). Preferably, the upper end portion of liner 112 is anchored thereat by a large number of individual anchors 210 disposed circumferentially at the upper anchoring location and having narrow spacing therebetween, thereby providing circumferential contact between the tubular liner 112 and the tissue at the anchoring location and preventing penetration of food into the space between liner 112 and the duodenum.

As further illustrated in FIG. 6, a lower end portion of tubular liner 112 is located downstream the Ligament of Treitz of the patient and is anchored to the intestine thereat, preferably by a small number of individual anchors 210 disposed circumferentially at the lower anchoring location and having wide spacing therebetween, thereby allowing openings between liner 112 and the intestine at the lower anchoring location and draining of pancreatic and bile fluids therethrough.

In accordance with an embodiment of the present invention, following the anchoring of liner 112 at its upper and lower end portions (FIG. 6), additional anchors, denoted in FIG. 6 by reference numeral 268, are deployed circularly around the papilla to anchor the liner 112 around it and provide circumferential contact between liner 112 and the duodenum around the papilla. Thereafter, a circular opening 270 is cut in liner 112 radially inwardly to the perimeter of the circularly deployed anchors 268, thereby allowing pancreatic and bile fluids to mix with food passing through the duodenum. It is appreciated that the circularly deployed anchors 268 prevent or reduce the penetration of food or liquids through the circular opening 270 into the space between liner 112 and the duodenum.

Cutting of the circular opening 270 in liner 112 can be performed by first detecting the papilla by endoscope 114 (or another conventional endoscope), and thereafter forming the circular opening in liner 112 by utilizing a suitable conventional endoscopy accessory capable of burning lines through and/or cutting liner 112, through the instrument channel 120 of endoscope 114. Examples of conventional endoscopy accessories capable of burning lines through liner 112 are argon plasma coagulation (APC) probes such as APC 300 probe, commercially available from ERBE USA Inc. of 2225 Northwest Parkway, Marietta, Georgia 30067, USA, and laser probes such as Medilas D FlexiPulse probe, commercially available from Dornier MedTech Europe GmbH of Argelsrieder Feld 7 D-82234, Wessling, Germany.

It is appreciated that the APC and laser probes described hereinabove may be utilized also for burning holes in liner 112 around individual anchors 210 and 268, thereby separating liner 112 from the anchors and the intestine for removal thereof, instead of removing the individual anchors 210 and 268.

It is appreciated that the apparatus described hereinabove with reference to FIG. 6 (either with or without the liner opening 270) is operative for preventing or substantially reducing contact between the duodenum and food, liquids and nutrients passing therethrough, which may assist in the treatment of obesity and/or Type 2 Diabetes, as well known in the art. Accordingly, tubular liner 112 illustrated in FIG. 6 is preferably impermeable to food, liquids and nutrients. Additionally, liner 112 is preferably transparent to allow detection of the biliary duct through liner 112. Optionally liner 112 and/or individual anchors 210 and 268 may be bio-degradable, as described hereinabove.

It is appreciated that encircling a localized region within the deployed and anchored tubular liner 112 by anchors 265 and/or burning of hole 270 as described hereinabove with reference to FIG. 6 may be performed in any other location within the digestive tract of the patient where liner 112 is placed.

Figure 7A:
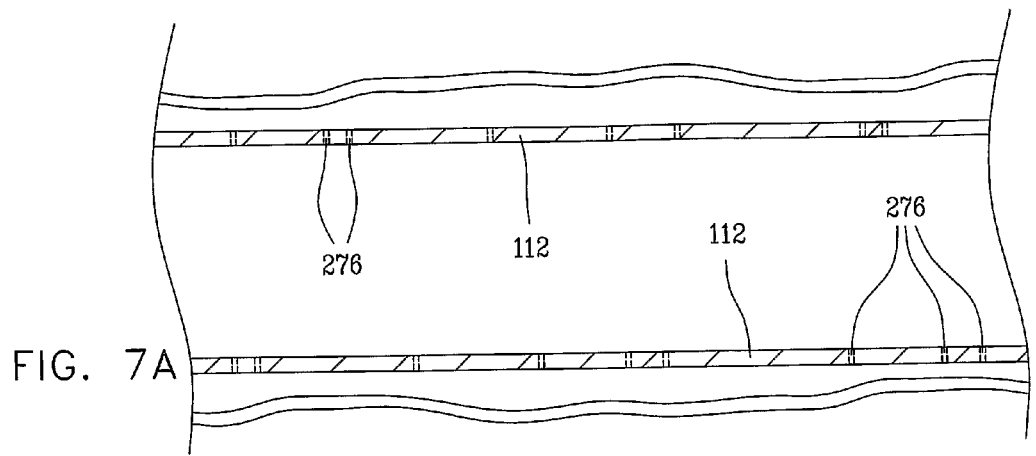
FIGS. 7A, 7B and 7C are simplified sectional illustrations of alternative constructions of a tubular liner forming part of the lining system of FIGS. 1A-2B having different layer structures, located within an intestine of a patient.
Figure 7B:
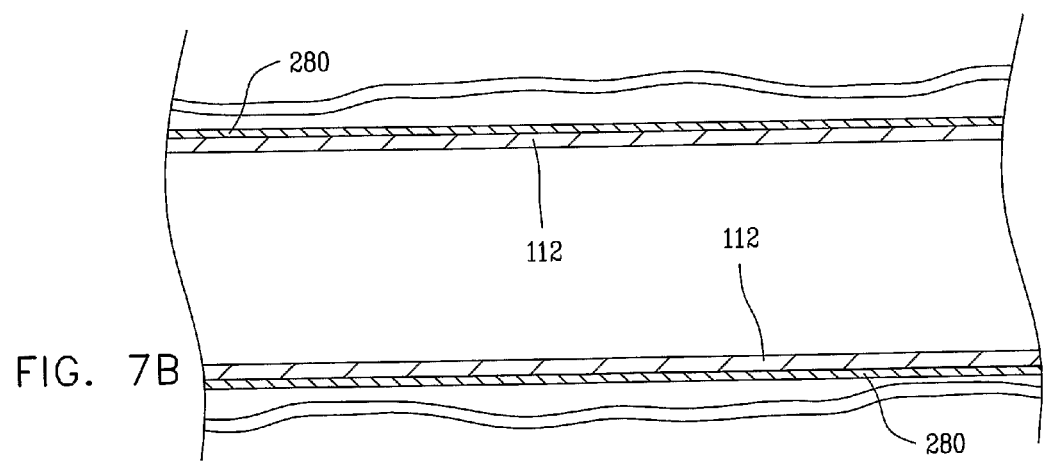
Figure 7C:
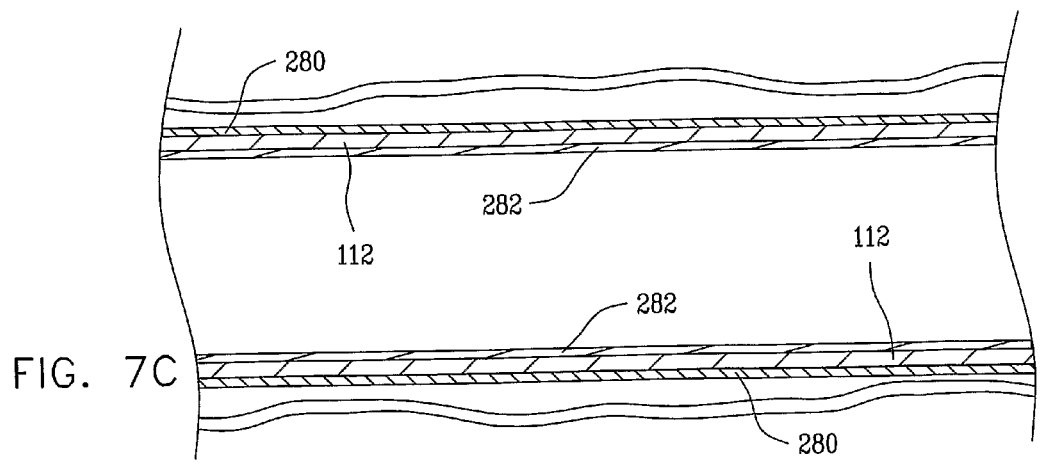

Reference is now made to FIGS. 7A, 7B and 7C, which are simplified sectional illustrations of alternative constructions of tubular liner 112 forming part of the lining system 116 of FIGS. 1A-2B and having different layer structures, located within an intestine of a patient.

FIG. 7A illustrates a semi-permeable liner 112. In the apparatus of FIG. 7A the tubular liner 112 includes transversal micro-pores 276 traversing through its width, which permit passage therethrough of certain substances while prohibiting the passage of other substances. For example, micropores 276 may permit passage therethrough of molecules or particles of up to a predetermined size, and prohibit transfer of larger molecules or particles. Alternatively or additionally, micro-pores 276 may allow transfer of gas and prohibit passage of liquids and solid substances therethrough. This may be utilized, for example, for applying partial vacuum on the intestine through the liner 112, which can be useful for providing tight engagement between liner 112 and the intestine, or for any other suitable application. Yet alternatively, micropores 276 may allow transfer of gas and liquids and prohibit passage of solid substances therethrough. Specifically, liner 112 may permit passage therethrough of medications to the space between the semi-permeable liner 112 and the intestine, while preventing contact of the intestine with solid and/or liquid content passing through the digestive tract, such as food or stool.

The semi-permeable liner 112 of FIG. 7A may be electrostatically charged, thereby allowing passage therethrough of charged ions and/or particles while blocking other materials, or alternatively permit the transfer of ions/particles of either positive or negative electric charge. It is appreciated that semi-permeable liner 112 may employ other mechanisms to provide selective transfer of substances therethrough, as well known in the art of semi-permeable layers and membranes.

It is appreciated that semi-permeable liner 112 may be operative to permit unidirectional flow through it of the permitted substance, as well known in the art. For example, liner 112 may allow liquid or medication to pass through it from its inner volume to the space between its outer surface and the intestinal walls, but prohibit counter-flow of the liquid or medication from the space between the liner 112 and the intestinal walls into the inner volume of the liner. This may increase the effectiveness of a medication for treating the intestine, due to higher exposure of the intestinal walls to the medication and increased absorbance of the medication by the intestine.

FIG. 7B illustrates a tubular liner 112 having a liner outer layer 280 disposed on its outer surface and being in partial contact with the internal intestinal walls. Liner outer layer 280 may comprise a layer of impregnated medication or treating solution. Alternatively or additionally, liner outer layer 280 may comprise a low-friction layer which minimizes the frictional forces applied on the intestinal walls by liner 112, in particular when intestinal content passes therethrough and during peristaltic contractions of the intestine. An example of a liner 112 having a low-friction outer layer 280 is a liner made of thin PVC and covered with SLIPSKIN™ coating, available from MCTec of 9 Edisonstraat, Venlo, Netherlands. Alternatively or additionally, outer layer 280 may include attachment portions as described hereinabove with reference to FIGS. 5A and 5B.

FIG. 7C illustrates a tubular liner 112 having the liner outer layer 280 as described hereinabove with reference to FIG. 7B, and a liner inner layer 282 disposed on its inner surface of liner 112. Liner inner layer 282 may be identical to liner outer layer 280, or different from outer layer 280. For example, both outer layer 280 and inner layer 282 may comprise a low-friction coating such as a hydrophilic coating. As another example, the outer layer 280 may comprise a medication for treating the intestine, while the inner layer 282 comprises a hydrophilic coating for reducing frictional forces between the passing food/stool, the liner 112 and the intestine.

Figure 8A:
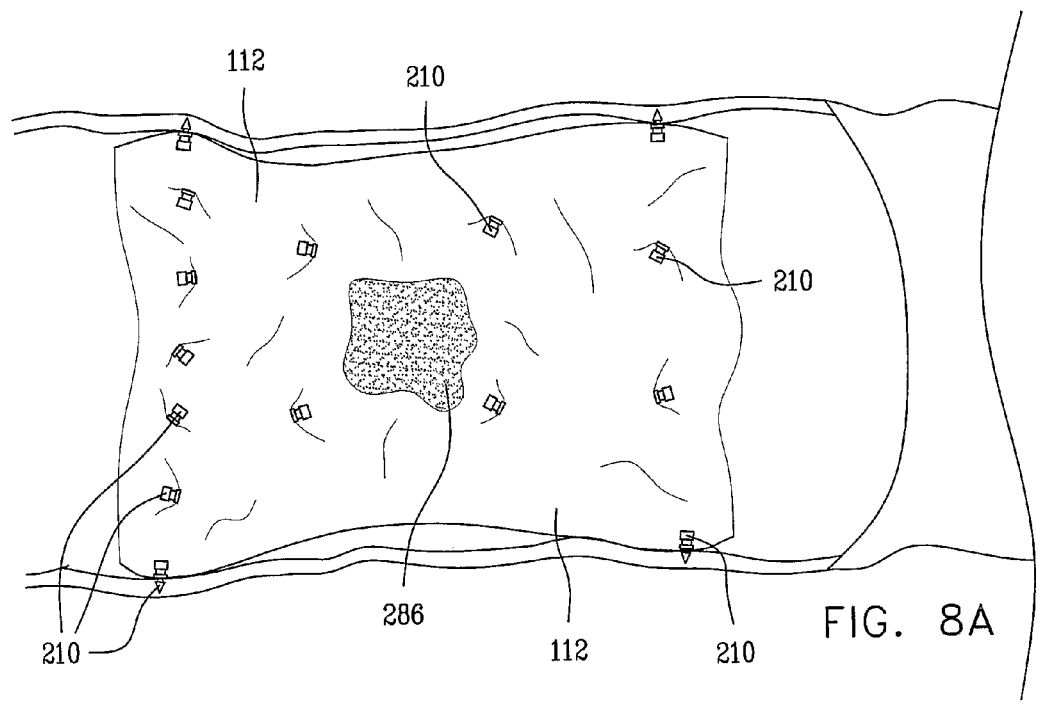
FIGS. 8A and 8B are simplified, partially sectional, illustrations of a tubular liner forming part of the lining system of FIGS. 1A-2B, located within a pathologic, ill or malfunctioning portion of an intestine of a patient.
Figure 8B:
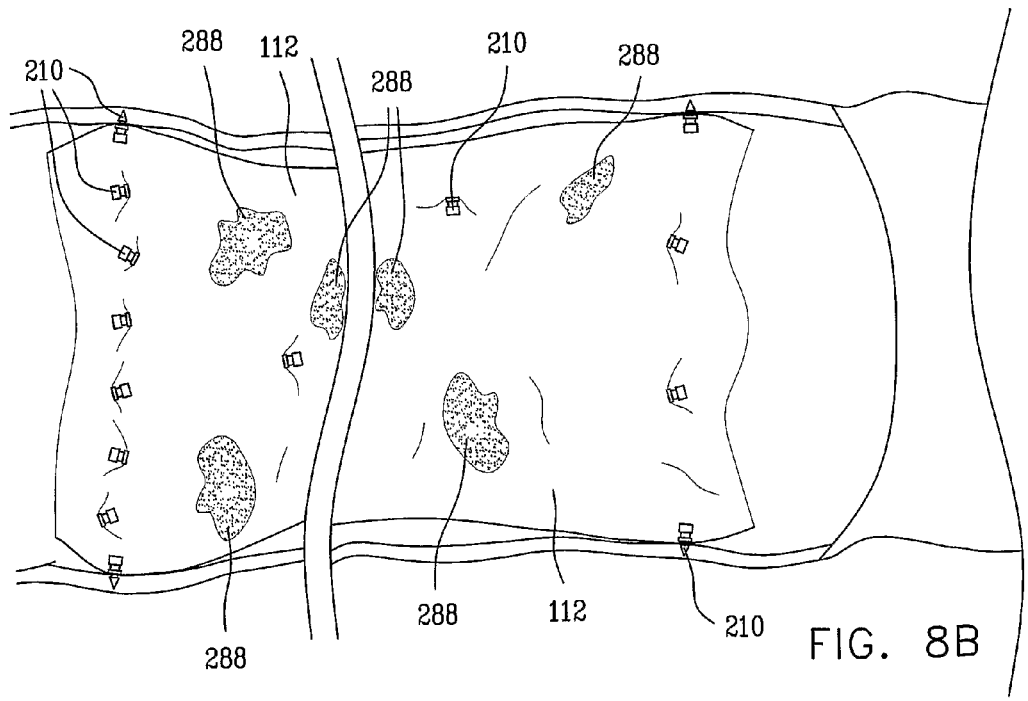

Reference is now made to FIGS. 8A and 8B, which are simplified partially sectional illustrations of a tubular liner forming part of the lining system of FIGS. 1A-2B, located within a pathologic, ill or malfunctioning portion of an intestine of a patient. As illustrated in FIGS. 8A and 8B, in accordance with a preferred embodiment and method of treatment of the present invention, liner 112 is placed within a portion or portions of the intestine of a patient by lining system 116 as described hereinabove with reference to FIGS. 4A-4M for assisting the treatment and/or healing of a pathologic, ill or malfunctioning portion of the intestine, and/or for assisting the treatment or healing of diseases which are related to the gastrointestinal tract. Pathologies and illnesses of the digestive tract in which liner placement in the pathologic or ill portion may assist their healing include, for example, inflammatory diseases such as Crohn's disease, colitis and ulcerative colitis, gastro-intestinal bleeding, ulceration, diverticulosis, diverticulitis or any other diverticular disease, chronic constipation or diarrhea, fistulas, intestinal perforation and anastomosa or another type of surgically treated location in the digestive tract.

Preferably, the pathologic, ill or malfunctioning portion of the intestine is detected by endoscope 114 of lining system 116 and the tubular liner 112 is placed accordingly in the detected location/region. Preferably, detection by endoscope 114 and placement of one or more portions of liner 112 accordingly by lining system 116 is performed in one interventional session, without intermediately removing the endoscope 114 and/or lining system 116 from the intestine.

As illustrated in FIG. 8A, liner 112 is placed by lining system 116 within a portion of the intestine of a patient which exhibits a localized pathology 286. The localized pathology 286 may be one or more of a diverticulum, a fistula, a bleeding point, a hole in the intestinal wall due to endoscopic perforation or another reason, an ulcer, an anastomosis, a local inflammation of the intestine, or any other local pathology or ill segment of the intestine.

Preferably, liner 112 is anchored to the intestine both rearwardly and forwardly of the pathology 286, thereby protecting and separating pathology 286 from food or stool passing through the intestine. Preferably, the anchoring upstream the pathology 286 provides circumferential engagement of liner 112 to the intestine and prevents food/stool penetration between the liner 112 and the intestine, while the anchoring downstream the pathology allows drainage of intestinal fluids, as described hereinabove with reference to FIG. 5B. Preferably, local pathology 286 is shielded and protected by a short segment of liner 112. In accordance with a specific configuration and treatment method of the present invention, the length of the portion of liner 112 deployed over local pathology 286 is in the range of 5 to 15 centimeters. Yet specifically, the length of liner 112 protecting a localized pathology 286 in the colon of a patient is less than 8 centimeters, and the length of liner 112 protecting a localized pathology 286 in the small intestine of a patient is less than 4 centimeters.

As illustrated in FIG. 8B, liner 112 is placed by lining system 116 within a portion of the intestine of a patient which exhibits a generally distributed pathology 288. The generally distributed pathology 288 may be one or more of an inflamed portion of the intestine exhibiting for example Crohn's disease, colitis or ulcerative colitis, an area of the intestine having multiplicity of bleeding locations such as in the case of obscure gastro-intestinal bleeding, a region of the intestine exhibiting diverticular disease such as diverticulosis and/or diverticulitis, or any other generally distributed pathology or ill segment of the intestine. It is appreciated that liner 112 may be placed in accordance with the embodiment and method described herein with reference to FIG. 8B for assisting the treatment of gastrointestinal-related diseases, such as over the duodenum of a patient exhibiting type 2 diabetes and/or obesity, or over a portion of the colon and specifically of the descending colon of a patient suffering from chronic constipation.

Preferably, liner 112 is anchored to the intestine both rearwardly and forwardly of the pathology 288, thereby protecting and separating pathology 288 from food or stool passing through the intestine. Preferably, the anchoring upstream the pathology 288 provides circumferential engagement of liner 112 to the intestine and prevents food/stool penetration between the liner 112 and the intestine, while the anchoring downstream the pathology allows drainage of intestinal fluids, as described hereinabove with reference to FIG. 5B.

It is appreciated that in accordance with the apparatus and treatment method described hereinabove with reference to FIGS. 8A and 8B, multiple portions of liner 112 may be placed over multiple localized and/or distributed pathologies as described hereinabove with reference to FIGS. 4A-4M.

As seen in FIGS. 8A and 8B, liner 112 is preferably transparent, thereby allowing visualization of pathology 286 and pathology 288 through liner 112.

It is appreciated that the properties of liner 112 employed in accordance with the method of treatment described hereinabove with reference to FIGS. 8A and 8B are suitable for the clinical application and functionality, as described hereinabove with reference to FIGS. 4A-4M and 7A-7C. For example, a liner 112 covering an endoscopic perforation, a diverticulum or a fistula, is preferably impermeable to fluids, liquid and solid content of the intestine. An impermeable liner covering a hole in the intestinal wall may assist its natural healing process and prevent contamination of the abdominal cavity by intestinal content.

As another example, a liner 112 covering an inflamed portion of the intestine may be impermeable to food and stool, but permeable to medication. It is appreciated that placing a liner within an inflamed portion of the intestine, which separates nutrients, liquids, food or stool from the inflamed mucosa of the intestine, may reduce inflammation of the isolated mucosa and initiate, facilitate, or accelerate healing of the inflamed portion of the intestine or reduce or prevent further deterioration. Alternatively or additionally, the liner 112 may be impregnated with medication on its outer surface as described hereinabove with reference to FIGS. 7B and 7C.

As a further example, a liner covering a localized or distributed pathology may be covered on its outer surface with a hydrophilic coating to minimize friction of liner 112 and intestinal content with the pathology. Additionally or alternatively, the liner 112 may be covered with a hydrophilic coating on its inner surface, thereby providing faster and easier passage of intestinal content therethrough and lowering frictional forces applied on the pathology.

Yet as another example, a liner placed within a portion of the colon of a patient suffering from chronic constipation is impermeable to liquids, thereby limiting liquid absorption by the liner-placed portion of the colon. Such a liner is preferably also highly thin and flexible to transfer fully the peristaltic contractions of the intestine, and may be covered with a hydrophilic layer on its inner surface to allow faster passage of stool therethrough. It is appreciated that placing such a tubular generally liquid impermeable liner at a desired location in a colon of a patient may assist in treating constipation of a patient, and in particular chronic constipation.

It is appreciated that liner 112 may be employed in accordance with the method of treatment described hereinabove with reference to FIGS. 8A and 8B in a portion of the digestive tract which is not the intestine, such as the stomach or the esophagus, or in an organ which is not part of the digestive tract.

Figure 9:
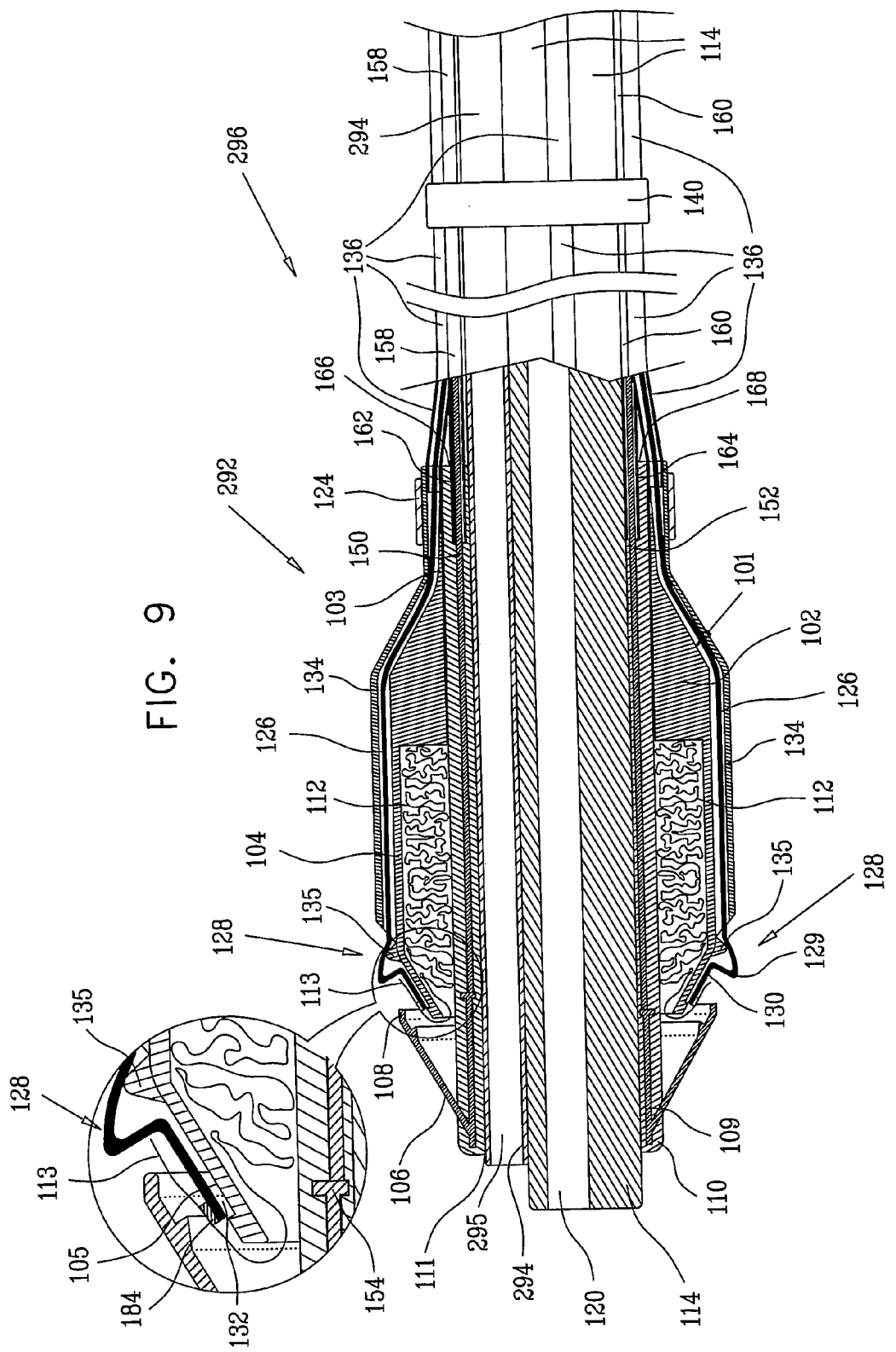
FIG. 9 is a simplified, partially sectional, illustration of an apparatus similar to the apparatus of FIGS. 1A-2B and further including an external tube.

Reference is now made to FIG. 9, which is a simplified, partially sectional, illustration of an apparatus similar to the apparatus of FIGS. 1A-2B and further including an external tube. As illustrated in FIG. 9, a lining assembly 292 is constructed and operative similarly to the lining assembly 100 described with reference to FIGS. 1A-2B, and includes all of the elements and sub-assemblies as the lining assembly 100, which are denoted in FIG. 9 by the same reference numerals as in FIGS. 1A-2B. Lining assembly 292 further includes an external tube 294 having at least one lumen 295, which is traversing lining assembly 292 rearwardly with its forward portion traversing tubular sleeve 110, preferably inwardly within lumen 111 of tubular sleeve 110.

The forward portion of external tube 294 may be attached inwardly to tubular sleeve 110 in any conventional manner, such as by adhesive or by providing within tubular sleeve 110 a tubular passageway through which the external tube 294 is inserted (not shown), similarly to the external tube of the flexible endoscope assembly apparatus described in inventor's co-pending applications PCT/IL2005/000849 and PCT/IL2007/000600 which are incorporated herein by reference in their entirety.

Lining assembly 292 is preferably mounted on the forward portion of endoscope 114 as illustrated in FIG. 9 to form a lining system 296, which is similar to lining system 116 described hereinabove with reference to FIGS. 1A-2B, and further includes the external tube 294. Preferably, the forward portion of external tube 294 is located outwardly of endoscope 114 and inwardly of or within tubular sleeve 110, similarly to the external tube of the flexible endoscope assembly apparatus described in inventor's co-pending applications PCT/IL2005/000849 and PCT/IL2007/000600 which are incorporated herein by reference in their entirety.

Preferably, external tube 294 is positioned along the endoscope 114, and may be attached to the endoscope 114 at multiple locations along its length in any suitable manner such as medical adhesive tape, and preferably by the flexible bands 140. A rearward end of external tube 294 is typically open outside of a patient's body to enable insertion therethrough of a variety of endoscopic tools and accessories by an operator (not shown), as will be described hereinbelow, to a utilization location forward of lining system 296.

It is appreciated that the construction of lining assembly 292 and lining system 294 are well explanatory by the description hereinabove with reference to FIGS. 1A-2B. It is further appreciated that an operation mode of lining system 296 is well explanatory by the description hereinabove with reference to FIGS. 4A-4M.

Preferably, external tube 294 is utilized for passing any suitable endoscopic tool or accessory through lumen 295 to a utilization location forward of the forward end of endoscope 114 and of lining system 296, additionally or alternatively to the utilization of the instrument channel 120 of endoscope 114, as described hereinabove. For example, external tube 294 can be utilized for passage therethrough of the anchoring assembly 200 or another anchoring tool, a polyp cauterizer, biopsy forceps, an argon probe coagulator, a laser probe, or any other suitable accessory.

Particularly, external tube 294 may be utilized for passage therethrough of the anchoring assembly 200 or another anchoring tool to the anchoring location forward of lining system 296, in case that the endoscope 114 or other inserter does not comprise an instrument channel, or in case that the instrument channel 120 of endoscope 114 is not wide enough for passage therethrough of the anchoring assembly 200 or other anchoring tool. It is thus appreciated that the diameter of lumen 295 of external tube 294 is sufficiently wide to allow insertion therethrough of the anchoring assembly 200 or other anchoring tool. In accordance with an embodiment of the present invention, lumen 295 has a diameter in the range of 2-4 millimeters. According to another embodiment of the present invention, lumen 295 has a diameter in the range of 4-6 millimeters. In accordance with yet another embodiment of the present invention, lumen 295 has a diameter larger than 6 millimeters.

Figure 10:
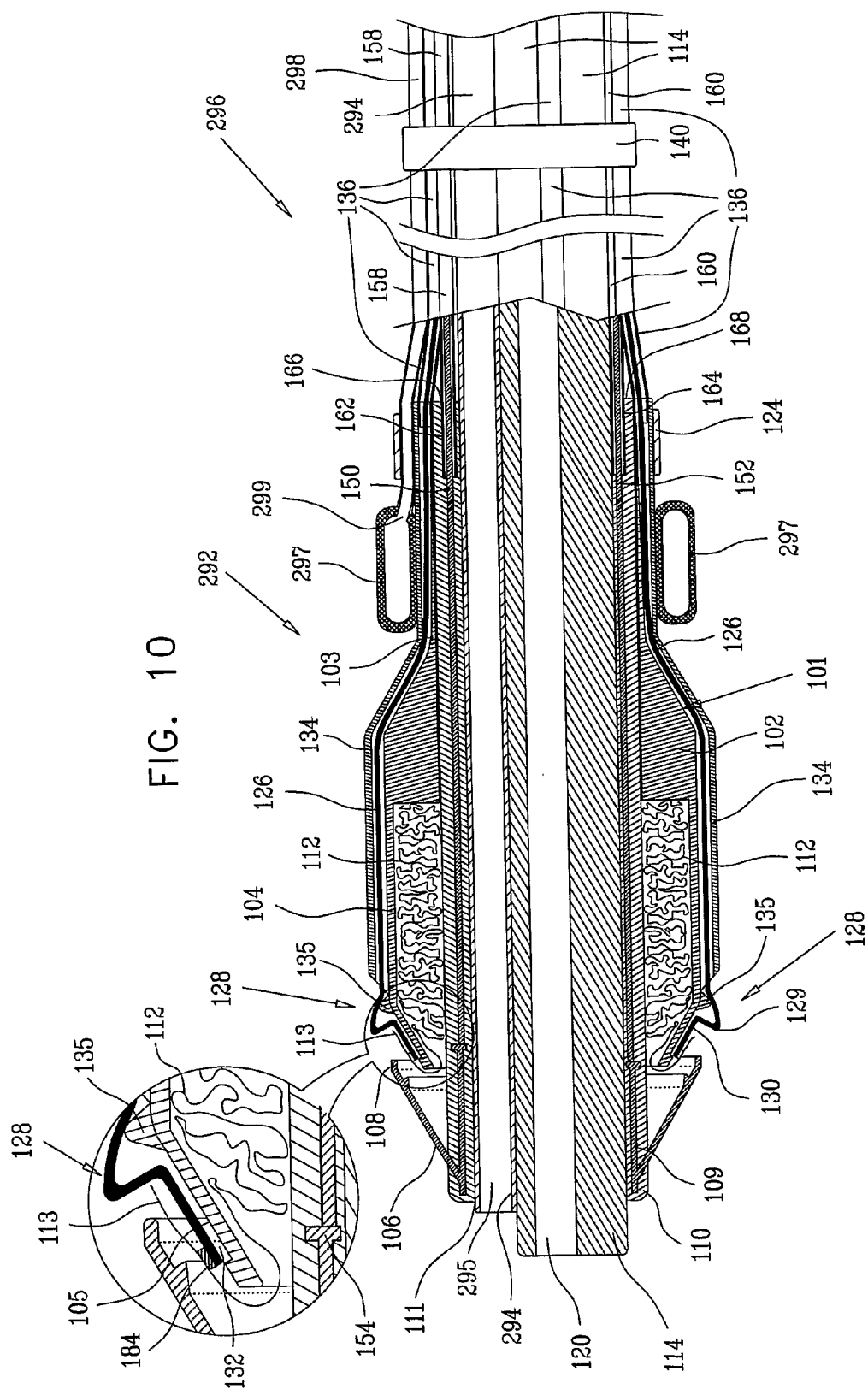
FIG. 10 is a simplified, partially sectional, illustration of an apparatus similar to the apparatus of FIG. 9 and further including an inflatable balloon.

Reference is now made to FIG. 10, which is a simplified, partially sectional, illustration of an apparatus similar to the apparatus of FIG. 9 and further including an inflatable balloon. As illustrated in FIG. 10, lining assembly 292 further includes an inflatable peripheral balloon 297, which is fixedly attached to mounting portion 103 of bunched liner container 101 intermediate bunched liner container body 102 and band 124. Peripheral balloon 297 communicates with an inflation tube 298 via an aperture 299. Inflation tube 298 is positioned along the endoscope 114, and may be attached to the endoscope 114 at multiple locations along its length in any suitable manner such as medical adhesive tape, and preferably by the flexible bands 140. A rearward end of inflation tube 298 typically communicates with an appropriate inflator operative for selectable inflation or deflation of balloon 297 (not shown).

Preferably, peripheral balloon 297 is an anchoring balloon, operative when inflated within a tubular body portion of a patient such as an intestine to anchor lining assembly 292 and lining system 296 to the internal walls of the tubular body portion.

Peripheral balloon 297 may be utilized for anchoring and/or stabilizing the lining system 296 relative to the intestine during an endoscopy procedure as needed, and specifically during anchoring of liner 112 to the intestine.

Reference is now made to FIGS. 11A-11D, which are respective pictorial and sectional illustrations of an anchors applicator 300, for use with the lining system 116 of FIGS. 1A-2B or with the lining system 296 of FIG. 9 and FIG. 10. Anchors applicator 300 may be utilized in conjugation with lining systems 116 and 296 in accordance with the mode of operation described hereinabove with reference to FIGS. 4A-4M, either alternatively or additionally to the usage of anchoring assembly 200 of FIGS. 3A and 3B.

As illustrated in FIGS. 11A and 11B, anchors applicator 300 includes a multi-lumen tube 302 which includes at least a first lumen 304 and a second lumen 306. First lumen 304 further extends at its forward portion through an applicator forward tube 308, which is firmly attached to the multi-lumen forward end 309 of multi-lumen tube 302 or is formed integrally with multi-lumen tube 302. The length of the applicator forward tube 308 may typically be in the range of 20-100 millimeters, though shorter or longer applicator forward tube 308 may be employed. It is appreciated that both multi-lumen 302 and applicator forward tube 308 are generally flexible, and are bendable under application of moderate bending forces.

The first lumen 304 contains therewithin a multiplicity of successively deployed anchors 310, arranged successively within its forward portion. Typically, first lumen 304 contains a number of between four and forty anchors 310, though the number of anchors 310 preloaded within lumen 304 may alternatively be smaller than four or larger than forty. A circumferential forward stopper 314 is fixedly located within lumen 304 at its forward end, for preventing undesired extraction of successively deployed anchors 310 out of lumen 304. It is appreciated that both the circumferential forward stopper 314 and the forward end of applicator forward tube 308 are stretchable in a radial direction to an extent which allows extraction of individual anchors 310 throughout the forward end of applicator forward tube 308 under application of moderate axial force on the anchors 310.

First lumen 304 further includes therewithin a long flexible piston 320, which engages the last, most rearward anchor 310, which is denoted by reference numeral 322 in FIG. 11B, through a flexible piston forward end 324. Rearward end of first lumen 304 is typically open to enable rearward end of flexible piston 320 to extend therefrom outside of a patient's body, thereby enabling pushing of flexible piston 320 along and relative to multi-lumen tube 302 by an operator (not shown) for pressing against the successively deployed anchors 310 and application of axial forces thereon.

Preferably the second lumen 306 may accommodate a tensioning or compression wire 326, which is firmly attached to the applicator forward tube 308 at a wire attachment location 328, forwardly of the multi-lumen forward end 309, and typically 4-25 millimeters from the forward edge of applicator forward tube 308. Rearward end of second lumen 306 is typically open to enable rearward end of tensioning or compression wire 326 to extend therefrom outside of a patient's body, thereby enabling pulling or pushing of tensioning or compression wire 326 along and relative to multi-lumen tube 302 by an operator (not shown) for bending of applicator forward tube 308, as will be described hereinbelow with reference to FIG. 12.

Successively deployed anchor 310 preferably includes a successively-deployed-anchor head 332 adapted to anchor to a tissue of an organ such as the intestine or the stomach, a successively-deployed-anchor body 334, and a successively-deployed-anchor rear portion 336 having a concaved rear surface 338 (FIGS. 11C and 11D). As illustrated in FIGS. 11B and 11C, the forward end of each successively-deployed-anchor head 332 of each anchor 310 (excluding the most forward anchor) is positioned within the concaved rear surface 338 of its frontwardly neighboring anchor 310. It is appreciated that this construction provides bendability of anchors applicator 300 with the preloaded anchors 310, as schematically illustrated in FIG. 11C. It is further appreciated that this construction allows transfer of axial forces applied by the flexible piston 320 on the rearward anchor 322 through all other anchors 310 to the most forward anchor 310, thereby allowing it to be extracted out of the forward opening of first lumen 304 through the stretched circumferential forward stopper 314.

FIG. 11D illustrates a modification of successively deployed anchor 310, wherein the successively-deployed-anchor head 332 includes a tapered head rear portion 340 at its rear portion. Tapered head rear portion 340 of successively-deployed-anchor head 332 provides easier pull-out and removal of an anchored anchor 310.

Figure 12:
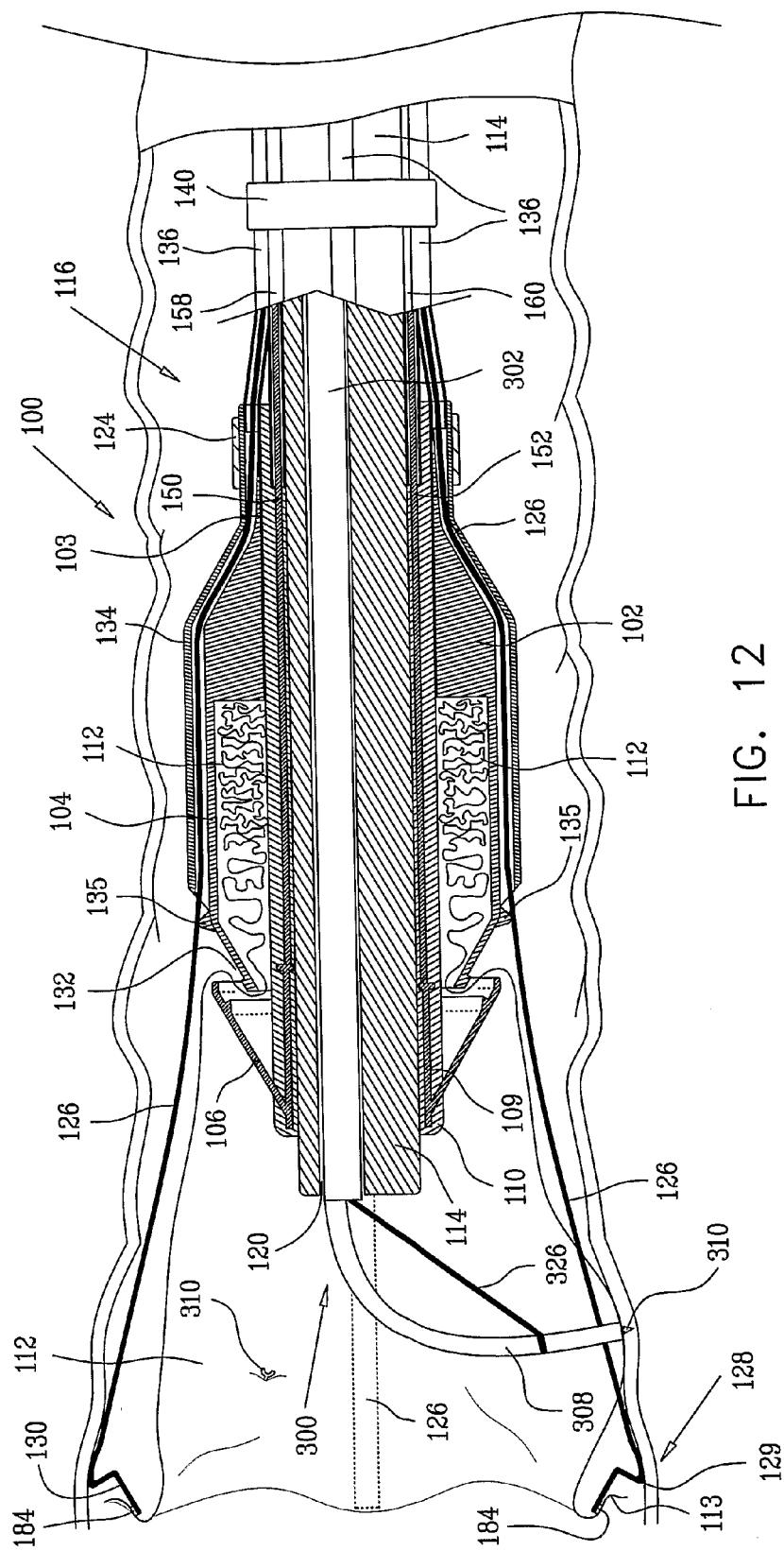
FIG. 12 is a simplified, partially sectional, illustration of the operation of the anchors applicator of FIGS. 11A-11D with the lining system of FIGS. 1A-2B.

Reference is now made to FIG. 12, which is a simplified partially sectional illustration of the operation of anchors applicator 300 with the lining system 116 of FIGS. 1A-2B. As illustrated in FIG. 12, anchors applicator 300 is located within the instrument channel 120 of endoscope 114, with its forward portion extending out of instrument channel 120 forward of lining system 116, within an intestine of a patient. As seen in FIG. 12, wire 326 is being pulled at a rearward end thereof by an operator (not shown), thereby providing selectable bending of the applicator forward tube 308 and causing engagement of the forward opening of first lumen 304 with the intestine and application of pressure thereon.

As further seen in FIG. 12, an anchor 310 is being extracted out of the forward opening of first lumen 304 as a result of application of axial force by flexible piston 320 (not shown) as described hereinabove with reference to FIG. 11B. Consequently, the successively-deployed-anchor head 332 of anchor 310 is penetrating through liner 112 and partially through the intestinal tissue, and is thus anchored to the tissue of the intestine through liner 112 and attaching liner 112 to the intestine at the anchoring location. It is appreciated that the relatively wide successively-deployed-anchor rear portion 336 cannot penetrate the liner 112 and the intestinal walls, resulting in attachment of liner 112 to the intestinal walls between rear portion 336 and the anchored head 332. It is appreciated that due to the elasticity of the intestinal tissue and preferably of the liner 112, the penetration hole made by successively-deployed-anchor head 332 in the liner 112 and the intestinal tissue is partially closed and both liner 112 and the intestinal tissue are fixedly and tightly encircling the successively-deployed-anchor body 334, with successively-deployed-anchor head 332 being located within the intestinal tissue, and successively-deployed-anchor rear portion 336 pressing liner 112 against the internal wall of the intestine at the anchoring location.

Additional anchors 310 may be deployed successively by anchors applicator 300 in a similar manner. It is appreciated that selectable rotation of anchors applicator 300 along its longitudinal axis within instrument channel 120 as well as selectable bending of applicator forward portion 308 by selectable pulling of wire 326 provide selectable positioning of the forward opening of first lumen 304 at the selected anchoring location within the intestine.

Figure 13A:
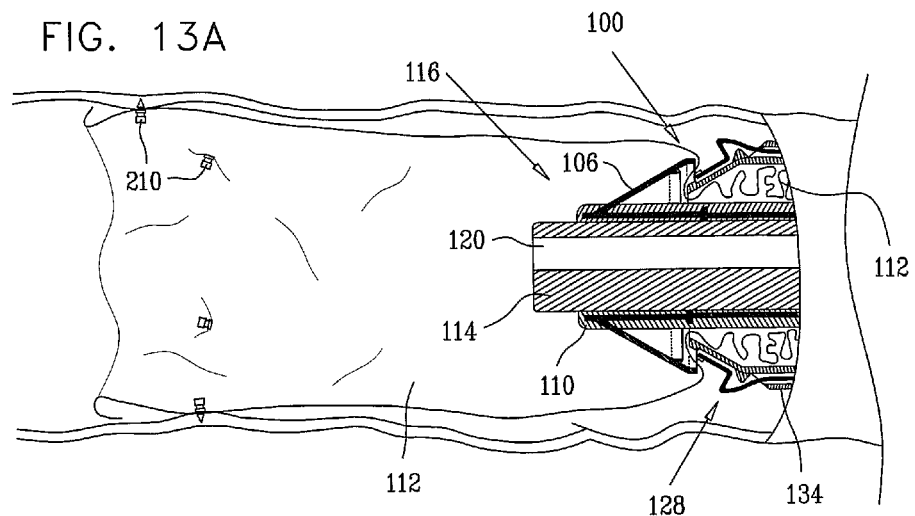
FIGS. 13A, 13B and 13C are simplified, partially sectional, illustrations of a mode of operation of the apparatus of FIGS. 1A-3B, useful for providing a selectable narrowing in a tubular body portion of a patient.
Figure 13B:
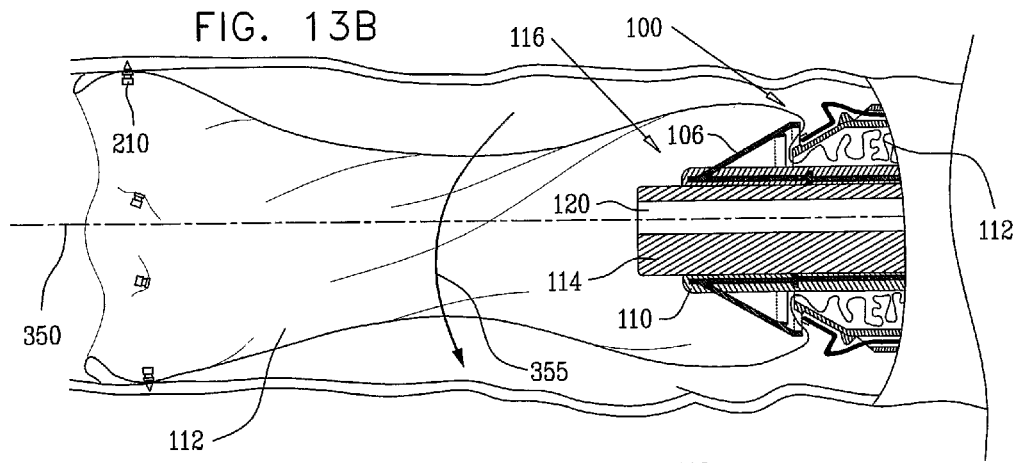
Figure 13C:
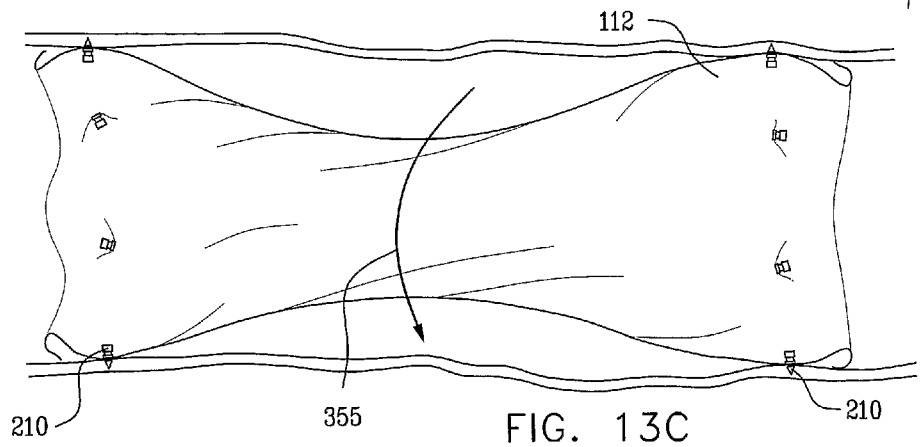

Reference is now made to FIGS. 13A, 13B and 13C which are simplified, partially sectional illustrations of a mode of operation of the apparatus of FIGS. 1A-3B, useful for providing a selectably narrowing tubular pathway implant in a tubular body portion of a patient, such as the intestine. FIG. 13A illustrates a portion of liner 112 being placed at a selectable narrowing location within the intestine of a patient, anchored to the intestine at a first anchoring location and spread rearwardly, by employing the operational sequence described hereinabove with reference to FIGS. 4A-4H. As further seen in FIG. 13A, lining system 116 is positioned at a second anchoring location within the intestine of the patient, with the liner 112 being spread between the first anchoring location and lining system 116.

As illustrated in FIG. 13B, lining system 116 is selectably rotated along its longitudinal axis, denoted in FIG. 13B by reference numeral 350, in a direction denoted by arrow 355. Rotation of lining system 116 is preferably facilitated by rotating and/or applying torque-forces on a rearward portion of endoscope 114, out of the patient's body. It is appreciated that the rotation angle around axis 350 is selectable and determined by the amount of rotation of endoscope 114 by the operator. The rotation angle of lining system 116 around its longitudinal axis 350 may be smaller than 360 degrees, or larger than 360 degrees. Specifically, lining system 116 may be rotated by approximately 30, 60, 90, 120, 180, 270 or 360 degrees.

It is appreciated that lining system 116 may be rotated either clockwise or counter-clockwise. It is further appreciated that liner 112 may be tensioned to a selectable extent as determined by the operator, by selectably pulling on a rearward portion of endoscope 114 outside of the patient's body during the rotation of lining system 116.

As further seen in FIG. 13B, liner 112 which is attached at the first anchoring location to the intestine and at the second anchoring location to the lining system 116, is selectably twisted around longitudinal axis 350 as consequence of the rotation of lining system 116. It is further seen in FIG. 13B that the cross sectional diameter of the twisted liner 112 is narrower. It is appreciated that the amount of narrowing of the cross-sectional diameter of the twisted liner 112 at the narrowing location is correlated to the amount of rotation of lining system 116 and is thus selectable by the operator. It is further appreciated that the amount of twisting of liner 112 and/or the amount of narrowing of its cross-sectional diameter can be visualized by endoscope 114 during the above-mentioned twisting and narrowing operation.

FIG. 13C illustrates the twisted liner 112 being anchored also at the second anchoring location and detached from lining system 116, by employing the operational sequence described hereinabove with reference to FIGS. 4I-4L. As seen in FIG. 13C, the attachment of the tubular liner 112 to the intestine at both sides in its twisted orientation provides narrowing of the effective cross section of the digestive tract at the liner placement location.

It is appreciated that the mode of operation of lining system 116 as described hereinabove with reference to FIGS. 13A-13C provides a selectably narrowing twisting functionality for twisting the selectably narrowable tubular liner 112, thereby to effect selectable narrowing thereof.

It is appreciated that forces applied on the twisted liner 112 by a large amount of food or stool passing therethrough may act to enlarge its narrowed cross section and thereby to reduce the amount of twisting. In order to reduce the amount of twisting of the anchored liner 112, the intestine may twist accordingly in a counter-direction. Following the passage of the food or stool through the narrowing, the forces applied on the liner 112 cease to operate, the intestine untwists, and the liner 112 returns to its fully twisted orientation of FIG. 13C. It is therefore appreciated that the selectable narrowing described hereinabove with reference to FIGS. 13A-13C may be variable according to the pressure applied by intestinal content passing therethrough. It is appreciated that the resistance of the twisted liner 112 to untwisting and to increasing its cross sectional diameter at the narrowing, depends upon the tension of the twisted liner 112 between the first and second anchoring locations and on the length of liner 112 between the first and second anchoring locations, which are both determined by the operator as described hereinabove.

It is appreciated that the narrowing described hereinabove with reference to FIGS. 13A-13C, when located within the colon of a patient, may be useful for treating a patient suffering from chronic diarrhea, by reducing stool flow speed in the colon and allowing more liquids to be absorbed by the colon. It is thus appreciated that placing such a narrowing tubular pathway implant at a desired location in an intestine of a patient may assist in treating diarrhea of the patient, and in particular chronic diarrhea.

Reference is now made to FIGS. 14A, 14B, 14C, 14D and 14E which are simplified sectional illustrations of a tubular liner forming part of the lining system of FIGS. 1A-2B, located within a stomach of a patient in accordance with a preferred embodiment and method of treatment of the present invention.

Figure 14A:
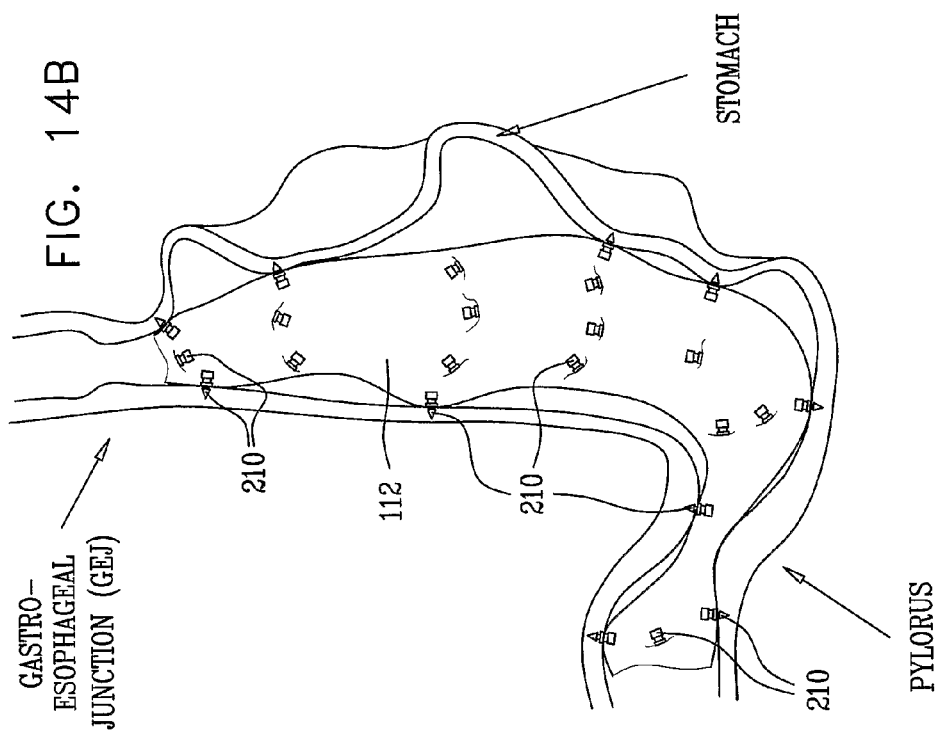

FIG. 14A illustrates the tubular liner 112 being placed and anchored within the stomach of a patient, and preferably throughout the entire length of the stomach of the patient from the gastro-esophageal junction (GEJ) to the pylorus, by employing the sequential operation described hereinabove with reference to FIGS. 4A-4L. Placing of liner 112 within the stomach of a patient, and in particular throughout the entire length of the stomach from the gastro-esophageal junction to the pylorus, may be useful for limiting the food intake by the patient and/or inducing feeling of satiety of the patient, and thereby assisting weight loss of the patient. Accordingly, as seen in FIG. 14A, an upper end portion of tubular liner 112 is anchored at or close to the gastro-esophageal junction (GEJ), and a lower end portion of liner 112 is anchored at or close to the pylorus. Food is thus limited to the volume of the tubular liner, which is generally lower than the volume of the stomach. For example, the cross-sectional diameter of tubular liner 112 placed through the stomach of a patient may be in the range of 20-50 millimeters. It is appreciated that the liner 112 may be anchored at its lower end portion in the stomach adjacent the pylorus, at the pylorus itself, in the duodenum downstream the pylorus, or further downstream within the small intestine of the patient.

Figure 14B:
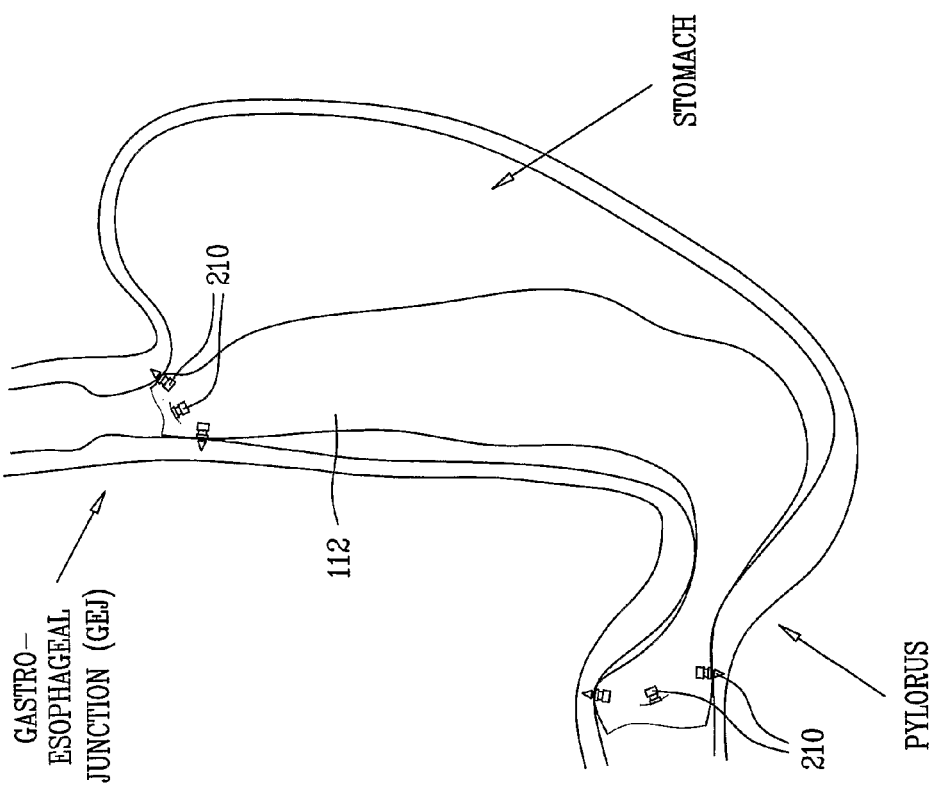

FIG. 14B illustrates liner 112 being further anchored to the stomach of the patient circumferentially at multiple locations along its length between the GEJ and the pylorus similarly to the anchoring illustrated in FIGS. 5A and 5B and preferably with a considerably larger number of individual anchors 210, thereby providing generally tight and relatively continuous engagement of the tubular liner 112 with the stomach. Consequently, the volume of the patient's stomach is actually reduced, and preferably reduced to approximately the volume of tubular liner 112. Thus, food passing through the tubular liner 112 applies pressure on at least part of the walls of the stomach through the liner 112, which pressure increases the feeling of satiety of the patient.

It is appreciated that tubular liner 112 illustrated in FIG. 14B is relatively thin and flexible, enabling the stomach of the patient to expand to a certain extent without substantially increasing its volume, between the anchoring locations along its length, as swallowed food fills the tubular liner 112, thereby increasing further the feeling of satiety of the patient. As further illustrated in FIG. 14B, the tubular liner 112 may be tensioned between its anchoring locations at both sides of the pylorus, thereby keeping the pyloric valve partially open and increasing food flow from the stomach to the intestine, thereby reducing food digestion time in the stomach.

FIG. 14C illustrates a tubular liner 112 being placed and anchored within the stomach of a patient similarly to the tubular liner illustrated in FIG. 14B (namely at both end portions of the liner and circumferentially at multiple locations along its length between the GEJ and the pylorus), and further including circumferential ring-shaped reinforced portions 250, as described hereinabove with reference to FIG. 5B, at which the individual anchors 210 are anchored circumferentially. Preferably, the reinforced portions 250 are relatively non-stretchable, thereby maintaining an approximately constant diameter under pressure of food filling the tubular liner 112. Yet preferably, the tubular liner 112 between neighboring reinforced portions 250 is relatively stretchable, thereby expanding under pressure of food filling the tubular liner 112, as illustrated in FIG. 14D. Consequently, pressure applied on the tubular liner 112 between neighboring reinforced portions 250 is passed on to at least part of the stomach walls, as denoted by thick arrows 390 in FIG. 14D, thereby applying pressure on the gastric walls and causing these walls to stretch. Both the stretching of the stomach and the pressure applied on its walls are detected by gastric receptors, which send satiety signals to the brain of the patient and induce a feeling of satiety.

It is appreciated that the tubular liner 112 of FIGS. 14A-14E may be permeable to a predetermined extent to gastric fluids, thereby allowing digestion of the swallowed food while being stored in tubular liner 112 within the stomach of the patient.

As illustrated in FIG. 14E, tubular liner 112 may comprise a multiplicity of holes 394 that permit mixing of swallowed food and gastric fluids. Holes 394 may have a relatively small cross-sectional diameter, such as in the range of 0.3-5 millimeters, or a relatively large cross-sectional diameter, such as in the range of 5-15 millimeters. It is appreciated that holes 394 having a small cross-sectional diameter may permit passage therethrough of gastric fluids into the internal volume of tubular liner 112 while not allowing passage of food therethrough into the spacing between the stomach and tubular liner 112. It is appreciated that holes 394 having a large cross-sectional diameter may permit passage therethrough of both gastric fluids and food. Holes 394 may be distributed uniformly or non-uniformly along the surface of liner 112, and may assume constant or varying cross-sectional diameters.

It is appreciated that placing such a generally stretchable tubular liner having generally non-stretchable circumferential reinforced portions in the stomach of a patient, and circumferentially anchoring the generally stretchable tubular liner to the stomach along the circumferential reinforced portions, as described hereinabove with reference to FIGS. 14A-14E, may be useful for treating obesity of a patient.

It is appreciated that though the embodiments described hereinabove refer to a tubular liner, the liner 112 does not need to be tubular, and can alternatively be open longitudinally and have a rectangular shape or a generally other shape. Such a longitudinally open liner may be utilized for example for patching, covering or isolating a portion of a treated organ of a patient, preferably during an endoscopy procedure.

It is appreciated that though the embodiments described hereinabove relate to individual anchors, another anchoring mechanism may be employed for attaching liner 112 to a tubular body portion of a patient as well known in the art, such as stapling or suturing. For example, an ESD suturing kit, available from Wilson-Cook Medical Inc., of 4900 Bethania Road, Winston-Salem, N.C. 27105 USA, may be employed. The ESD may be utilized through the instrument channel 120 of the endoscope 114 if it is sufficiently wide, or may be utilized through the external tube 294 of the lining assembly 292 described hereinabove with reference to FIG. 9 and FIG. 10. As another example, a GI-Stitch product, available from PARE Surgical Inc., of 7332 S. Alton Way, Unit H Englewood, Colo. 80112 USA, may be employed.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specifications and which are not in the prior art.

The invention claimed is:

1. A tubular body portion lining assembly adapted for insertion into a tubular body portion of a patient, said assembly comprising:
   a tubular liner container housing;
   a flexible tubular liner bunched within said tubular liner container housing;
   liner positioning functionality adapted to forwardly position at least a portion of said tubular liner from within said tubular liner container housing and to place said portion of said tubular liner between first and second locations within said tubular body portion; and
   at least one anchor adapted for anchoring said tubular liner to said tubular body portion at least a first selectable anchoring location.

2. A tubular body portion lining assembly according to claim 1 and also comprising an elongate, flexible inserter for selectably positioning said tubular liner within said tubular body portion, thereby providing a lining system.

3. A tubular body portion lining assembly according to claim 2 and wherein said inserter comprises an endoscope.

4. A tubular body portion lining assembly according to claim 1 and also comprising tubular liner detaching functionality for selectably detaching a selectable portion of said tubular liner from a remainder of said tubular liner.

5. A tubular body portion lining assembly according to claim 1 and also comprising anchoring functionality operative to cause plural ones of said at least one anchor to secure said tubular liner to said tubular body portion at multiple anchoring locations.

6. A tubular body portion lining assembly according to claim 4 and wherein said detaching functionality comprises cutting functionality operative to cut said tubular liner within said tubular body portion.

7. A tubular body portion lining assembly according to claim 1 and wherein at least said liner placing functionality is adapted to place multiple portions of said tubular liner at selectable locations within said tubular body portion.

8. A tubular body portion lining assembly adapted for insertion into a tubular body portion of a patient according to claim 7 and wherein said multiple portions of said tubular linear have at least two different lengths.

9. A tubular body portion lining assembly according to claim 1 and also comprising at least one tube traversing said tubular body portion lining assembly.

10. A tubular body portion lining assembly according to claim 1 and also comprising a selectably inflatable balloon mounted onto said tubular body portion lining assembly.

11. A tubular body portion lining assembly according to claim 1 and wherein said tubular liner comprises a plurality of generally circumferentially disposed reinforced portions.

12. A tubular body portion lining assembly according to claim 11 and wherein said tubular liner is generally stretchable intermediate said plurality of generally circumferentially disposed reinforced portions.

13. A tubular body portion lining assembly according to claim 1 and also comprising a generally tubular housing having an outer diameter greater than 2 cm in which said tubular liner is located.

14. A tubular body portion lining assembly according to claim 1 and also comprising a generally tubular housing having an outer diameter greater than 3 cm in which said tubular liner is located.

15. A tubular body portion lining assembly according to claim 1 wherein said tubular liner is selectably narrowable and also comprising: selectably narrowing twisting functionality for twisting said selectably narrowable tubular liner, thereby to effect selectable narrowing thereof.

* * * * *